(12) United States Patent
Moran et al.

(10) Patent No.: US 7,582,765 B2
(45) Date of Patent: *Sep. 1, 2009

(54) ARYL ANILINE $\beta_2$ ADRENERGIC RECEPTOR AGONISTS

(75) Inventors: Edmund J. Moran, San Francisco, CA (US); John R. Jacobsen, San Mateo, CA (US); Michael R. Leadbetter, San Leandro, CA (US); Matthew B. Nodwell, Vancouver (CA); Sean G. Trapp, San Francisco, CA (US); James Aggen, Burllingame, CA (US); Timothy J. Church, San Mateo, CA (US)

(73) Assignee: Theravance, Inc., South San San Francisco, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 11/805,101

(22) Filed: May 22, 2007

(65) Prior Publication Data

US 2007/0225329 A1    Sep. 27, 2007

Related U.S. Application Data

(63) Continuation of application No. 10/431,762, filed on May 8, 2003, now abandoned.

(51) Int. Cl.
*C07D 215/00* (2006.01)
*A01N 43/42* (2006.01)
*A01N 33/02* (2006.01)

(52) U.S. Cl. .................. 546/157; 514/312; 514/653

(58) Field of Classification Search .............. 546/157; 514/312, 653

See application file for complete search history.

(56) References Cited

U.S. PATENT DOCUMENTS

| | | | |
|---|---|---|---|
| 3,875,233 | A | 4/1975 | Bastian et al. |
| 4,021,485 | A | 5/1977 | Schromm et al. |
| 4,460,581 | A | 7/1984 | Schromm et al. |
| 4,894,219 | A | 1/1990 | Baker et al. |
| 4,992,474 | A | 2/1991 | Skidmore et al. |
| 5,064,863 | A | 11/1991 | Alig et al. |
| 5,223,614 | A | 6/1993 | Schromm et al. |
| 5,434,304 | A | 7/1995 | Trofast et al. |
| 5,750,701 | A | 5/1998 | Beeley et al. |
| 6,265,581 | B1 | 7/2001 | Bell et al. |
| 6,268,533 | B1 | 7/2001 | Gao et al. |
| 6,541,669 | B1 | 4/2003 | Moran et al. |
| 6,576,793 | B1 | 6/2003 | Moran et al. |
| 6,653,323 | B2 * | 11/2003 | Moran et al. ............. 514/312 |
| 6,670,376 | B1 * | 12/2003 | Moran et al. ............. 514/312 |
| 6,949,568 | B2 * | 9/2005 | Moran et al. ............. 514/312 |
| 7,060,712 | B2 * | 6/2006 | Axt et al. .................. 514/312 |
| 7,125,892 | B2 | 10/2006 | Moran et al. |
| 2002/0022625 | A1 | 2/2002 | Walland et al. |
| 2002/0177581 | A1 | 11/2002 | Biggadlke |
| 2003/0045512 | A1 | 3/2003 | Biggadlke |

FOREIGN PATENT DOCUMENTS

| | | |
|---|---|---|
| BE | 849 794 | 4/1977 |
| CH | 550 768 | 2/1972 |
| EP | 0 147 719 B1 | 7/1989 |
| JP | 52 83379 | 7/1977 |
| WO | WO 95/25104 | 9/1995 |
| WO | WO 02/066422 A1 | 8/2002 |
| WO | WO 02/070490 A1 | 9/2002 |
| WO | WO 02/076933 A1 | 10/2002 |

OTHER PUBLICATIONS

Pang et.al. American Journal of Respiratory Cell and Molecular Biology, 23, pp. 79-85, 2000.*
Herner et al., "Combined Ipratropium and $\beta_2$-Adrenergic Receptor Agonist in Acute Asthma", Journal of the American Board of Family Practice, 2000, 13(1), pp. 55-65.
Isogaya et al., "Binding Pockets of the $\beta_1$-and $\beta_2$-Adrenergic Receptors for Subtype-Selective Agonists", Molecular Pharmacology, vol. 56, pp. 875-885 (1999).
Milecki et al., "Carbostyril Derivatives Having Potent $\beta$-Adrenergic Agonist Properties", J. Med. Chem., vol. 30, pp. 1563-1566 (1987).
Nelson et al., "Fluticasone propionate/salmeterol combination provides more effective asthma control than low-dose inhaled corticosteroid plus montelukast", 2000, 106(6), pp. 1088-1095.
Yokoi et al., "The Development of a Radioimmunoassay for Formoterol", Life Sciences, vol. 33, pp. 1665-1672 (1983).
Yoshizaki et al., "Sympathomimetic Amines Having a Carbostyril Nucleus", Journal of Med. Chem., vol. 19, No. 9, pp. 1138-1142 (1976).

* cited by examiner

*Primary Examiner*—D. Margaret Seaman
*Assistant Examiner*—Nizal S Chandrakumar
(74) *Attorney, Agent, or Firm*—Jeffrey A. Hagenah; Roberta P. Saxon

(57) ABSTRACT

The invention provides novel $\beta_2$ adrenergic receptor agonist compounds of formula (I):

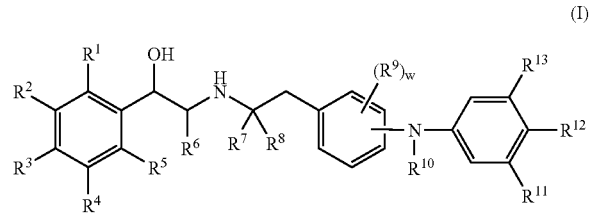

(I)

wherein $R^1$-$R^{13}$ and w have any of the values described in the specification. The invention also provides combinations of such compounds and other therapeutic agents, pharmaceutical compositions comprising such compounds and combinations, methods of using such compounds to treat diseases associated with $\beta_2$ adrenergic receptor activity, and processes and intermediates useful for preparing such compounds.

16 Claims, No Drawings

ARYL ANILINE β₂ ADRENERGIC RECEPTOR AGONISTS

CROSS REFERENCE TO RELATED APPLICATIONS

This application is a continuation of U.S. application Ser. No. 10/431,762, filed May 8, 2003, now abandoned the entire disclosure of which is incorporated herein by reference.

FIELD OF THE INVENTION

The invention is directed to novel β₂ adrenergic receptor agonists. The invention is also directed to pharmaceutical compositions comprising such compounds, methods of using such compounds to treat diseases associated with β₂ adrenergic receptor activity, and processes and intermediates useful for preparing such compounds.

BACKGROUND OF THE INVENTION

β₂ adrenergic receptor agonists are recognized as effective drugs for the treatment of pulmonary diseases such as asthma and chronic obstructive pulmonary disease (including chronic bronchitis and emphysema). β₂ adrenergic receptor agonists are also useful for treating pre-term labor, and are potentially useful for treating neurological disorders and cardiac disorders. In spite of the success that has been achieved with certain β₂ adrenergic receptor agonists, current agents possess less than desirable potency, selectivity, speed of onset, and/or duration of action. Thus, there is a need for additional β₂ adrenergic receptor agonists having improved properties. Preferred agents may possess, among other properties, improved duration of action, potency, selectivity, and/or onset.

SUMMARY OF THE INVENTION

The invention provides novel compounds that possess β₂ adrenergic receptor agonist activity. Accordingly, this invention provides compounds of formula (I):

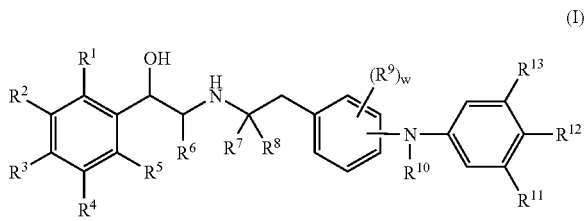

(I)

wherein:

each of $R^1$-$R^5$ is independently selected from the group consisting of hydrogen, alkyl, alkenyl, alkynyl, aryl, heteroaryl, cycloalkyl, heterocyclyl, and $R^a$;

or $R^1$ and $R^2$, $R^2$ and $R^3$, $R^3$ and $R^4$, or $R^4$ and $R^5$ are joined together to form a group selected from the group consisting of —C($R^d$)=C($R^d$)C(=O)N$R^d$—, —C$R^d R^d$—C$R^d R^d$—C(=O)N$R^d$—, —N$R^d$C(=O)C($R^d$)=C($R^d$)—, —N$R^d$C(=O)C$R^d R^d$—C$R^d R^d$—, —N$R^d$C(=O)S—, —SC(=O)N$R^d$—, —(C$R^d R^d$)$_p$—, —S(C$R^d R^d$)$_q$—, —(C$R^d R^d$)$_q$S—, —S(C$R^d R^d$)$_r$O—, —O(C$R^d R^d$)$_r$S—, and —NHC($R^k$)=C($R^k$)—;

$R^6$ is hydrogen, alkyl, or alkoxy;
$R^7$ is hydrogen or alkyl;
$R^8$ is hydrogen or alkyl; or $R^8$ together with $R^9$ is —CH₂— or —CH₂CH₂—;
$R^9$ is independently selected from the group consisting of alkyl, alkenyl, alkynyl, aryl, heteroaryl, cycloalkyl, heterocyclyl, and $R^a$, or $R^9$ together with $R^8$ is —CH₂— or —CH₂CH₂—;
$R^{10}$ is hydrogen or alkyl;
each $R^{11}$, $R^{12}$, and $R^{13}$ is independently selected from the group consisting of hydrogen, alkyl, cycloalkyl, alkenyl, alkynyl, aryl, heteroaryl, heterocyclyl, —NO₂, halo, —N$R^d R^e$, —C(=O)$R^d$, —CO₂$R^d$, —OC(=O)$R^d$, —CN, —C(=O)N$R^d R^e$, —N$R^d$C(=O)$R^e$, —OC(=O)N$R^d R^e$, —N$R^d$C(=O)O$R^e$, —N$R^d$C(=O)N$R^d R^e$, —O$R^d$, —S(O)$_m R^d$, —N$R^d$—N$R^d$—C(=O)$R^d$, —N$R^d$—N=C$R^d R^d$, —N(N$R^d R^e$)$R^d$, and —S(O)₂N$R^d R^e$;

or $R^{11}$ and $R^{12}$ together with the atoms to which they are attached form a fused benzo ring, which benzo ring can optionally be substituted with 1, 2, 3, or 4 $R^c$;
or $R^{11}$ and $R^{12}$ together with the atoms to which they are attached form a heterocyclic ring;
wherein for $R^1$-$R^6$, $R^9$, and $R^{11}$-$R^{13}$, each alkyl, alkenyl, and alkynyl is optionally substituted with $R^m$, or with one or more (e.g. 1, 2, 3, or 4) substituents independently selected from $R^b$; for $R^1$-$R^6$, $R^9$, and $R^{11}$-$R^{13}$, each aryl and heteroaryl is optionally substituted with 1, 2, 3, or 4 substituents independently selected from $R^c$, and for $R^1$-$R^6$, $R^9$, and $R^{11}$-$R^{13}$ each cycloalkyl and heterocyclic ring is optionally substituted with 1, 2, 3, or 4 substituents independently selected from $R^b$ and $R^c$;

each $R^a$ is independently —O$R^d$, —NO₂, halo, —S(O)$_m R^d$, —S(O)₂O$R^d$, —S(O)$_m$N$R^d R^e$, —N$R^d R^e$, —O(C$R^f R^g$)$_n$N$R^d R^e$, —C(=O)$R^d$, —CO₂$R^d$, —CO₂(C$R^f R^g$)$_n$CON$R^d R^e$, —OC(=O)$R^d$, —CN, —C(=O)N$R^d R^e$, —N$R^d$C(=O)$R^e$, —OC(=O)N$R^d R^e$, —N$R^d$C(=O)O$R^e$, —N$R^d$C(=O)N$R^d R^e$, —C$R^d$(=N—O$R^e$), —CF₃, or —OCF₃;

each $R^b$ is independently $R^a$, oxo, or =N—O$R^e$;
each $R^e$ is independently $R^a$, alkyl, alkenyl, or alkynyl; wherein each alkyl, alkenyl and alkynyl is optionally substituted with 1, 2, 3, or 4 substituents independently selected from $R^b$;

each $R^d$ and $R^e$ is independently hydrogen, alkyl, alkenyl, alkynyl, aryl, heteroaryl, cycloalkyl, or heterocyclyl; wherein each alkyl, alkenyl, alkynyl, aryl, heteroaryl, cycloalkyl and heterocyclyl is optionally substituted with one or more (e.g. 1, 2, 3, or 4) substituents independently selected from $R^h$; or $R^d$ and $R^e$ together with the atoms to which they are attached form a heterocyclic ring having from 5 to 7 ring atoms, wherein the heterocyclic ring optionally contains 1 or 2 additional heteroatoms independently selected from oxygen, sulfur and nitrogen;

each $R^f$ and $R^g$ is independently hydrogen, alkyl, aryl, heteroaryl, cycloalkyl, or heterocyclyl; wherein each alkyl, aryl, heteroaryl, cycloalkyl and heterocyclyl is optionally substituted with 1, 2, 3, or 4 substituents independently selected from $R^h$; or $R^f$ and $R^g$ together with the carbon atom to which they are attached form a ring having from 5 to 7 ring atoms, wherein the ring optionally contains 1 or 2 heteroatoms independently selected from oxygen, sulfur and nitrogen;

each $R^h$ is independently halo, $C_{1-8}$alkyl, $C_{1-8}$alkoxy, —S—$C_{1-8}$alkyl, aryl, (aryl)-$C_{1-6}$alkyl, (aryl)-$C_{1-8}$alkoxy, heteroaryl, (heteroaryl)-$C_{1-6}$alkyl, (heteroaryl)-$C_{1-8}$alkoxy, hydroxy, amino, —NHC$_{1-6}$alkyl, —N(C$_{1-6}$alkyl)₂, —OC(=O)C$_{1-6}$alkyl, —C(=O)C$_{1-6}$alkyl, —C(=O)OC$_{1-6}$alkyl, —NHC(=O)C$_{1-6}$alkyl, —C(=O)NHC$_{1-6}$alkyl, carboxy, nitro, —CN, or —CF₃;

$R^j$ and $R^k$ together with the carbon atoms to which they are attached form a phenyl ring that is optionally substituted with 1, 2, 3, or 4 $R^c$;

each $R^m$ is independently aryl, heteroaryl, cycloalkyl or heterocyclyl; wherein each aryl or heteroaryl is optionally substituted with 1, 2, 3, or 4 substituents selected from the group consisting of $R^c$, and wherein each cycloalkyl and heterocyclyl is optionally substituted with 1, 2, 3, or 4 substituents selected from $R^b$;

m is 0, 1, or 2;

n is 0, 1, 2, 3, 4, 5, 6, 7, 8, 9, or 10;

p is 3, 4, or 5;

q is 2, 3, or 4;

r is 1, 2, or 3;

w is 0, 1, 2, 3, or 4;

or a pharmaceutically-acceptable salt or solvate or stereoisomer thereof.

The invention also provides compounds of formula (IIa):

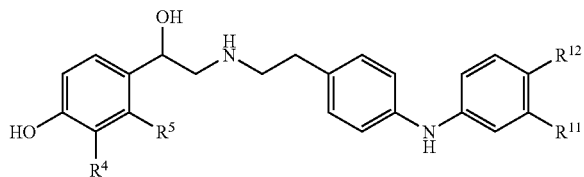

(IIa)

wherein:

$R^4$ is —CH$_2$OH or —NHCHO and $R^5$ is hydrogen; or $R^4$ and $R^5$ taken together are —NHC(=O)CH=CH—;

$R^{11}$ is phenyl or heteroaryl, wherein each phenyl is optionally substituted with 1 or 2 substituents selected from halo, —OR$^d$, —CN, —NO$_2$, —SO$_2$R$^d$, —C(=O)R$^d$, —C(=O)NR$^d$R$^e$, and C$_{1-3}$alkyl, wherein C$_{1-3}$alkyl is optionally substituted with 1 or 2 substituents selected from carboxy, hydroxy, and amino, and each R$^d$ and R$^e$ is independently hydrogen or C$_{1-3}$alkyl; and wherein each heteroaryl is optionally substituted with 1 or 2 C$_{1-3}$alkyl substituents; and $R^{12}$ is hydrogen or —OC$_{1-6}$alkyl;

or a pharmaceutically-acceptable salt or solvate or stereoisomer thereof.

The invention also provides compounds of formula (IIb):

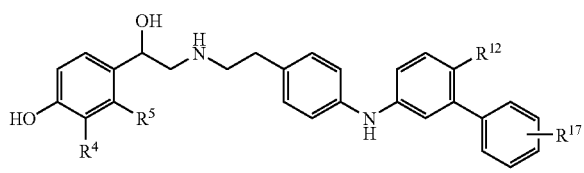

(IIb)

wherein:

$R^4$ is —CH$_2$OH or —NHCHO and $R^5$ is hydrogen; or $R^4$ and $R^5$ taken together are —NHC(=O)CH=CH—;

$R^{12}$ is hydrogen or —OC$_{1-6}$alkyl;

$R^{17}$ is —(CH$_2$)$_x$NR$^d$R$^e$ wherein each R$^d$ and R$^e$ is independently hydrogen or C$_{1-4}$alkyl, wherein each C$_{1-4}$alkyl is optionally substituted with phenyl or pyridyl, or R$^d$ and R$^e$ together with the nitrogen atom to which they are attached is morpholino; and x is 0, 1, or 2.

The invention also provides a pharmaceutical composition comprising a compound of the invention and a pharmaceutically-acceptable carrier. The invention further provides combinations comprising a compound of the invention and one or more other therapeutic agents and pharmaceutical compositions comprising such combinations.

The invention also provides a method of treating a disease or condition associated with β$_2$ adrenergic receptor activity (e.g. a pulmonary disease, such as asthma or chronic obstructive pulmonary disease, pre-term labor, a neurological disorder, a cardiac disorder, or inflammation) in a mammal, comprising administering to the mammal, a therapeutically effective amount of a compound of the invention. The invention further provides a method of treatment comprising administering a therapeutically effective amount of a combination of a compound of the invention together with one or more other therapeutic agents.

The invention also provides a method of treating a disease or condition associated with β$_2$ adrenergic receptor activity (e.g. a pulmonary disease, such as asthma or chronic obstructive pulmonary disease, pre-term labor, a neurological disorder, a cardiac disorder, or inflammation) in a mammal, comprising administering to the mammal, a therapeutically effective amount of a pharmaceutical composition of the invention.

This invention also provides a method of modulating a β$_2$ adrenergic receptor, the method comprising stimulating a β$_2$ adrenergic receptor with a modulatory amount of a compound of the invention.

In separate and distinct aspects, the invention also provides synthetic processes and novel intermediates, including compounds of formulas (III), (IV), and (VII) described herein, which are useful for preparing compounds of the invention.

The invention also provides a compound of the invention as described herein for use in medical therapy, as well as the use of a compound of the invention in the manufacture of a formulation or medicament for treating a disease or condition associated with β$_2$ adrenergic receptor activity (e.g. a pulmonary disease, such as asthma or chronic obstructive pulmonary disease, pre-term labor, a neurological disorder, a cardiac disorder, or inflammation) in a mammal.

DETAILED DESCRIPTION OF THE INVENTION

When describing the compounds, compositions and methods of the invention, the following terms have the following meanings, unless otherwise indicated.

The term "alkyl" refers to a monovalent saturated hydrocarbon group which may be linear or branched or combinations thereof. Such alkyl groups preferably contain from 1 to 20 carbon atoms; more preferably, from 1 to 8 carbon atoms; and still more preferably, from 1 to 4 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkenyl" refers to a monovalent unsaturated hydrocarbon group containing at least one carbon-carbon double bond, typically 1 or 2 carbon-carbon double bonds, and which may be linear or branched or combinations thereof. Such alkenyl groups preferably contain from 2 to 20 carbon atoms; more preferably from 2 to 8 carbon atoms; and still more preferably, from 2 to 4 carbon atoms. Representative alkenyl groups include, by way of example, vinyl, allyl, isopropenyl, but-2-enyl, n-pent-2-enyl, n-hex-2-enyl, n-hept-2-enyl, n-oct-2-enyl, n-non-2-enyl, n-dec-4-enyl, n-dec-2,4-dienyl and the like.

The term "alkynyl" refers to a monovalent unsaturated hydrocarbon group containing at least one carbon-carbon triple bond, typically 1 carbon-carbon triple bond, and which may be linear or branched or combinations thereof. Such alkynyl groups preferably contain from 2 to 20 carbon atoms; more preferably from 2 to 8 carbon atoms; and still more preferably, from 2 to 4 carbon atoms. Representative alkynyl groups include, by way of example, ethynyl, propargyl, but-2-ynyl and the like.

The term "alkoxy" refers to a group of the formula —OR, where R is an alkyl group as defined herein. Representative alkoxy groups include, by way of example, methoxy, ethoxy, n-propoxy, isopropoxy, n-butoxy, sec-butoxy, isobutoxy, tert-butoxy, n-pentoxy, n-hexoxy and the like.

The term "cycloalkyl" refers to a monovalent saturated carbocyclic group which may be monocyclic or multicyclic. Each ring of such cycloalkyl groups preferably contains from 3 to 10 carbon atoms. This term also includes cycloalkyl groups fused to an aryl or heteroaryl group in which the point of attachment is on the non-aromatic (cycloalkyl) portion of the group. Representative cycloalkyl groups include, by way of example, cyclopropyl, cyclobutyl, cyclopentyl, cyclohexyl, cycloheptyl, cyclooctyl, 1,2,3,4-tetrahydronaphth-2-yl, decahydronaphthyl, indan-1-yl, adamantyl, norbornyl and the like.

The term "aryl" refers to a monovalent carbocyclic group which may be monocyclic or multicyclic (i.e., fused) wherein at least one ring is aromatic. Such aryl groups preferably contain from 6 to 20 carbon atoms; more preferably, from 6 to 10 carbon atoms. This term includes multicyclic carbocyclic ring systems wherein one or more rings are not aromatic, provided the point of attachment is on an aromatic ring. Representative aryl groups include, by way of example, phenyl, napthyl, azulenyl, indan-5-yl, 1,2,3,4-tetrahydronaphth-6-yl, and the like.

The term "heteroaryl" refers to a monovalent aromatic group that contains at least one heteroatom, preferably 1 to 4 heteroatoms, selected from N, S and O, and which may be monocyclic or multicyclic (i.e., fused). Such heteroaryl groups preferably contain from 5 to 20 atoms; more preferably, from 5 to 10 atoms. This term also includes heteroaryl groups fused to a cycloalkyl or aryl group, in which the point of attachment is on the aromatic (heteroaryl) portion of the group. Representative heteroaryl groups include, by way of example, pyrroyl, isoxazolyl, isothiazolyl, pyrazolyl, pyridyl (or, equivalently, pyridinyl), oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, quinolyl, indolyl, isoquinolyl and the like.

The term "heterocyclyl" or "heterocyclic ring" refers to a saturated or partially unsaturated cyclic non-aromatic group, which may be monocyclic or multicyclic (i.e., fused or bridged), and which contains at least one heteroatom, preferably 1 to 4 heteroatoms, selected from N(X), S and O, wherein each X is independently hydrogen or alkyl. Such heterocyclyl groups preferably contain from 3 to 20 atoms; more preferably, from 3 to 10 atoms. This term also includes such a heterocyclyl group fused to one or more cycloalkyl, aryl, or heteroaryl groups. The point of attachment of the heterocyclyl group may be any carbon or nitrogen atom in a heterocyclyl, cycloalkyl, aryl or heteroaryl portion of the group. Representative heterocyclyl groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl, 2-oxobenzopyran, and the like.

The term "halo" refers to a fluoro, chloro, bromo or iodo.

The term "oxo" refers to a group of the formula =O.

The term "therapeutically effective amount" refers to an amount sufficient to effect treatment when administered to a patient in need of treatment.

The term "treatment" as used herein refers to the treatment of a disease or medical condition in a patient, such as a mammal (particularly a human), and includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The phrase "disease or condition associated with $\beta_2$ adrenergic receptor activity" includes all disease states and/or conditions that are acknowledged now, or that are found in the future, to be associated with $\beta_2$ adrenergic receptor activity. Such disease states include, but are not limited to, bronchoconstrictive or pulmonary diseases, such as asthma and chronic obstructive pulmonary disease (including chronic bronchitis and emphysema), as well as neurological disorders and cardiac disorders. $\beta_2$ Adrenergic receptor activity is also known to be associated with pre-term labor (see, for example, U.S. Pat. No. 5,872,126) and some types of inflammation (see, for example, WO 99/30703 and U.S. Pat. No. 5,290,815).

The term "pharmaceutically-acceptable salt" refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically-acceptable acids include acetic, benzenesulfonic, benzoic, camphosulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid) and the like. Particularly preferred are salts derived from fumaric, hydrobromic, hydrochloric, acetic, sulfuric, phosphoric, methanesulfonic, p-toluenesulfonic, xinafoic, tartaric, citric, malic, maleic, succinic, and benzoic acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like.

The term "solvate" refers to a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

The term "leaving group" refers to a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" refers to a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" refers to a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Specific and preferred values listed below for radicals, substituents, and ranges, are for illustration only; they do not exclude other defined values or other values within defined ranges for the radicals and substituents.

A specific value for $R^1$ is hydrogen.
A specific value for $R^2$ is hydrogen.
A specific value for $R^3$ is hydroxy.
A specific value for $R^4$ is —$CH_2OH$ or —NHCHO.
A specific value for $R^5$ is hydrogen.
A specific value for $R^4$ and $R^5$ together are —NHC(=O)CH=CH— or —SC(=O)NH—.
A specific value for $R^6$ is hydrogen.
A specific value for $R^7$ is hydrogen.
A specific value for $R^8$ is hydrogen.
A specific value for w is 0.
Another specific value for w is 1 or 2.
A specific value for $R^9$ together with $R^8$ is —$CH_2$— or —$CH_2CH_2$—.
A specific value for $R^{10}$ is hydrogen.
Another specific value for $R^{10}$ is alkyl.
A specific value for $R^{11}$ is hydrogen.
Another specific value for $R^{11}$ is alkyl, alkenyl, alkynyl, aryl, heteroaryl, heterocyclyl, —$NO_2$, halo, —$NR^dR^e$, —C(=O)$R^d$, —$CO_2R^d$, —OC(=O)$R^d$, —CN, —C(=O)$NR^dR^e$, —$NR^dC$(=O)$R^e$, —OC(=O)$NR^dR^e$, —$NR^dC$(=O)$OR^e$, —$NR^dC$(=O)$NR^dR^e$, —$OR^d$, —S(O)$_mR^d$, —$NR^d$—$NR^d$—C(=O)$R^d$, —$NR^d$—N=$CR^dR^d$, —N($NR^dR^e$)$R^d$, or —S(O)$_2NR^dR^e$.
Another specific value for $R^{11}$ is hydrogen, alkyl, heterocyclyl, —$OR^d$, —S(O)$_mR^d$, or —S(O)$_2NR^dR^e$.

Another specific value for $R^{11}$ is heterocyclyl, —$OR^d$, —S(O)$_mR^d$, or —S(O)$_2NR^dR^e$.
Another specific value for $R^{11}$ is —$OR^d$.
Another specific value for $R^{11}$ is —S(O)$_mR^d$.
A specific value for $R^{12}$ is hydrogen.
Another specific value for $R^{12}$ is alkyl, alkenyl, alkynyl, aryl, heteroaryl, heterocyclyl, —$NO_2$, halo, —$NR^dR^e$, —C(=O)$R^d$, —$CO_2R^d$, —OC(=O)$R^d$, —CN, —C(=O)$NR^dR^e$, —$NR^dC$(=O)$R^e$, —OC(=O)$NR^dR^e$, —$NR^dC$(=O)$OR^e$, —$NR^dC$(=O)$NR^dR^e$, —$OR^d$, —S(O)$_mR^d$, —$NR^d$—$NR^d$—C(=O)$R^d$, —$NR^d$—N=$CR^dR^d$, —N($NR^dR^e$)$R^d$, or —S(O)$_2NR^dR^e$.
Another specific value for $R^{12}$ is hydrogen, alkyl, heterocyclyl, —$OR^d$, —S(O)$_mR^d$, or —S(O)$_2NR^dR^e$.
A specific value for $R^{12}$ is heterocyclyl, —$OR^d$, —S(O)$_mR^d$, or —S(O)$_2NR^dR^e$.
Another specific value for $R^{12}$ is —$OR^d$.
Another specific value for $R^{12}$ is —S(O)$_mR^d$.
Another specific value for $R^{12}$ is —S(O)$_2NR^dR^e$.
A specific value for $R^{13}$ is hydrogen.
Another specific value for $R^{13}$ is alkyl, alkenyl, alkynyl, aryl, heteroaryl, heterocyclyl, —$NO_2$, halo, —$NR^dR^e$, —C(=O)$R^d$, —$CO_2R^d$, —OC(=O)$R^d$, —CN, —C(=O)$NR^dR^e$, —$NR^dC$(=O)$R^e$, —OC(=O)$NR^dR^e$, —$NR^dC$(=O)$OR^e$, —$NR^dC$(=O)$NR^dR^e$, —$OR^d$, —S(O)$_mR^d$, —$NR^d$—$NR^d$—C(=O)$R^d$, —$NR^d$—N=$CR^dR^d$, —N($NR^dR^e$)$R^d$, or —S(O)$_2NR^dR^e$.
Another specific value for $R^{13}$ is hydrogen, alkyl, heterocyclyl, —$OR^d$, —S(O)$_mR^d$, or —S(O)$_2NR^dR^e$.
Another specific value for $R^{13}$ is heterocyclyl, —$OR^d$, —S(O)$_mR^d$, or —S(O)$_2NR^dR^e$.
A specific value for $R^{13}$ is —$OR^d$.
A specific value for $R^{13}$ is —S(O)$_mR^d$.

A specific group of compounds of the invention are compounds wherein each of $R^1$-$R^4$ is independently selected from the group consisting of hydrogen, fluoro, chloro, amino, hydroxy, N,N-dimethylaminocarbonyloxy, —$CH_2OH$, and —NHCHO, and $R^5$ is hydrogen; or $R^1$ is hydrogen, $R^2$ is hydrogen, $R^3$ is hydroxy, and $R^4$ and $R^5$ together are —NHC(=O)CH=CH— or —SC(=O)NH—.

A specific group of compounds of the invention are compounds wherein $R^1$ is hydrogen; $R^2$ is chloro; $R^3$ is amino; $R^4$ is chloro; and $R^5$ is hydrogen.

A specific group of compounds of the invention are compounds wherein $R^1$ is hydrogen; $R^2$ is N,N-dimethylaminocarbonyloxy; $R^3$ is hydrogen; $R^4$ is N,N-dimethylaminocarbonyloxy; and $R^5$ is hydrogen.

A specific group of compounds of the invention are compounds wherein $R^1$ is hydrogen, fluoro, or chloro; $R^2$ is hydroxy; $R^3$ is hydrogen; $R^4$ is hydroxy; and $R^5$ is hydrogen.

A specific group of compounds of the invention are compounds wherein $R^1$ is chloro; $R^2$ is hydrogen; $R^3$ is hydroxy; $R^4$ is hydrogen; and $R^5$ is hydrogen.

A specific group of compounds of the invention are compounds wherein $R^1$ is hydrogen; $R^2$ is hydrogen; $R^3$ is hydroxy; $R^4$ is —$CH_2OH$; and $R^5$ is hydrogen.

A specific group of compounds of the invention are compounds wherein $R^1$ is hydrogen; $R^2$ is hydrogen; $R^3$ is hydroxy; $R^4$ is —NHCHO; and $R^5$ is hydrogen.

A specific group of compounds of the invention are compounds wherein $R^1$ is hydrogen; $R^2$ is hydrogen; $R^3$ is hydroxy; and $R^4$ and $R^5$ together are —NHC(=O)CH=CH—.

A specific group of compounds of the invention are compounds wherein $R^1$ is hydrogen; $R^2$ is hydrogen; $R^3$ is hydroxy; and $R^4$ and $R^5$ together are —SC(=O)NH—.

A specific group of compounds of the invention are compounds wherein $R^{11}$ is hydrogen, $R^{12}$ is —$SR^d$; $R^{13}$ is hydrogen; and $R^d$ is alkyl, aryl, or heteroaryl.

A specific group of compounds of the invention are compounds wherein $R^{11}$ is —$SR^d$, $R^{12}$ is hydrogen; $R^{13}$ is hydrogen; and $R^d$ is alkyl, aryl, heteroaryl.

When part of the group —$SR^d$, a specific value for $R^d$ is alkyl.

When part of the group —$SR^d$, another specific value for $R^d$ is $C_{1-6}$alkyl.

When part of the group —$SR^d$, another specific value for $R^d$ is $C_{1-3}$alkyl.

When part of the group —$SR^d$, another more specific value for $R^d$ is aryl optionally substituted with 1, 2, 3, or 4 substituents independently selected from halo, $C_{1-6}$alkyl, $C_{1-6}$alkoxy, hydroxy, amino, —$N(C_{1-6}$alkyl$)_2$, nitro, —CN, and —$CF_3$.

When part of the group —$SR^d$, another more specific value for $R^d$ is phenyl optionally substituted with 1, 2, 3, or 4 substituents independently selected from fluoro and $C_{1-3}$alkyl.

A specific group of compounds of the invention are compounds wherein $R^{11}$ or $R^{12}$ is methylthio, 2-methylphenylthio, 4-methyl-2-pyrimidylthio, 4-fluorophenylthio, or 4-methylphenylthio.

A specific group of compounds of the invention are compounds wherein $R^{11}$ is hydrogen or alkyl, $R^{12}$ is —$SO_2NR^dR^e$; and $R^{13}$ is hydrogen.

A specific group of compounds of the invention are compounds wherein $R^{11}$ is —$SO_2NR^dR^e$, $R^{12}$ is hydrogen or alkyl; and $R^{13}$ is hydrogen.

When part of the group —$SO_2NR^dR^e$, a specific value for $R^d$ is alkyl, aryl, or heteroaryl; and for $R^e$ is hydrogen, alkyl, aryl, or heteroaryl; wherein each alkyl, aryl, or heteroaryl, is optionally substituted with one or more (e.g. 1, 2, 3, or 4) substituents independently selected from $R^h$; or $R^d$ and $R^e$ together with the nitrogen atom to which they are attached is a heterocyclic ring having from 5 to 7 ring atoms, wherein the heterocyclic ring optionally contains 1 or 2 additional heteroatoms independently selected from oxygen, sulfur or nitrogen.

When part of the group —$SO_2NR^dR^e$, a specific value for $R^d$ and $R^e$ independently is hydrogen, alkyl, aryl, or heteroaryl; wherein each alkyl, aryl, or heteroaryl, is optionally substituted with 1, 2, 3, or 4 substituents independently selected from $R^h$.

As a substituent as part of the group —$SO_2NR^dR^e$, a specific value for $R^h$ is halo, $C_{1-8}$alkyl, $C_{1-8}$alkoxy, —S—$C_{1-8}$alkyl, aryl, hydroxy, amino, —$NHC_{1-8}$alkyl, —N($C_{1-6}$alkyl$)_2$, —OC(=O)$C_{1-6}$alkyl, —C(=O)$C_{1-6}$alkyl, —C(=O)O$C_{1-6}$alkyl, —NHC(=O)$C_{1-6}$alkyl, —C(=O)NH$C_{1-6}$alkyl, carboxy, nitro, —CN, or —$CF_3$.

Another specific value for $R^h$ in the above context is halo, $C_{1-6}$alkyl, $C_{1-6}$alkoxy, or —$CF_3$.

When part of the group —$SO_2NR^dR^e$, a specific value for $R^d$ and $R^e$ together with the nitrogen atom to which they are attached is a heterocyclic ring having from 5 to 7 ring atoms, wherein the heterocyclic ring optionally contains 1 or 2 additional heteroatoms independently selected from oxygen, sulfur or nitrogen.

When part of the group —$SO_2NR^dR^e$, a specific value for $R^d$ and $R^e$ independently is alkyl; wherein each alkyl is optionally substituted with 1 or 2 alkoxy substituents.

When part of the group —$SO_2NR^dR^e$, a specific value for $R^d$ or $R^e$ is phenyl, or naphthyl; wherein each phenyl and naphthyl is optionally substituted with 1, 2, 3, or 4 substituents independently selected from halo, $C_{1-6}$alkyl, $C_{1-6}$alkoxy, and —$CF_3$.

When part of the group —$SO_2NR^dR^e$, a specific value for $R^d$ or $R^e$ is heteroaryl; wherein each heteroaryl is optionally substituted with 1, 2, 3, or 4 substituents independently selected from halo, $C_{1-6}$alkyl, $C_{1-6}$alkoxy, and —$CF_3$. Preferably heteroaryl is pyridyl, pyrimidyl, or thiazolyl.

A preferred group of compounds are compounds wherein $R^{11}$ or $R^{12}$ is —$SO_2NR^dR^e$; wherein $R^d$ is 4-heptyl-6-methyl-2-pyrimidyl, 5-methoxy-2-pyrimidyl, 2-pyridyl, phenyl, 2,6-dimethylphenyl, 2-thiazoyl, 2-trifluoromethylphenyl, or 3,5-dichlorophenyl; and $R^e$ is hydrogen or ethyl.

Another preferred group of compounds are compounds of the invention wherein $R^{11}$ or $R^{12}$ is —$SO_2NR^dR^e$; wherein $R^d$ and $R^e$ together with the atoms to which they are attached are piperidino or morpholino.

A specific group of compounds of the invention are compounds wherein $R^{11}$ is hydrogen or alkyl; $R^{12}$ is —$SO_2R^d$; and $R^{13}$ is hydrogen.

Another specific group of compounds of the invention are compounds wherein $R^{11}$ is —$SO_2R^d$; $R^{12}$ is hydrogen or alkyl; and $R^{13}$ is hydrogen.

When part of the group —$SO_2R^d$, a specific value for $R^d$ is alkyl, aryl, or heteroaryl.

When part of the group —$SO_2R^d$, a specific value for $R^d$ is aryl optionally substituted with 1, 2, 3, or 4 substituents independently selected from halo, $C_{1-6}$alkyl, $C_{1-6}$alkoxy, and —$CF_3$.

When part of the group —$SO_2R^d$, a specific value for $R^d$ is phenyl optionally substituted with 1 or 2 substituents independently selected from halo and $C_{1-6}$alkyl.

A preferred group of compounds of the invention are compounds wherein $R^{11}$ or $R^{12}$ is —$SO_2R^d$; wherein $R^d$ is phenyl, 4-chlorophenyl, methyl, or 4-fluorophenyl.

A specific group of compounds of the invention are compounds wherein at least one of $R^{11}$, $R^{12}$, and $R^{13}$ is —$OR^d$ and each of the other two of $R^{11}$, $R^{12}$, and $R^{13}$ is independently selected from the group consisting of hydrogen, alkyl, —O-alkyl, and halo; wherein any alkyl or —O-alkyl is optionally substituted with aryl, or with one or more (e.g. 1, 2, 3, or 4) halo substituents.

A specific group of compounds of the invention are compounds wherein $R^{11}$ is —$OR^d$.

A specific group of compounds of the invention are compounds wherein $R^{12}$ is —$OR^d$ A specific group of compounds of the invention are compounds wherein $R^{13}$ is —$OR^d$ A specific group of compounds of the invention are compounds wherein $R^{11}$ is hydrogen; $R^{12}$ is —$OR^d$; and $R^{13}$ is hydrogen.

A specific group of compounds of the invention are compounds wherein $R^{11}$ is —$OR^d$; $R^{12}$ is hydrogen; and $R^{13}$ is hydrogen.

When part of the group —$OR^d$, a specific value for $R^d$ is alkyl, optionally substituted with one or more (e.g. 1, 2, 3, or 4) halo substituents and also optionally substituted with 1, 2, 3, or 4 aryl substituents, wherein each aryl is optionally substituted with 1, 2, 3, or 4 substituents independently selected from halo, $C_{1-6}$alkyl, $C_{1-6}$alkoxy, hydroxy, amino, —NH$C_{1-6}$alkyl, —N($C_{1-6}$alkyl$)_2$, —OC(=O)$C_{1-6}$alkyl, —C(=O)$C_{1-6}$alkyl, —C(=O)O$C_{1-6}$alkyl, —NHC(=O)$C_{1-6}$alkyl, —C(=O)NH$C_{1-6}$alkyl, carboxy, nitro, —CN, and —$CF_3$.

When part of the group —$OR^d$, a specific value for $R^d$ is alkyl, optionally substituted with one or more (e.g. 1, 2, 3, or 4) halo substituents and also optionally substituted with 1 or 2 phenyl substituents, wherein each phenyl is optionally substituted with 1 or 2 substituents independently selected from halo, $C_{1-6}$alkyl, $C_{1-6}$alkoxy, hydroxy, —CN, and —$CF_3$.

A specific group of compounds of the invention are compounds wherein $R^{11}$ and $R^{12}$ together with the atoms to which they are attached form a saturated or unsaturated 5, 6, or 7 membered ring comprising one or more carbon atoms and 1 or 2 heteroatoms independently selected from oxygen, sulfur or nitrogen; and $R^{13}$ is selected from the group consisting of hydrogen, alkyl, —O-alkyl, and halo; wherein any alkyl or —O-alkyl is optionally substituted with aryl, or with one or more (e.g. 1, 2, 3, or 4) halo substituents.

A more specific group of compounds of the invention are compounds wherein $R^{11}$ and $R^{12}$ together are —OCH$_2$O—, —OCH$_2$CH$_2$O—, or —OCH$_2$CH$_2$CH$_2$O—.

A specific group of compounds of the invention are compounds wherein $R^{11}$, $R^{12}$, or $R^{13}$ is methoxy, ethoxy, benzyloxy, or isopropoxy.

A specific group of compounds of the invention are compounds wherein $R^{11}$, $R^{12}$, and $R^{13}$ are each hydrogen.

A specific group of compounds of the invention are compounds wherein at least one of $R^{11}$, $R^{12}$, and $R^{13}$ is alkyl and each of the other two of $R^{11}$, $R^{12}$, and $R^{13}$ is independently selected from the group consisting of hydrogen, alkyl, cycloalkyl, hydroxy, and halo, wherein any alkyl is optionally substituted with aryl, with one or more (e.g. 1, 2, 3, or 4) halo, or with 1 or 2 —O-alkyl substituents; or wherein $R^{11}$ and $R^{12}$ together with the atoms to which they are attached form a saturated or unsaturated 5, 6, or 7 membered carbocyclic ring.

A specific group of compounds of the invention are compounds wherein at least one of $R^{11}$, $R^{12}$, and $R^{13}$ is alkyl and each of the other two of $R^{11}$, $R^{12}$, and $R^{13}$ is independently selected from the group consisting of hydrogen, alkyl, cycloalkyl, hydroxy, and halo, wherein any alkyl is optionally substituted with aryl, with one or more (e.g. 1, 2, 3, or 4) halo, or with 1 or 2 —O-alkyl substituents.

A specific group of compounds of the invention are compounds wherein $R^{11}$ and $R^{12}$ together with the atoms to which they are attached form a saturated or unsaturated 5, 6, or 7 membered carbocyclic ring; and $R^{13}$ is selected from the group consisting of hydrogen, alkyl, cycloalkyl, hydroxy, and halo, wherein any alkyl is optionally substituted with aryl, with one or more (e.g. 1, 2, 3, or 4) halo, or with 1 or 2 —O-alkyl substituents.

A specific value for $R^{13}$ is hydrogen.

A specific group of compounds of the invention are compounds wherein $R^{11}$ is hydrogen; $R^{12}$ is alkyl; and $R^{13}$ is hydrogen.

A specific group of compounds of the invention are compounds wherein $R^{11}$ is alkyl; $R^{12}$ is hydrogen; and $R^{13}$ is hydrogen.

A preferred group of compounds of the invention are compounds wherein $R^{11}$ or $R^{12}$ is methyl, ethyl, isopropyl, or cyclohexyl; or wherein $R^{11}$ and $R^{12}$ taken together are —CH$_2$CH$_2$CH$_2$—.

A specific group of compounds of the invention are compounds wherein at least one of $R^{11}$, $R^{12}$, and $R^{13}$ is aryl; and each of the other two of $R^{11}$, $R^{12}$, and $R^{13}$ is independently selected from the group consisting of hydrogen, alkyl, —O-alkyl, and halo, wherein any alkyl or —O-alkyl is optionally substituted with aryl, with one or more (e.g. 1, 2, 3, or 4) halo, or with 1 or 2 —O-alkyl substituents;

or wherein $R^{11}$ and $R^{12}$ together with the atoms to which they are attached form a fused benzo ring, which benzo ring can optionally be substituted with 1, 2, 3, or 4 $R^c$; and $R^{13}$ is independently selected from the group consisting of hydrogen, alkyl, —O-alkyl, and halo, wherein any alkyl or —O-alkyl is optionally substituted with aryl, with one or more (e.g. 1, 2, 3, or 4) halo, or with 1 or 2 —O-alkyl substituents.

A specific group of compounds of the invention are compounds wherein at least one of $R^{11}$, $R^{12}$, and $R^{13}$ is aryl; and each of the other two of $R^{11}$, $R^{12}$, and $R^{13}$ is independently selected from the group consisting of hydrogen, alkyl, —O-alkyl, and halo, wherein any alkyl or —O-alkyl is optionally substituted with aryl, with one or more (e.g. 1, 2, 3, or 4) halo, or with 1 or 2 —O-alkyl substituents.

A specific group of compounds of the invention are compounds wherein $R^{11}$ is phenyl, optionally substituted with 1, 2, 3, or 4 alkyl, —OR$^d$, —NO$_2$, halo, —NR$^d$R$^e$, —C(=O)R$^d$, —CO$_2$R$^d$, —OC(=O)R$^d$, —CN, —C(=O)NR$^d$R$^e$, —NR$^d$C(=O)R$^e$, —OC(=O)NR$^d$R$^e$, —NR$^d$C(=O)OR$^e$, —NR$^d$C(=O)NR$^d$R$^e$, —CR$^d$(=N—OR$^e$), —CF$_3$, or —OCF$_3$; $R^{12}$ is selected from the group consisting of hydrogen and —O-alkyl, optionally substituted with aryl, or with one or more (e.g. 1, 2, 3, or 4) halo; and $R^{13}$ is hydrogen.

A specific group of compounds of the invention are compounds wherein $R^{11}$ is phenyl, optionally substituted with 1, 2, 3, or 4 alkyl, —OR$^d$, halo, —CF$_3$, or —OCF$_3$; $R^{12}$ is selected from the group consisting of hydrogen and —O-alkyl, optionally substituted with aryl, or with one or more (e.g. 1, 2, 3, or 4) halo; and $R^{13}$ is hydrogen.

A specific group of compounds of the invention are compounds wherein $R^{11}$ or $R^{12}$ is phenyl.

A specific group of compounds of the invention are compounds wherein $R^{11}$ and $R^{12}$ together with the atoms to which they are attached form a fused benzo ring.

A specific group of compounds of the invention are compounds wherein at least one of $R^{11}$, $R^{12}$, and $R^{13}$ is heterocyclyl; and each of the other two of $R^{11}$, $R^{12}$, and $R^{13}$ is independently selected from the group consisting of hydrogen, alkyl, —O-alkyl, and halo, wherein any alkyl or —O-alkyl is optionally substituted with aryl, with one or more (e.g. 1, 2, 3, or 4) halo, or with 1 or 2 —O-alkyl substituents;

or wherein $R^{11}$ and $R^{12}$ together with the atoms to which they are attached form a heterocyclic ring.

A specific group of compounds of the invention are compounds wherein $R^{11}$ and $R^{12}$ together with the atoms to which they are attached form a saturated or unsaturated 5, 6, or 7 membered ring comprising carbon atoms and optionally comprising 1 or 2 heteroatoms independently selected from oxygen, sulfur or nitrogen, wherein said ring can optionally be substituted on carbon with one or two oxo (=O), and wherein said ring is fused to a benzo ring, which benzo ring can optionally be substituted with 1, 2, 3, or 4 $R^c$; and $R^{13}$ is independently selected from the group consisting of hydrogen, alkyl, —O-alkyl, and halo, wherein any alkyl or —O-alkyl is optionally substituted with aryl, with one or more halo, or with 1 or 2 —O-alkyl substituents.

A specific group of compounds of the invention are compounds wherein $R^{11}$ or $R^{12}$ is 2,3-dihydro-5-methyl-3-oxo-1-pyrazolyl; or wherein $R^{11}$ and $R^{12}$ together with the atoms to which they are attached form a 2-oxobenzopyran ring.

Another specific group of compounds of the invention are compounds wherein $R^{11}$ or $R^{12}$ is anilino, trifluoromethoxy, or methoxycarbonyl.

A sub-group of compounds of the invention are compounds of formula (I) wherein each of $R^1$-$R^5$ is independently selected from the group consisting of hydrogen, alkyl, and $R^a$; wherein each $R^a$ is independently —OR$^d$, halo, —NR$^d$R$^e$, —NR$^d$C(=O)R$^e$, or —OC(=O)NR$^d$R$^e$;

or $R^1$ and $R^2$, or $R^4$ and $R^5$, are joined together to form a group selected from the group consisting of —C(R$^d$)=C(R$^d$)C(=O)NR$^d$—, —CR$^d$R$^d$—CR$^d$R$^d$—C(=O)NR$^d$—, —NR$^d$C(=O)C(R$^d$)=C(R$^d$)—, —NR$^d$C(=O)CR$^d$R$^d$—CR$^d$R$^d$—, —NR$^d$C(=O)S—, and —SC(=O)NR$^d$—;

$R^6$, $R^8$, and $R^{10}$ are each hydrogen;

each of $R^{11}$ and $R^{12}$ is independently selected from the group consisting of hydrogen, alkyl, cycloalkyl, alkenyl, alkynyl, aryl, heteroaryl, heterocyclyl, —$NO_2$, halo, —$NR^dR^e$, —$CO_2R^d$, —$OC(=O)R^d$, —$CN$, —$C(=O)NR^dR^e$, —$NR^dC(=O)R^e$, —$OR^d$, —$S(O)_mR^d$, —$NR^d$—$NR^d$—$C(=O)R^d$, —$NR^d$—$N=CR^dR^d$, —$N(NR^dR^e)R^d$, and —$S(O)_2NR^dR^e$;

wherein for $R^1$-$R^5$, $R^{11}$, and $R^{12}$, each alkyl is optionally substituted with $R^m$, or with 1, 2, 3, or 4 substituents independently selected from $R^b$; for $R^{11}$ and $R^{12}$, each aryl and heteroaryl is optionally substituted with 1, 2, 3, or 4 substituents independently selected from $R^e$, and for $R^{11}$ and $R^{12}$, each cycloalkyl and heterocyclyl is optionally substituted with 1, 2, 3, or 4 substituents independently selected from $R^b$ and $R^e$;

$R^{13}$ is hydrogen;

the group comprising —$NR^{10}$ is meta or para to the group comprising $R^7$; and w is 0, 1, or 2.

Preferably within the above sub-group of compounds, each of $R^{11}$ and $R^{12}$ is independently selected from the group consisting of hydrogen, alkyl, cycloalkyl, aryl, heterocyclyl, —$OR^d$, —$S(O)_mR^d$, and —$S(O)_2NR^dR^e$; wherein each alkyl is optionally substituted with 1 or 2 substituents independently selected from $R^b$, each aryl is optionally substituted with 1 or 2 substituents independently selected from $R^c$, and each heterocyclyl is optionally substituted with 1 or 2 substituents independently selected from $R^b$ and $R^c$; and m is 0 or 2.

More preferably for such compounds, $R^7$ is hydrogen;

each of $R^{11}$ and $R^{12}$ is independently selected from the group consisting of hydrogen, $C_{1-6}$alkyl, cyclohexyl, phenyl, pyrazolinyl, —$OR^d$, —$S(O)_mR^d$, and —$S(O)_2NR^dR^e$;

w is 0; and $R^d$ and $R^e$ are independently selected from the group consisting of hydrogen, $C_{1-6}$alkyl, phenyl, —$CF_3$, and $C_{1-3}$alkyl, pyridyl, thiazolyl, pyrimidinyl, and pyrazolinyl, where each phenyl is optionally substituted with 1 or 2 substitutents independently selected from halo, —$CF_3$, and $C_{1-3}$alkyl, each pyrimidinyl is optionally substituted with 1 or 2 substitutents independently selected from $C_{1-3}$alkyl and $OC_{1-3}$alkyl, and each pyrazolinyl is optionally substituted with 1 or 2 substitutents independently selected from $C_{1-3}$alkyl and carboxy; or $R^d$ and $R^e$, together with the nitrogen atom to which they are attached are morpholino or piperidino.

Within the more preferred sub-group, one most preferred sub-group of compounds are compounds wherein $R^{11}$ is —$SR^d$ and $R^{12}$ is hydrogen, or $R^{11}$ is hydrogen and $R^{12}$ is —$SR^d$, wherein $R^d$ is selected from the group consisting of $C_{1-3}$alkyl, phenyl, and pyrimidinyl, and wherein each phenyl is optionally substituted with 1 or 2 substitutents independently selected from halo and $C_{1-3}$ alkyl, and each pyrimidinyl is optionally substituted with $C_{1-3}$alkyl.

Another most preferred sub-group of compounds are compounds wherein $R^{11}$ is —$S(O)_2NR^dR^e$ and $R^{12}$ is hydrogen or alkyl, or $R^{11}$ is hydrogen or alkyl and $R^{12}$ is —$S(O)_2NR^dR^e$, wherein $R^d$ and $R^e$ are independently selected from the group consisting of hydrogen, $C_{1-3}$alkyl, phenyl, pyridyl, thiazolyl, and pyrimidinyl, and wherein each phenyl is optionally substituted with 1 substituent selected from halo and $C_{1-3}$ alkyl, and each pyrimidinyl is optionally substituted with 1 substitutent selected from $C_{1-3}$ alkyl and O—$C_{1-3}$ alkyl; or $R^d$ and $R^e$, together with the nitrogen atom to which they are attached are morpholino or piperidino.

Another most preferred sub-group of compounds are compounds wherein $R^{11}$ is —$SO_2R^d$ and $R^{12}$ is hydrogen, or $R^{11}$ is hydrogen and $R^{12}$ is —$SO_2R^d$, wherein $R^d$ is $C_{1-3}$alkyl or phenyl, and wherein each phenyl is optionally substituted with 1 substituent selected from halo and $C_{1-3}$alkyl.

Another most preferred sub-group of compounds are compounds wherein $R^{11}$ is —$OR^d$ and $R^{12}$ is hydrogen or —$OR^d$; or $R^{11}$ is hydrogen and $R^{12}$ is —$OR^d$, wherein $R^d$ is $C_{1-3}$alkyl.

Another most preferred sub-group of compounds are compounds wherein $R^{11}$ is $C_{1-3}$alkyl and $R^{12}$ is hydrogen or $C_{1-3}$alkyl; or $R^{11}$ is cyclohexane and $R^{12}$ is hydroxy.

Another most preferred sub-group of compounds are compounds wherein $R^{11}$ is hydrogen or phenyl; and $R^{12}$ is —$OC_{1-3}$alkyl; or wherein $R^{11}$ is phenyl and $R^{12}$ is hydrogen.

Yet another most preferred sub-group of compounds within the more preferred sub-group defined above are compounds wherein $R^{12}$ is hydrogen and $R^{11}$ is $SO_2NR^dR^e$, wherein $R^d$ and $R^e$, together with the nitrogen atom to which they are attached, are morpholino or piperidino.

Another preferred group of compounds of formula (I) are compounds of formula (IIa):

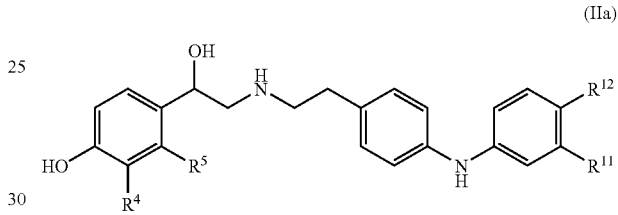

(IIa)

wherein:

$R^4$ is —$CH_2OH$ or —$NHCHO$ and $R^5$ is hydrogen; or $R^4$ and $R^5$ taken together are —$NHC(=O)CH=CH$—;

$R^{11}$ is phenyl or heteroaryl, wherein each phenyl is optionally substituted with 1 or 2 substituents selected from halo, —$OR^d$, —$CN$, —$NO_2$, —$SO_2R^d$, —$C(=O)R^d$, —$C(=O)NR^dR^e$, and $C_{1-3}$alkyl, wherein $C_{1-3}$alkyl is optionally substituted with 1 or 2 substituents selected from carboxy, hydroxy, and amino, and each $R^d$ and $R^e$ is independently hydrogen or $C_{1-3}$alkyl; and wherein each heteroaryl is optionally substituted with 1 or 2 $C_{1-3}$alkyl substituents; and $R^{12}$ is hydrogen or —$OC_{1-6}$alkyl.

More preferably, for compounds of formula (II), $R^{11}$ is phenyl, optionally substituted with 1 or 2 substituents selected from halo, —$OR^d$, —$CN$, —$NO_2$, —$SO_2R^d$, —$C(=O)R^d$, and $C_{1-3}$alkyl, wherein $C_{1-3}$alkyl is optionally substituted with 1 or 2 substituents selected from carboxy, hydroxy, and amino, and $R^d$ is hydrogen or $C_{1-3}$alkyl; or $R^{11}$ is pyridyl, thiophenyl, furanyl, pyrrolyl, isoxazolyl, or indolyl, each of which is optionally substituted with 1 or 2 $C_{1-3}$alkyl substituents.

Most preferable are compounds of formula (IIa), wherein $R^{11}$ is phenyl, pyridyl, or thiophenyl, wherein each phenyl is optionally substituted with 1 substituent selected from the group consisting of chloro, —$OCH_3$, —$CN$, and —$CH_2NH_2$; and $R^{12}$ is hydrogen, —$OCH_3$, or —$OC_2H_5$. Among most preferred compounds, particularly preferred are compounds of formula (II) wherein $R^4$ and $R^5$ taken together are —$NHC(=O)CH=CH$—, $R^{11}$ is phenyl or pyridyl, wherein each phenyl is optionally substituted with 1 substituent selected from the group consisting of chloro, —$OCH_3$, —$CN$, and —$CH_2NH_2$, and $R^{12}$ is —$OCH_3$.

Yet another sub-group of compounds of formula (I) are compounds of formula (IIb):

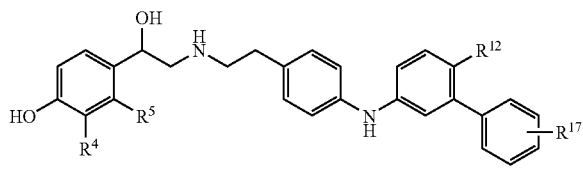

(IIb)

wherein:

$R^4$ is —CH$_2$OH or —NHCHO and $R^5$ is hydrogen; or $R^4$ and $R^5$ taken together are —NHC(=O)CH=CH—;

$R^{12}$ is hydrogen or —OC$_{1-6}$alkyl;

$R^{17}$ is —(CH$_2$)$_x$NR$^d$R$^e$ wherein each R$^d$ and R$^e$ is independently hydrogen or C$_{1-4}$alkyl, wherein each C$_{1-4}$alkyl is optionally substituted with phenyl or pyridyl, or R$^d$ and R$^e$ together with the nitrogen atom to which they are attached is morpholino; and x is 0, 1, or 2.

Preferably, for compounds of formula (IIb), $R^{12}$ is hydrogen, —OCH$_3$, or —OC$_2$H$_5$; and $R^{17}$ is —CH$_2$NR$^d$R$^e$ wherein each R$^d$ and R$^e$ is independently hydrogen or C$_{1-4}$alkyl, or R$^d$ is hydrogen and R$^e$ is C$_{1-4}$alkyl substituted with phenyl or pyridyl, or R$^d$ and R$^e$ together with the nitrogen atom to which they are attached is morpholino. Particularly preferred are compounds of formula (IIb) wherein $R^4$ and $R^5$ taken together are —NHC(=O)CH=CH— and $R^{12}$ and $R^{17}$ are as defined immediately above.

A preferred compound is any one of compounds 1-117 shown in the Examples below.

Most preferred compounds of the invention include the following:

N-{2-[4-(3-phenyl-4-methoxyphenyl)aminophenyl]ethyl}-2-hydroxy-2-(3-hydroxymethyl-4-hydroxyphenyl)ethylamine;

N-{2-[4-(4-ethoxyphenyl)aminophenyl]ethyl}-2-hydroxy-2-(3-hydroxymethyl-4-hydroxyphenyl)ethylamine;

N-{2-[4-(3-phenylphenyl)aminophenyl]ethyl}-2-hydroxy-2-(3-hydroxymethyl-4-hydroxyphenyl)ethylamine;

N-{2-[4-(3-phenyl-4-methoxyphenyl)aminophenyl]ethyl}-2-hydroxy-2-(8-hydroxy-2(1H)-quinolinon-5-yl)ethylamine;

N-{2-[4-(4-methoxyphenyl)aminophenyl]ethyl}-2-hydroxy-2-(3-hydroxymethyl-4-hydroxyphenyl)ethylamine;

N-{2-[4-(3-phenyl-4-ethoxyphenyl)aminophenyl]ethyl}-2-hydroxy-2-(3-hydroxymethyl-4-hydroxyphenyl)ethylamine;

N-{2-[4-(3-phenyl-4-methoxyphenyl)aminophenyl]ethyl}-2-hydroxy-2-(3-formamido-4-hydroxyphenyl)ethylamine;

N-{2-[4-(4-ethoxyphenyl)aminophenyl]ethyl}-2-hydroxy-2-(3-formamido-4-hydroxyphenyl)ethylamine;

N-{2-[4-(3-phenylphenyl)aminophenyl]ethyl}-2-hydroxy-2-(3-formamido-4-hydroxyphenyl)ethylamine;

N-{2-[4-(3-phenyl-4-ethoxyphenyl)aminophenyl]ethyl}-2-hydroxy-2-(3-formamido-4-hydroxyphenyl)ethylamine;

N-{2-[4-(4-methoxyphenyl)aminophenyl]ethyl}-2-hydroxy-2-(3-formamido-4-hydroxyphenyl)ethylamine;

N-{2-[4-(4-ethoxyphenyl)aminophenyl]ethyl}-2-hydroxy-2-(8-hydroxy-2(1H)-quinolinon-5-yl)ethylamine;

N-{2-[4-(3-phenylphenyl)aminophenyl]ethyl}-2-hydroxy-2-(8-hydroxy-2(1H)-quinolinon-5-yl)ethylamine;

N-{2-[4-(3-phenyl-4-ethoxyphenyl)aminophenyl]ethyl}-2-hydroxy-2-(8-hydroxy-2(1H)-quinolinon-5-yl)ethylamine; and N-{2-[4-(4-methoxyphenyl)aminophenyl]ethyl}-2-hydroxy-2-(8-hydroxy-2(1H)-quinolinon-5-yl)ethylamine;

N-{2-[4-(3-phenyl-4-methoxyphenyl)aminophenyl]ethyl}-(R)-2-hydroxy-2-(3-hydroxymethyl-4-hydroxyphenyl)ethylamine;

N-{2-[4-(4-ethoxyphenyl)aminophenyl]ethyl}-(R)-2-hydroxy-2-(3-hydroxymethyl-4-hydroxyphenyl)ethylamine;

N-{2-[4-(3-phenyl)aminophenyl]ethyl}-(R)-2-hydroxy-2-(3-hydroxymethyl-4-hydroxyphenyl)ethylamine;

N-{2-[4-(3-phenyl-4-methoxyphenyl)aminophenyl]ethyl}-(R)-2-hydroxy-2-(8-hydroxy-2(1H)-quinolinon-5-yl)ethylamine;

N-{2-[4-(4-methoxyphenyl)aminophenyl]ethyl}-(R)-2-hydroxy-2-(3-hydroxymethyl-4-hydroxyphenyl)ethylamine;

N-{2-[4-(3-phenyl-4-ethoxyphenyl)aminophenyl]ethyl}-(R)-2-hydroxy-2-(3-hydroxymethyl-4-hydroxyphenyl)ethylamine;

N-{2-[4-(3-phenyl-4-methoxyphenyl)aminophenyl]ethyl}-(R)-2-hydroxy-2-(3-formamido-4-hydroxyphenyl)ethylamine;

N-{2-[4-(4-ethoxyphenyl)aminophenyl]ethyl}-(R)-2-hydroxy-2-(3-formamido-4-hydroxyphenyl)ethylamine;

N-{2-[4-(3-phenylphenyl)aminophenyl]ethyl}-(R)-2-hydroxy-2-(3-formamido-4-hydroxyphenyl)ethylamine;

N-{2-[4-(3-phenyl-4-ethoxyphenyl)aminophenyl]ethyl}-(R)-2-hydroxy-2-(3-formamido-4-hydroxyphenyl)ethylamine;

N-{2-[4-(4-methoxyphenyl)aminophenyl]ethyl}-(R)-2-hydroxy-2-(3-formamido-4-hydroxyphenyl)ethylamine;

N-{2-[4-(4-ethoxyphenyl)aminophenyl]ethyl}-(R)-2-hydroxy-2-(8-hydroxy-2(1H)-quinolinon-5-yl)ethylamine;

N-{2-[4-(3-phenylphenyl)aminophenyl]ethyl}-(R)-2-hydroxy-2-(8-hydroxy-2(1H)-quinolinon-5-yl)ethylamine;

N-{2-[4-(3-phenyl-4-ethoxyphenyl)aminophenyl]ethyl}-(R)-2-hydroxy-2-(8-hydroxy-2(1H)-quinolinon-5-yl)ethylamine;

N-{2-[4-(4-methoxyphenyl)aminophenyl]ethyl}-(R)-2-hydroxy-2-(8-hydroxy-2(1H)-quinolinon-5-yl)ethylamine;

N-{2-[4-(3-(2-chlorophenyl)phenyl)aminophenyl]ethyl}-(R)-2-hydroxy-2-(8-hydroxy-2(1H)-quinolinon-5-yl)ethylamine;

N-{2-[4-(3-(2-methoxyphenyl)phenyl)aminophenyl]ethyl}-(R)-2-hydroxy-2-(8-hydroxy-2(1H)-quinolinon-5-yl)ethylamine;

N-{2-[4-(3-(3-cyanophenyl)phenyl)aminophenyl]ethyl}-(R)-2-hydroxy-2-(8-hydroxy-2(1H)-quinolinon-5-yl)ethylamine;

N-{2-[4-(3-(4-aminomethylphenyl)phenyl)aminophenyl]ethyl}-(R)-2-hydroxy-2-(8-hydroxy-2(1H)-quinolinon-5-yl)ethylamine;

N-{2-[4-(3-(3-chlorophenyl)phenyl)aminophenyl]ethyl}-(R)-2-hydroxy-2-(8-hydroxy-2(1H)-quinolinon-5-yl)ethylamine;

N-{2-[4-(3-(4-aminomethylphenyl)-4-methoxyphenyl)aminophenyl]ethyl}-(R)-2-hydroxy-2-(8-hydroxy-2(1H)-quinolinon-5-yl)ethylamine;

N-{2-[4-(3-(3-cyanophenyl)-4-methoxyphenyl)aminophenyl]ethyl}-(R)-2-hydroxy-2-(8-hydroxy-2(1H)-quinolinon-5-yl)ethylamine;

N-{2-[4-(3-(4-hydroxyphenyl)-4-methoxyphenyl)aminophenyl]ethyl}-(R)-2-hydroxy-2-(8-hydroxy-2(1H)-quinolinon-5-yl)ethylamine;

N-{2-[4-(3-(3-pyridyl)phenyl)aminophenyl]ethyl}-(R)-2-hydroxy-2-(8-hydroxy-2(1H)-quinolinon-5-yl)ethylamine;

N-{2-[4-(3-(3-pyridyl)-4-methoxyphenyl)aminophenyl]ethyl}-(R)-2-hydroxy-2-(8-hydroxy-2(1H)-quinolinon-5-yl)ethylamine;

N-{2-[4-(3-(4-pyridyl)-4-methoxyphenyl)aminophenyl]ethyl}-(R)-2-hydroxy-2-(8-hydroxy-2(1H)-quinolinon-5-yl)ethylamine;

N-{2-[4-(3-(thiophen-3-yl)-4-methoxyphenyl)aminophenyl]ethyl}-(R)-2-hydroxy-2-(8-hydroxy-2(1H)-quinolinon-5-yl)ethylamine;

N-{2-[4-(3-(3-chlorophenyl)-4-methoxyphenyl)aminophenyl]ethyl}-(R)-2-hydroxy-2-(8-hydroxy-2(1H)-quinolinon-5-yl)ethylamine; and N-{2-[4-(3-(3-aminomethylphenyl)-4-methoxyphenyl)aminophenyl]ethyl}-(R)-2-hydroxy-2-(8-hydroxy-2(1H)-quinolinon-5-yl)ethylamine.

Particular mention may be made of the following compounds, for which the compound numbers used in the following examples are indicated in parentheses:

N-{2-[4-(3-phenyl-4-methoxyphenyl)aminophenyl]ethyl}-(R)-2-hydroxy-2-(8-hydroxy-2(1H)-quinolinon-5-yl)ethylamine (61);

N-{2-[4-(3-(4-aminomethylphenyl)-4-methoxyphenyl)aminophenyl]ethyl}-(R)-2-hydroxy-2-(8-hydroxy-2(1H)-quinolinon-5-yl)ethylamine (96);

N-{2-[4-(3-(3-cyanophenyl)-4-methoxyphenyl)aminophenyl]ethyl}-(R)-2-hydroxy-2-(8-hydroxy-2(1H)-quinolinon-5-yl)ethylamine (95);

N-{2-[4-(3-(3-chlorophenyl)-4-methoxyphenyl)aminophenyl]ethyl}-(R)-2-hydroxy-2-(8-hydroxy-2(1H)-quinolinon-5-yl)ethylamine (102); and N-{2-[4-(3-(3-aminomethylphenyl)-4-methoxyphenyl)aminophenyl]ethyl}-(R)-2-hydroxy-2-(8-hydroxy-2(1H)-quinolinon-5-yl)ethylamine (112).

A consistent chemical nomenclature is employed throughout this application. In an alternative nomenclature, using the automatic naming program AutoNom, as provided by MDL Information Systems, GmbH (Frankfurt, Germany), compound 61, for example, is referenced as 8-hydroxy-5-((R)-1-hydroxy-2-{2-[4-(6-methoxy-biphenyl-3-ylamino)-phenyl]-ethylamino}-ethyl)-1H-quinolin-2-one.

As described throughout, the invention also includes pharmaceutically-acceptable salts of the compounds of the invention. A preferred pharmaceutically-acceptable salt of compound 61 is the hydrochloride salt.

The compounds of the invention contain one or more chiral centers Accordingly, the invention includes racemic mixtures, pure stereoisomers (i.e. individual enantiomers or diastereomers), and stereoisomer-enriched mixtures of such isomers, unless otherwise indicated. When a particular stereoisomer is shown, it will be understood by those skilled in the art, that minor amounts of other stereoisomers may be present in the compositions of this invention unless otherwise indicated, provided that the utility of the composition as a whole is not eliminated by the presence of such other isomers. In particular, compounds of the invention contain a chiral center at the alkylene carbon in formulas (I) and (II) to which the hydroxy group is attached. When a mixture of stereoisomers is employed, it is advantageous for the amount of the stereoisomer with the (R) orientation at the chiral center bearing the hydroxy group to be greater than the amount of the corresponding (S) stereoisomer. When comparing stereoisomers of the same compound, the (R) stereoisomer is preferred over the (S) stereoisomer.

General Synthetic Procedures

The compounds of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be used to prevent certain functional groups from undergoing undesired reactions. The choice of a suitable protecting group for a particular functional group, as well as suitable conditions for protection and deprotection, are well known in the art. Representative examples of amino-protecting groups and hydroxy-protecting groups are given above. Typical procedures for their removal include the following. An acyl amino-protecting group or hydroxy-protecting group may conveniently be removed, for example, by treatment with an acid, such as trifluoroacetic acid. An arylmethyl group may conveniently be removed by hydrogenolysis over a suitable metal catalyst such as palladium on carbon. A silyl hydroxy-protecting group may conveniently be removed by treatment with a fluoride ion source, such as tetrabutylammonium fluoride, or by treatment with an acid, such as hydrochloric acid.

In addition, numerous protecting groups (including amino-protecting groups and hydroxy-protecting groups), and their introduction and removal, are described in Greene and Wuts, *Protecting Groups in Organic Synthesis*, 2nd Edition, John Wiley & Sons, NY, 1991, and in McOmie, *Protecting Groups in Organic Chemistry*, Plenum Press, NY, 1973.

Processes for preparing compounds of the invention are provided as further embodiments of the invention and are illustrated by the procedures below.

A compound of formula (I) can be prepared by deprotecting a corresponding compound of formula (III):

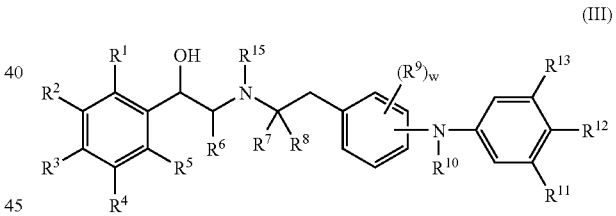

(III)

wherein $R^{15}$ is an amino-protecting group. Accordingly, the invention provides a method for preparing a compound of formula (I), comprising deprotecting a corresponding compound of formula (II), wherein $R^{15}$ is an amino-protecting group (e.g. 1,1-(4-methoxyphenyl)methyl or benzyl).

A compound of formula (I) wherein $R^3$ is hydroxy can be prepared by deprotecting a corresponding compound of formula (I) wherein $R^3$ is —$OPg^1$ and $Pg^1$ is a hydroxy-protecting group. Accordingly, the invention provides a method for preparing a compound of formula (I) wherein $R^3$ is hydroxy, comprising deprotecting a corresponding compound of formula (I) wherein $R^3$ is —$OPg^1$ and $Pg^1$ is a hydroxy-protecting group (e.g. benzyl).

A compound of formula (I) wherein $R^3$ is hydroxy can also be prepared by deprotecting a corresponding compound of formula (III) wherein $R^{15}$ is an amino-protecting group and wherein $R^3$ is —$OPg^1$ wherein $Pg^1$ is a hydroxy-protecting group. Accordingly, the invention provides a method for preparing a compound of formula (I), comprising deprotecting a corresponding compound of formula (III) wherein $R^{15}$ is an amino-protecting group (e.g. benzyl) and $R^3$ is —$OPg^1$ wherein $Pg^1$ is a hydroxy-protecting group (e.g. benzyl).

The invention also provides an intermediate compound of formula (III) wherein $R^{15}$ is an amino-protecting group (e.g. 1,1-di-(4'-methoxyphenyl)methyl or benzyl); as well as an intermediate compound of formula (I) wherein $R^3$ is —$OPg^1$ and $Pg^1$ is a hydroxy-protecting group; and an intermediate compound of formula (III) wherein $R^{15}$ is an amino-protecting group (e.g. benzyl), $R^3$ is —$OPg^1$, and $Pg^1$ is a hydroxy-protecting group (e.g. benzyl).

An intermediate compound of formula (If) can be prepared by reacting an amine of formula (V) with a compound of formula (IV), wherein $R^{16}$ is hydrogen or a hydroxy-protecting group (e.g. tert-butyldimethylsilyl) and X is a suitable leaving group (e.g. bromo).

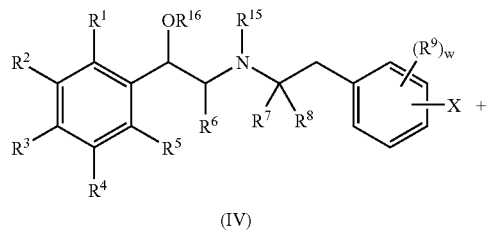

(IV)

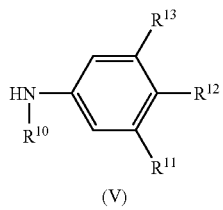

(V)

Accordingly, the invention provides a method for preparing a compound of formula (III), comprising reacting a corresponding aniline of formula (V) with a corresponding compound of formula (IV), wherein X is a suitable leaving group (e.g. bromo) and $R^{15}$ is an amino-protecting group, in the presence of a transition metal catalyst. When $R^{16}$ is a hydroxy-protecting group, the intermediate formed by the reaction of a compound of formula (V) with a compound of formula (IV) is subsequently deprotected to form the intermediate of formula (III). Suitable conditions for this reaction as well as suitable leaving groups are illustrated in the Examples and are also known in the art.

A compound of formula (III) can also be prepared by reacting an amine of formula (VII):

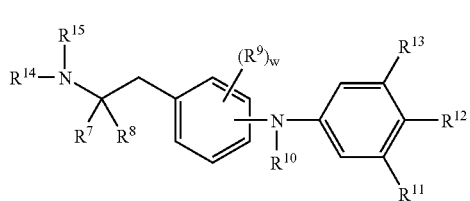

(VII)

wherein $R^{14}$ is hydrogen and $R^{15}$ is an amino-protecting group (e.g. benzyl), with a compound of formula (VI), (VIII), or (IX):

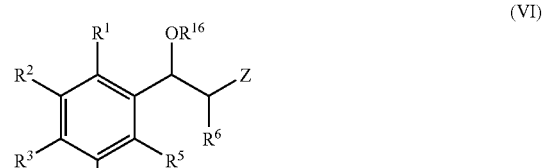

(VI)

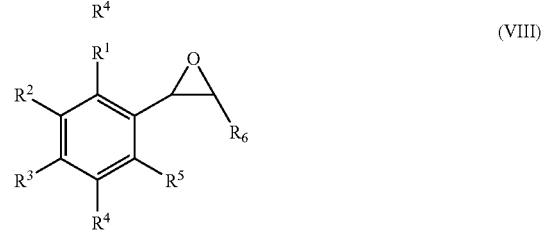

(VIII)

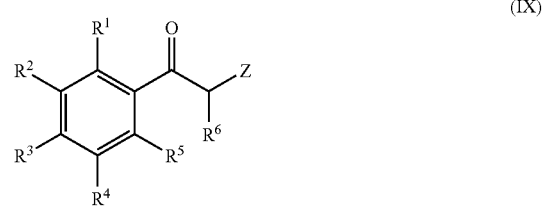

(IX)

wherein $R^{16}$ is hydrogen or a hydroxy-protecting group (e.g. tert-butyldimethylsilyl) and Z is a leaving group.

Accordingly, the invention provides a method for preparing a compound of formula (III), comprising reacting a corresponding amine of formula (VII), wherein $R^{14}$ is hydrogen and $R^{15}$ is an amino-protecting group, with a corresponding compound of formula (VI), (VIII), or (IX), wherein $R^{16}$ is hydrogen or a hydroxy-protecting group and Z is a suitable leaving group (e.g. bromo). When $R^{16}$ is a hydroxy-protecting group, the intermediate formed by the reaction of a compound of formula (VII) with a compound of formula (VI) is subsequently deprotected to form the intermediate of formula (III).

The invention also provides a method for preparing a compound of formula (I), wherein $R^3$ is —$OPg^1$ and $Pg^1$ is a hydroxy-protecting group, comprising reacting a corresponding compound of formula (VII) wherein $R^{14}$ and $R^{15}$ are each hydrogen with a corresponding compound of formula (VI), wherein $R^3$ is —$OPg^1$ and $Pg^1$ is a hydroxy-protecting group and $R^{16}$ is a hydroxy-protecting group.

Depending on the specific values of the substituents, variations on the synthetic schemes described above can be employed, particularly in the order of coupling and deprotection reactions, to produce a compound of the invention. For example, a compound of formula (I) wherein $R^3$ is hydroxy and $R^{13}$ is hydrogen can be prepared by reacting an intermediate of formula (I) wherein $R^3$ is —$OPg^1$, where $Pg^1$ is a hydroxy-protecting group, and $R^{11}$ is a suitable leaving group (e.g. bromo) with an appropriately substituted boronic acid to form an intermediate, which is subsequently deprotected, as illustrated in Examples 65-102.

According to yet another method, a compound of formula (I) can be prepared by coupling an intermediate of formula (IV) wherein $R^{15}$ is hydrogen and $R^{16}$ is a hydroxy-protecting group with a compound of formula (V), where the remaining variables are defined as in formula (I), in the presence of a transition metal catalyst, typically palladium, to form a protected intermediate, followed by removing the protecting group $R^{16}$ to form a compound of formula (I).

To form a compound of formula (I) wherein $R^3$ is hydroxy, a compound of formula (IV) wherein $R^3$ is —$OPg^1$ and $Pg^1$ is a hydroxy-protecting group, for example benzyl, is used in the above method to provide an intermediate of formula (I) in which $R^3$ is —$OPg^1$, from which the protecting group $Pg^1$ is removed to form the product of formula (I) having a hydroxy at $R^3$.

A palladium-based catalyst is typically used in the process of coupling intermediates (IV) and (V) to provide a diarylamine compound of formula (I). As a result the compounds of this invention or intermediates thereof can be contaminated with unacceptable levels of palladium impurities. It has now been discovered that such palladium impurities can be removed from compounds of this invention or intermediates thereof using a functionalized solid support comprising (1-thioureido)alkyl or (mercapto)alkyl groups.

The compound to be purified of palladium is dissolved in a solvent compatible with the solid support, where a compatible solvent is one that does not affect the performance of the functionalized solid support. If the compound is in a free base form, an amount of acid, preferably hydrochloric acid, sufficient to convert the basic nitrogens of the compound to protonated form is added. Between about 1.05 and about 1.2 equivalents of HCl per basic nitrogen is a sufficient amount. The resulting solution is diluted further with solvent and a functionalized solid support comprising (1-thioureido)alkyl or (mercapto)alkyl groups is added. Preferably the solid support is a silica gel comprising 3-(1-thioureido)propyl or 3-(mercapto)propyl groups. Preferably between about 5 and about 15 weight % of the functionalized silica gel is added. A preferred solvent compatible with the functionalized silica gel is a mixture of dichloromethane and methanol.

The resulting solution is separated from the solid support and the product is isolated. For example, the solution is stirred at room temperature for several hours followed by filtration through filter paper. The remaining silica is washed with additional solvent. Combined filtrates are washed with saturated aqueous sodium bicarbonate and brine. The organic solution is treated with anhydrous sodium sulfate, filtered and evaporated under reduced pressure to give the product. The purification of an intermediate in the preparation of compound 61 by this process is described in detail in Example 61C part f.

Accordingly, in yet another method aspect, this invention provides a method of reducing the amount of palladium in a composition comprising a diarylamine compound and palladium, the method comprising (a) contacting a solution comprising a diarylamine compound having one or more basic nitrogen atoms wherein each nitrogen atom has been protonated with an acid, palladium, and a solvent, with a functionalized solid support comprising (1-thioureido)alkyl or (mercapto)alkyl groups; and (b) separating the resulting solution from the solid support to provide a composition having a reduced amount of palladium, wherein the solvent is compatible with the functionalized solid support. In addition, the invention provides a method of reducing palladium in a composition wherein the diarylamine compound is N-{2-[4-(3-phenyl-4-methoxyphenyl)aminophenyl]ethyl}-(R)-2-hydroxy-2-(8-benzyloxy-2(1H)-quinolinon-5-yl)ethylamine. Preferably, in the method of removing palladium from the diarylamine compound immediately above, the acid is hydrochloric acid; the solvent comprises a mixture of dichloromethane and methanol, and the functionalized solid support is a silica gel comprising 3-(1-thioureido)propyl or 3-(mercapto)propyl groups.

The invention further provides a compound produced by the process comprising (a) coupling an intermediate of formula (IV) wherein $R^{15}$ is hydrogen and $R^{16}$ is a hydroxy-protecting group with a compound of formula (V), where the remaining variables are defined as in formula (I) and $R^3$ can additionally be defined as —$OPg^1$, in the presence of a palladium catalyst, to form a protected intermediate; (b) removing the protecting group $R^{16}$ from the protected intermediate to form a compound of formula (I); (c) contacting a solution comprising the compound of formula (I), wherein each nitrogen atom has been protonated with an acid, and a solvent, with a functionalized solid support comprising (1-thioureido)alkyl or 3-(mercapto)alkyl groups, wherein the solvent is compatible with the functionalized solid support; (d) separating the resulting solution from the functionalized solid support; and, when $R^3$ is —$OPg^1$, (d) removing the protecting group to form a compound in which $R^3$ is hydroxy.

In addition, the invention provides a compound produced by the process immediately above wherein $R^1$, $R^2$, $R^6$, $R^7$, $R^8$, $R^9$, $R^{10}$, and $R^{13}$ are each hydrogen, $R^3$ is —$OPg^1$ wherein $Pg^1$ is benzyl, $R^4$ and $R^5$ taken together are —NHC(=O)CH=CH—, $R^{11}$ is phenyl, $R^{12}$ is —$OCH_3$, the leaving group X in formula (IV) is attached at the para position; the acid is hydrochloric acid; the solvent is a mixture of dichloromethane and methanol, and the functionalized solid support is a silica gel comprising 3-(1-thioureido)propyl or 3-(mercapto)propyl groups.

Additionally, a useful intermediate for preparing a compound of formula (VII), wherein $R^{14}$ is hydrogen and $R^{15}$ is an amino-protecting group, is a corresponding compound of formula (VII) wherein $R^{14}$ is an amino-protecting group that can be removed in the presence of $R^{15}$. A compound of formula (VII) wherein $R^{14}$ is hydrogen and $R^{15}$ is an amino-protecting group is itself also a useful intermediate for the preparation of a compound of formula (VII) where both $R^{14}$ and $R^{15}$ are hydrogen. Thus, the invention also provides novel intermediates of formula (VII), wherein $R^{14}$ is hydrogen or an amino-protecting group, $R^{15}$ is hydrogen or an amino-protecting group, and wherein $R^7$-$R^{13}$ and w have any of the values defined herein, or a salt thereof.

A preferred compound of formula (VII) is a compound wherein $R^{14}$ and $R^{15}$ are both hydrogen. Another preferred compound of formula (VII) is a compound wherein $R^{14}$ is an alkoxycarbonyl protecting group (e.g. tert-butoxy carbonyl), and $R^{15}$ is an arylmethyl protecting group (e.g. benzyl). Another preferred compound of formula (VII) is a compound wherein $R^{14}$ is hydrogen, and $R^{15}$ is an alkoxycarbonyl protecting group (e.g. tert-butoxy carbonyl).

Pharmaceutical Compositions

The invention also provides pharmaceutical compositions comprising a compound of the invention. Accordingly, the compound, preferably in the form of a pharmaceutically-acceptable salt, can be formulated for any suitable form of administration, such as oral or parenteral administration, or administration by inhalation.

By way of illustration, the compound can be admixed with conventional pharmaceutical carriers and excipients and used in the form of powders, tablets, capsules, elixirs, suspensions, syrups, wafers, and the like. Such pharmaceutical compositions will contain from about 0.05 to about 90% by weight of the active compound, and more generally from about 0.1 to about 30%. The pharmaceutical compositions may contain common carriers and excipients, such as cornstarch or gelatin, lactose, magnesium sulfate, magnesium stearate, sucrose, microcrystalline cellulose, kaolin, mannitol, dicalcium phosphate, sodium chloride, and alginic acid. Disintegrators commonly used in the formulations of this invention include croscarmellose, microcrystalline cellulose, cornstarch, sodium starch glycolate and alginic acid.

A liquid composition will generally consist of a suspension or solution of the compound or pharmaceutically-acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically-acceptable salts that are active when given parenterally can be formulated for intramuscular, intrathecal, or intravenous administration.

A typical composition for intra-muscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetracetic acid; a solubilizing agent, for example, a cyclodextrin; and an antioxidant, for example, sodium metabisulphite, may be included in the formulation. Alternatively, the solution can be freeze dried and then reconstituted with a suitable solvent just prior to administration.

The compounds of this invention and their pharmaceutically-acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252. Such patches may be constructed for continuous, pulsatile, or on demand delivery of pharmaceutical agents.

One preferred manner for administering a compound of the invention is inhalation. Inhalation is an effective means for delivering an agent directly to the respiratory tract. There are three general types of pharmaceutical inhalation devices: nebulizer inhalers, dry powder inhalers (DPI), and metered-dose inhalers (MDI). Nebulizer devices produce a stream of high velocity air that causes a therapeutic agent to spray as a mist which is carried into the patient's respiratory tract. The therapeutic agent is formulated in a liquid form such as a solution or a suspension of micronized particles of respirable size, where micronized is typically defined as having about 90% or more of the particles with a diameter of less than about 10 μm. A typical formulation for use in a conventional nebulizer device is an isotonic aqueous solution of a pharmaceutical salt of the active agent at a concentration of the active agent of between about 0.05 μg/mL and about 10 mg/mL.

DPI's typically administer a therapeutic agent in the form of a free flowing powder that can be dispersed in a patient's air-stream during inspiration. In order to achieve a free flowing powder, the therapeutic agent can be formulated with a suitable excipient, such as lactose or starch. A dry powder formulation can be made, for example, by combining dry lactose having a particle size between about 1 μm and about 100 μm with micronized particles of a pharmaceutical salt of the active agent and dry blending. Alternative, the agent can be formulated without excipients. The formulation is loaded into a dry powder dispenser, or into inhalation cartridges or capsules for use with a dry powder delivery device.

Examples of DPI delivery devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI's typically discharge a measured amount of therapeutic agent using compressed propellant gas. Formulations for MDI administration include a solution or suspension of active ingredient in a liquefied propellant. While chlorofluorocarbons, such as $CCl_3F$, conventionally have been used as propellants, due to concerns regarding adverse affects of such agents on the ozone layer, formulations using hydrofluoroalkanes (HFA), such as 1,1,1,2-tetrafluoroethane (HFA 134a) and 1,1,1,2,3,3,3,-heptafluoro-n-propane, (HFA 227) have been developed. Additional components of HFA formulations for MDI administration include co-solvents, such as ethanol or pentane, and surfactants, such as sorbitan trioleate, oleic acid, lecithin, and glycerin. (See, for example, U.S. Pat. No. 5,225,183, EP 0717987 A2, and WO 92/22286.)

Thus, a suitable formulation for MDI administration can include from about 0.01% to about 5% by weight of a pharmaceutical salt of active ingredient, from about 0% to about 20% by weight ethanol, and from about 0% to about 5% by weight surfactant, with the remainder being the HFA propellant. In one approach, to prepare the formulation, chilled or pressurized hydrofluoroalkane is added to a vial containing the pharmaceutical salt of active compound, ethanol (if present) and the surfactant (if present). To prepare a suspension, the pharmaceutical salt is provided as micronized particles. The formulation is loaded into an aerosol canister, which forms a portion of an MDI device. Examples of MDI devices developed specifically for use with HFA propellants are provided in U.S. Pat. Nos. 6,006,745 and 6,143,277.

In an alternative preparation, a suspension formulation is prepared by spray drying a coating of surfactant on micronized particles of a pharmaceutical salt of active compound. (See, for example, WO 99/53901 and WO 00/61108.) For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

It will be understood that any form of the compounds of the invention, (i.e. free base, pharmaceutical salt, or solvate) that is suitable for the particular mode of administration, can be used in the pharmaceutical compositions discussed above.

The active compounds are effective over a wide dosage range and are generally administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses of the therapeutic agents for inhalation administration are in the general range of from about 0.05 μg/day to about 1000 μg/day, preferably from about 0.5 μg/day to about 500 μg/day. A compound can be administered in a periodic dose: weekly, multiple times per week, daily, or multiple doses per day. The treatment regimen may require administration over extended periods of time, for example, for several weeks or months, or the treatment regimen may require chronic administration. Suitable doses for oral administration are in the general range of from about 0.05 μg/day to about 100 mg/day, preferably 0.5 to 1000 μg/day.

The present active agents can also be co-administered with one or more other therapeutic agents. For example, the present agents can be administered in combination with one or more therapeutic agents selected from anti-inflammatory agents (e.g. corticosteroids and non-steroidal anti-inflammatory agents (NSAIDs), antichlolinergic agents (particularly muscarinic receptor antagonists), other $\beta_2$ adrenergic receptor agonists, antiinfective agents (e.g. antibiotics or antivirals) or antihistamines. The invention thus provides, in a further aspect, a combination comprising a compound of the invention together with one or more therapeutic agent, for example, an anti-inflammatory agent, an antichlolinergic agent, another $\beta_2$ adrenergic receptor agonist, an antiinfective agent or an antihistamine.

The other therapeutic agents can be used in the form of pharmaceutically acceptable salts or solvates. As appropriate, the other therapeutic agents can be used as optically pure stereoisomers.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1, 4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (αIL antibody), specifically, an αIL-4 therapy, an αIL-13 therapy, or a combination thereof); or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Also of interest is use of the present active agent in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$ ratios is set out in U.S. Pat. No. 5,998,428 which is incorporated herein by reference. See also PCT application WO 00/51599 for another description of the assay.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is one wherein the PDE4 inhibitor has an $IC_{50}$ ratio of about 0.1 or greater; wherein said ratio is the ratio of the $IC_{50}$ value for competing with the binding of 1 nM of [$^3$H]R-rolipram to a form of PDE4 which binds rolipram with a high affinity to the $IC_{50}$ value for inhibiting the PDE4 catalytic activity of a form which binds rolipram with a low affinity using 1 μM[$^3$H]-cAMP as the substrate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other compounds of interest include:

Compounds set out in U.S. Pat. No. 5,552,438 issued 3 Sep., 1996; this patent and the compounds it discloses are incorporated herein in full by reference. The compound of particular interest, which is disclosed in U.S. Pat. No. 5,552, 438, is cis-4-cyano-4-[3-(cyclopentyloxy)-4-methoxyphenyl]cyclohexane-1-carboxylic acid (also known as cilomalast) and its salts, esters, pro-drugs or physical forms;

AWD-12-281 from elbion (Hofgen, N. et al. 15th EFMC Int Symp Med Chem (Sep. 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (–)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$, $M_2$, or $M_3$ receptors, or of combinations thereof. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, are characterized, based on their core structures, as ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic a tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a compound of the invention.

Examples of preferred anti-histamines include methapyrilene and loratadine.

The invention thus provides, in a further aspect, a combination comprising a compound of formula (I) or a pharmaceutically acceptable salt or solvate or stereoisomer thereof and a corticosteroid. In particular, the invention provides a combination wherein the corticosteroid is fluticasone propionate or wherein the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester or 6α,9α-difluoro-11β-hydroxy-16α-methyl-3-oxo- 17α-propionyloxy-androsta-1,4-diene-17β-carbothioic acid S-(2-oxo-tetrahydro-furan-3S-yl) ester.

The invention thus provides, in a further aspect, a combination comprising a compound of formula (I) or a pharmaceutically acceptable salt or solvate or stereoisomer thereof and a PDE4 inhibitor.

The invention thus provides, in a further aspect, a combination comprising a compound of formula (I) or a pharmaceutically acceptable salt or solvate or stereoisomer thereof and an anticholinergic agent.

The invention thus provides, in a further aspect, a combination comprising a compound of formula (I) or a pharmaceutically acceptable salt or solvate or stereoisomer thereof and an antihistamine.

The invention thus provides, in a further aspect, a combination comprising a compound of formula (I) or a pharmaceutically acceptable salt or solvate or stereoisomer thereof together with a PDE4 inhibitor and a corticosteroid.

The invention thus provides, in a further aspect, a combination comprising a compound of formula (I) or a pharmaceutically acceptable salt or solvate or stereoisomer thereof together with an anticholinergic agent and a corticosteroid.

As used in the above combinations, the term, "a compound of formula (I)" includes a compound of the preferred, more preferred, or most preferred subgroup of compounds of formula (I), including a compound of formula (IIa) or (IIb) and subgroups thereof, and any individually disclosed compound or compounds.

Accordingly, the pharmaceutical compositions of the invention can optionally comprise combinations of a compound of formula (I) or a pharmaceutically acceptable salt or solvate or stereoisomer thereof with one or more other therapeutic agents, as described above.

The individual compounds of such combinations may be administered either sequentially or simultaneously in separate or combined pharmaceutical formulations. Appropriate doses of known therapeutic agents will be readily appreciated by those skilled in the art.

According to a further aspect, the invention provides a method of treating a disease or condition associated with $\beta_2$ adrenergic receptor activity in a mammal, comprising administering to the mammal a therapeutically effective amount of a combination of a compound of formula (I) or a pharmaceutically acceptable salt or solvate or stereoisomer thereof with one or more other therapeutic agents.

Additional suitable carriers for formulations of the active compounds of the present invention can be found in *Remington: The Science and Practice of Pharmacy*, 20*th Edition*, Lippincott Williams & Wilkins, Philadelphia, Pa., 2000. The following non-limiting examples illustrate representative pharmaceutical compositions of the invention.

FORMULATION EXAMPLE A

This example illustrates the preparation of a representative pharmaceutical composition for oral administration of a compound of this invention:

| Ingredients | Quantity per tablet, (mg) |
|---|---|
| Active Compound | 2 |
| Lactose, spray-dried | 148 |
| Magnesium stearate | 2 |

The above ingredients are mixed and introduced into a hard-shell gelatin capsule.

FORMULATION EXAMPLE B

This example illustrates the preparation of another representative pharmaceutical composition for oral administration of a compound of this invention:

| Ingredients | Quantity per tablet, (mg) |
|---|---|
| Active Compound | 4 |
| Cornstarch | 50 |
| Lactose | 145 |
| Magnesium stearate | 5 |

The above ingredients are mixed intimately and pressed into single scored tablets.

FORMULATION EXAMPLE C

This example illustrates the preparation of a representative pharmaceutical composition for oral administration of a compound of this invention.

An oral suspension is prepared having the following composition.

| Ingredients | |
|---|---|
| Active Compound | 0.1 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

FORMULATION EXAMPLE D

This example illustrates the preparation of a representative pharmaceutical composition containing a compound of this invention.

An injectable preparation buffered to a pH of 4 is prepared having the following composition:

| Ingredients | |
|---|---|
| Active Compound | 0.2 g |
| Sodium Acetate Buffer Solution (0.4 M) | 2.0 mL |
| HCl (1N) | q.s. to pH 4 |
| Water (distilled, sterile) | q.s. to 20 mL |

FORMULATION EXAMPLE E

This example illustrates the preparation of a representative pharmaceutical composition for injection of a compound of this invention.

A reconstituted solution is prepared by adding 20 mL of sterile water to 1 g of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

FORMULATION EXAMPLE F

This example illustrates the preparation of a representative pharmaceutical composition containing a compound of this invention.

An injectable preparation is prepared having the following composition:

| Ingredients | |
| --- | --- |
| Active Compound | 0.1-5.0 g |
| Hydroxypropyl-β-cyclodextrin | 1-25 g |
| 5% Aqueous Dextrose Solution (sterile) | q.s. to 100 mL |

The above ingredients are blended and the pH is adjusted to 3.5±0.5 using 0.5 N HCl or 0.5 N NaOH.

FORMULATION EXAMPLE G

This example illustrates the preparation of a representative pharmaceutical composition for topical application of a compound of this invention.

| Ingredients | grams |
| --- | --- |
| Active compound | 0.2-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

FORMULATION EXAMPLE H

This example illustrates the preparation of a representative pharmaceutical composition containing a compound of the invention.

An aqueous aerosol formulation for use in a nebulizer is prepared by dissolving 0.1 mg of a pharmaceutical salt of active compound in a 0.9% sodium chloride solution acidified with citric acid. The mixture is stirred and sonicated until the active salt is dissolved. The pH of the solution is adjusted to a value in the range of from 3 to 8 by the slow addition of NaOH.

FORMULATION EXAMPLE I

This example illustrates the preparation of a dry powder formulation containing a compound of the invention for use in inhalation cartridges.

Gelatin inhalation cartridges are filled with a pharmaceutical composition having the following ingredients:

| Ingredients | mg/cartridge |
|---|---|
| Pharmaceutical salt of active compound | 0.2 |
| Lactose | 25 |

The pharmaceutical salt of active compound is micronized prior to blending with lactose. The contents of the cartridges are administered using a powder inhaler.

FORMULATION EXAMPLE J

This example illustrates the preparation of a dry powder formulation containing a compound of the invention for use in a dry powder inhalation device.

A pharmaceutical composition is prepared having a bulk formulation ratio of micronized pharmaceutical salt to lactose of 1:200. The composition is packed into a dry powder inhalation device capable of delivering between about 10 μg and about 100 μg of active drug ingredient per dose.

FORMULATION EXAMPLE K

This example illustrates the preparation of a formulation containing a compound of the invention for use in a metered dose inhaler.

A suspension containing 5% pharmaceutical salt of active compound, 0.5% lecithin, and 0.5% trehalose is prepared by dispersing 5 g of active compound as micronized particles with mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

FORMULATION EXAMPLE L

This example illustrates the preparation of a formulation containing a compound of the invention for use in a metered dose inhaler.

A suspension containing 5% pharmaceutical salt of active compound and 0.1% lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into canisters with pressurized 1,1,1,2,3,3,3-heptafluoro-n-propane.

Biological Assays

The compounds of this invention, and their pharmaceutically-acceptable salts, exhibit biological activity and are useful for medical treatment. The ability of a compound to bind to the $\beta_2$ adrenergic receptor, as well as its selectivity, agonist potency, and intrinsic activity can be demonstrated using in vitro Tests A-C below, in vivo Test D, below, or can be demonstrated using other tests that are known in the art.

| Abbreviations | |
|---|---|
| % Eff | % efficacy |
| ATCC | American Type Culture Collection |
| BSA | Bovine Serum Albumin |
| cAMP | Adenosine 3':5'-cyclic monophosphate |
| DMEM | Dulbecco's Modified Eagle's Medium |
| DMSO | Dimethyl sulfoxide |
| EDTA | Ethylenediaminetetraacetic acid |
| Emax | maximal efficacy |
| FBS | Fetal bovine serum |
| Gly | Glycine |
| HEK-293 | Human embryonic kidney - 293 |
| PBS | Phosphate buffered saline |
| rpm | rotations per minute |
| Tris | Tris(hydroxymethyl)aminomethane |

Membrane Preparation From Cells Expressing Human $\beta_1$ or $\beta_2$ Adrenergic Receptors HEK-293 derived cell lines stably expressing cloned human $\beta_1$ or $\beta_2$ adrenergic receptors, respectively, were grown to near confluency in DMEM with 10% dialyzed FBS in the presence of 500 µg/mL Geneticin. The cell monolayer was lifted with Versene 1:5,000 (0.2 g/L EDTA in PBS) using a cell scraper. Cells were pelleted by centrifugation at 1,000 rpm, and cell pellets were either stored frozen at −80° C. or membranes were prepared immediately. For preparation, cell pellets were resuspended in lysis buffer (10 mM Tris/HCL pH 7.4 @ 4° C., one tablet of "Complete Protease Inhibitor Cocktail Tablets with 2 mM EDTA" per 50 mL buffer (Roche cat.# 1697498, Roche Molecular Biochemicals, Indianapolis, Ind.)) and homogenized using a tight-fitting Dounce glass homogenizer (20 strokes) on ice. The homogenate was centrifuged at 20,000×g, the pellet washed once with lysis buffer by resuspension and centrifugation as above. The final pellet was resuspended in membrane buffer (75 mM Tris/HCl pH 7.4, 12.5 mM MgCl$_2$, 1 mM EDTA @ 25° C.). Protein concentration of the membrane suspension was determined by the method of Bradford (Bradford M M., *Analytical Biochemistry*, 1976, 72, 248-54). Membranes were stored frozen in aliquots at −80° C.

Test A

Radioligand Binding Assay on Human $\beta_1$ and $\beta_2$ Adrenergic Receptors

Binding assays were performed in 96-well microtiter plates in a total assay volume of 100 µL with 5 µg membrane protein for membranes containing the human $\beta_2$ adrenergic receptor, or 2.5 µg membrane protein for membranes containing the human $\beta_1$ adrenergic receptor in assay buffer (75 mM Tris/HCl pH 7.4 @ 25° C., 12.5 mM MgCl$_2$, 1 mM EDTA, 0.2% BSA). Saturation binding studies for determination of K$_d$ values of the radioligand were done using [$^3$H]dihydroalprenolol (NET-720, 100 Ci/mmol, PerkinElmer Life Sciences Inc., Boston, Mass.) at 10 different concentrations ranging from 0.01 nM-200 nM. Displacement assays for determination of pK$_i$ values of compounds were done with [$^3$H]dihydroalprenolol at 1 nM and 10 different concentrations of compound ranging from 40 pM-10 µM. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer. Non-specific binding was determined in the presence of 10 µM unlabeled alprenolol. Assays were incubated for 90 minutes at room temperature, binding reactions were terminated by rapid filtration over GF/B glass fiber filter plates (Packard BioScience Co., Meriden, Conn.) presoaked in 0.3% polyethyleneimine. Filter plates were washed three times with filtration buffer (75 mM Tris/HCl pH 7.4 @ 4° C., 12.5 mM MgCl$_2$, 1 mM EDTA) to remove unbound radioactivity. Plates were dried, 50 µL Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 µM alprenolol. K$_i$ values for compounds were calculated from observed IC$_{50}$ values and the K$_d$ value of the radioligand using the Cheng-Prusoff equation (Cheng Y, and Prusoff W H., *Biochemical Pharmacology*, 1973, 22, 23, 3099-108). The receptor subtype selectivity was calculated as the ratio of K$_i$($\beta_1$)/K$_i$($\beta_2$). All of the compounds tested demonstrated greater binding at the $\beta_2$ adrenergic receptor than at the PI adrenergic receptor, i.e. K$_i$($\beta_1$)>K$_i$($\beta_2$). Most preferred compounds of the invention demonstrated a selectivity greater than about 20.

Test B

Whole-Cell cAMP Flashplate Assay with a Cell Line Heterologously Expressing Human $\beta_2$ Adrenergic Receptor For the determination of agonist potencies, a HEK-293 cell line stably expressing cloned human $\beta_2$ adrenergic receptor (clone H24.14) was grown to confluency in medium consisting of DMEM supplemented with 10% FBS and 500 µg/mL Geneticin. The day before the assay, antibiotics were removed from the growth-medium.

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed once with PBS, lifted with Versene 1:5,000 (0.2 g/L EDTA in PBS) and counted. Cells were pelleted by centrifugation at 1,000 rpm and resuspended in stimulation buffer prewarmed to 37° C. at a final concentration of 800,000 cells/mL. Cells were used at a final concentration of 40,000 cells/well in the assay. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer (75 mM Tris/HCl pH 7.4 @ 25° C., 12.5 mM MgCl$_2$, 1 mM EDTA, 0.2% BSA). Compounds were tested in the assay at 10 different concentrations, ranging from 2.5 µM to 9.5 pM. Reactions were incubated for 10 min at 37° C. and stopped by addition of 100 µl ice-cold detection buffer. Plates were sealed, incubated over night at 4° C. and counted the next morning in a topcount scintillation counter (Packard BioScience Co., Meriden, Conn.). The amount of cAMP produced per mL of reaction was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the 4-parameter model for sigmoidal dose-response with variable slope. Agonist potencies were expressed as $pEC_{50}$ values. All of the compounds tested demonstrated activity at the $\beta_2$ adrenergic receptor in this assay, as evidenced by $pEC_{50}$ values greater than about 5. Most preferred compounds of the invention demonstrated $pEC_{50}$ values greater than about 7.

Test C

Whole-Cell cAMP Flashplate Assay with a Lung Epithelial Cell Line Endogenously Expressing Human $\beta_2$ Adrenergic Receptor For the determination of agonist potencies and efficacies (intrinsic activities) in a cell line expressing endogenous levels of $\beta_2$ adrenergic receptor, a human lung epithelial cell line (BEAS-2B) was used (ATCC CRL-9609, American Type Culture Collection, Manassas, Va.) (January B, et al., *British Journal of Pharmacology*, 1998, 123, 4, 701-11). Cells were grown to 75-90% confluency in complete, serum-free medium (LHC-9 MEDIUM containing Epinephrine and Retinoic Acid, cat #181-500, Biosource International, Camarillo, Calif.). The day before the assay, medium was switched to LHC-8 (No epinephrine or retinoic acid, cat #141-500, Biosource International, Camarillo, Calif.).

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed with PBS, lifted by scraping with 5 mM EDTA in PBS, and counted. Cells were pelleted by centrifugation at 1,000 rpm and resuspended in stimulation buffer prewarmed to 37° C. at a final concentration of 600,000 cells/mL. Cells were used at a final concentration of 30,000 cells/well in the assay. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer (75 mM Tris/HCl pH 7.4 @ 25° C., 12.5 mM $MgCl_2$, 1 mM EDTA, 0.2% BSA).

Compounds were tested in the assay at 10 different concentrations, ranging from 10 μM to 40 pM. Maximal response was determined in the presence of 10 μM Isoproterenol. Reactions were incubated for 10 min at 37° C. and stopped by addition of 100 μl ice-cold detection buffer. Plates were sealed, incubated over night at 4° C. and counted the next morning in a topcount scintillation counter (Packard Bio-Science Co., Meriden, Conn.). The amount of cAMP produced per mL of reaction was calculated based on the counts observed for samples and cAMP standards, as described in the manufacturer's user manual. Data were analyzed by non-linear regression analysis with the GraphPad Prism Software package (GraphPad Software, Inc., San Diego, Calif.) using the 4-parameter model for sigmoidal dose-response with variable slope. Compounds of the invention tested in this assay demonstrated $pEC_{50}$ values greater than about 7.

Compound efficacy (% Eff) was calculated from the ratio of the observed Emax (TOP of the fitted curve) and the maximal response obtained for 10 μM isoproterenol and was expressed as % Eff relative to isoproterenol. The compounds tested demonstrated a % Eff greater than about 20.

Test D

Assay of Bronchoprotection Against Acetylcholine-Induced Bronchospasm in a Guinea Pig Model Groups of 6 male guinea pigs (Duncan-Hartley (HsdPoc: DH) Harlan, Madison, Wis.) weighing between 250 and 350 g were individually identified by cage cards. Throughout the study animals were allowed access to food and water ad libitum.

Test compounds were administered via inhalation over 10 minutes in a whole-body exposure dosing chamber (R&S Molds, San Carlos, Calif.). The dosing chambers were arranged so that an aerosol was simultaneously delivered to 6 individual chambers from a central manifold. Following a 60 minute acclimation period and a 10 minute exposure to nebulized water for injection (WFI), guinea pigs were exposed to an aerosol of test compound or vehicle (WFI). These aerosols were generated from aqueous solutions using an LC Star Nebulizer Set (Model 22F51, PARI Respiratory Equipment, Inc. Midlothian, Va.) driven by a mixture of gases ($CO_2$=5%, $O_2$=21% and $N_2$=74%) at a pressure of 22 psi. The gas flow through the nebulizer at this operating pressure was approximately 3 L/minute. The generated aerosols were driven into the chambers by positive pressure. No dilution air was used during the delivery of aerosolized solutions. During the 10 minute nebulization, approximately 1.8 mL of solution was nebulized. This was measured gravimetrically by comparing pre- and post-nebulization weights of the filled nebulizer.

The bronchoprotective effects of compounds administered via inhalation were evaluated using whole body plethysmography at 1.5, 24, 48 and 72 hours post-dose. Forty-five minutes prior to the start of the pulmonary evaluation, each guinea pig was anesthetized with an intramuscular injection of ketamine (43.75 mg/kg), xylazine (3.50 mg/kg) and acepromazine (1.05 mg/kg). After the surgical site was shaved and cleaned with 70% alcohol, a 2-5 cm midline incision of the ventral aspect of the neck was made. Then, the jugular vein was isolated and cannulated with a saline-filled polyethylene catheter (PE-50, Becton Dickinson, Sparks, Md.) to allow for intravenous infusions of a 0.1 mg/mL solution of acetylcholine (Ach), (Sigma-Aldrich, St. Louis, Mo.) in saline. The trachea was then dissected free and cannulated with a 14 G teflon tube (#NE-014, Small Parts, Miami Lakes, Fla.). If required, anesthesia was maintained by additional intramuscular injections of the aforementioned anesthetic cocktail. The depth of anesthesia was monitored and adjusted if the animal responded to pinching of its paw or if the respiration rate was greater than 100 breaths/minute.

Once the cannulations were complete, the animal was placed into a plethysmograph (#PLY3114, Buxco Electronics, Inc., Sharon, Conn.) and an esophageal pressure cannula was inserted to measure pulmonary driving pressure (pressure). The teflon tracheal tube was attached to the opening of the plethysmograph to allow the guinea pig to breathe room air from outside the chamber. The chamber was then sealed. A heating lamp was used to maintain body temperature and the guinea pig's lungs were inflated 3 times with 4 mL of air using a 10 mL calibration syringe (#5520 Series, Hans Rudolph, Kansas City, Mo.) to ensure that the lower airways had not collapsed and that the animal did not suffer from hyperventilation.

Once it was determined that baseline values were within the range 0.3-0.9 mL/cm $H_2O$ for compliance and within the range 0.1-0.199 cm $H_2O$/mL per second for resistance, the pulmonary evaluation was initiated. A Buxco pulmonary measurement computer program enabled the collection and derivation of pulmonary values. Starting this program initiated the experimental protocol and data collection. The changes in volume over time that occurred within the plethysmograph with each breath were measured via a Buxco pressure transducer. By integrating this signal over time, a measurement of flow was calculated for each breath. This signal, together with the pulmonary driving pressure changes, which were collected using a Sensym pressure transducer (#TRD4100), was connected via a Buxco (MAX 2270) preamplifier to a data collection interface (#'s SFT3400 and SFT3813). All other pulmonary parameters were derived from these two inputs.

Baseline values were collected for 5 minutes, after which time the guinea pigs were challenged with Ach. Ach was infused intravenously for 1 minute from a syringe pump (sp210iw, World Precision Instruments, Inc., Sarasota, Fla.) at the following doses and prescribed times from the start of the experiment: 1.9 μg/minute at 5 minutes, 3.8 μg/minute at 10 minutes, 7.5 μg/minute at 15 minutes, 15.0 μg/minute at 20 minutes, 30 μg/minute at 25 minutes and 60 μg/minute at 30 minutes. If resistance or compliance had not returned to baseline values at 3 minutes following each Ach dose, the guinea pig's lungs were inflated 3 times with 4 mL of air from a 10 mL calibration syringe. Recorded pulmonary parameters included respiration frequency (breaths/minute), compliance (mL/cm $H_2O$) and pulmonary resistance (cm $H_2O$/mL per second) (Giles et al., 1971). Once the pulmonary function measurements were completed at minute 35 of this protocol, the guinea pig was removed from the plethysmograph and euthanized by $CO_2$ asphyxiation.

The quantity $PD_2$, which is defined as the amount of Ach needed to cause a doubling of the baseline pulmonary resistance, was calculated using the pulmonary resistance values derived from the flow and the pressure over a range of Ach challenges using the following equation. This was derived from the equation used to calculate $PC_{20}$ values in the clinic (Am. Thoracic Soc, 2000).

$$PD_2 = \text{antilog}\left[\log C_1 + \frac{(\log C_2 - \log C_1)(2R_0 - R_1)}{R_2 - R_1}\right]$$

where:

$C_1$=Second to last Ach concentration (concentration preceding $C_2$)

$C_2$=Final concentration of Ach (concentration resulting in a 2-fold increase in pulmonary resistance ($R_L$))

$R_0$=Baseline $R_L$ value $R_1$=$R_L$ value after $C_1$ $R_2$=$R_L$ value after $C_2$ Statistical analysis of the data was performed using a One-Way Analysis of Variance followed by post-hoc analysis using a Bonferroni/Dunn test. A P-value<0.05 was considered significant.

Dose-response curves were fitted with a four parameter logistic equation using GraphPad Prism, version 3.00 for Windows (GraphPad Software, San Diego, Calif.)

$$Y = \text{Min} + (\text{Max} - \text{Min})/(1 + 10^{\wedge}((\log ED_{50} - X) * \text{Hillslope})),$$

where X is the logarithm of dose, Y is the response ($PD_2$), and Y starts at Min and approaches asymptotically to Max with a sigmoidal shape.

Representative compounds of the invention were found to have significant bronchoprotective activity at time points beyond 24 hours post-dose.

The following synthetic examples are offered to illustrate the invention, and are not to be construed in any way as limiting the scope of the invention.

EXAMPLES

In the examples below, the following abbreviations have the following meanings. Any abbreviations not defined have their generally accepted meaning. Unless otherwise stated, all temperatures are in degrees Celsius.

| | |
|---|---|
| Bn = | benzyl |
| Boc = | tert-butoxycarbonyl |
| DMSO = | dimethyl sulfoxide |
| EtOAc = | ethyl acetate |
| TFA = | trifluoroacetic acid |
| THF = | tetrahydrofuran |
| $MgSO_4$ = | anhydrous magnesium sulfate |
| NaHMDS = | sodium hexamethyldisilazane |
| TMSCl = | trimethylsilyl chloride |
| DMF = | dimethyl formamide |
| Boc = | tert-butoxycarbonyl |
| TBS = | tert-butyldimethylsilyl |

General: Unless noted otherwise, reagents, starting material and solvents were purchased from commercial suppliers, for example Sigma-Aldrich (St. Louis, Mo.), J. T. Baker (Phillipsburg, N.J.), Honeywell Burdick and Jackson (Muskegon, Mich.), Trans World Chemicals, Inc. (TCI) (Rockville, Md.), Mabybridge plc (Cornwall, UK), Peakdale Molecular Limited (High Peak, UK), Avocado Research Chemicals Limited (Lancashire, UK), and Bionet Research (Cornwall, UK) and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by preparative HPLC as described below; NMR samples were dissolved in deuterated solvent ($CD_3OD$, $CDCl_3$, or DMSO-d6), and spectra were acquired with a Varian Gemini 2000 instrument (300 MHz) using the residual protons of the listed solvent as the internal standard unless otherwise indicated; and mass spectrometric identification was performed by an electrospray ionization method (ESMS) with a Perkin Elmer instrument (PE SCIEX API 150 EX).

Example 1

Synthesis of Compound 1

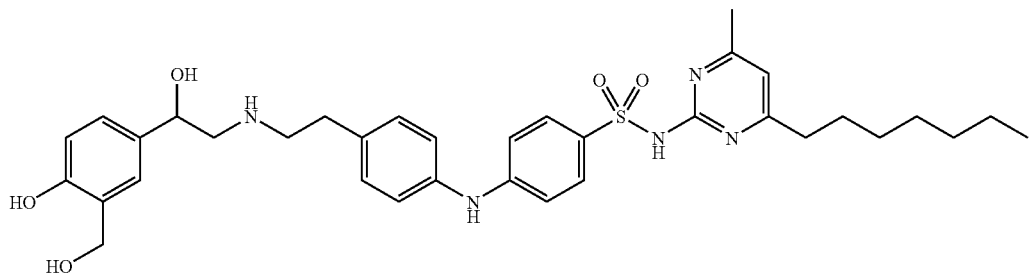

To 62 mg (0.1 mmol) of compound bb and 0.1 mmol of N$^1$-(4-heptyl-6-methyl-2-pyrimidinyl)sulfanilamide (available from Sigma-Aldrich Library of Rare Chemicals) 0.15 mL of toluene were added 9.3 mg (0.015 mmol) of racemic-2,2'-bis(diphenylphosphino)-1,1'-binaphthyl (Aldrich) in 0.15 mL toluene, 4.6 mg (0.05 mmol) of tris(dibenzylidineacetone)dipalladium(0) (Aldrich) in 0.1 mL toluene, and 29 mg (0.3 mmol) of sodium tert-butoxide slurried in 0.4 mL toluene. The mixture was shaken and heated at 80° C. for 5 hours. Acetic acid (80% aq., 0.6 mL) was added and the mixture was shaken and heated at 80° C. for 5 hours. The crude reaction was diluted to a total volume of 2 mL with DMF, filtered, and purified by reversed phase HPLC, using a mass-triggered, automated collection device. The product containing fractions were analyzed by analytical LC-MS, and freeze-dried to give a TFA salt of compound 1 as a powder.

The intermediate compound bb was prepared as follows.

a. Synthesis of Compound xx.

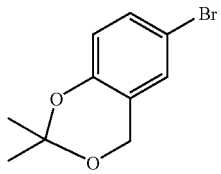

To 5-bromo-2-hydroxybenzyl alcohol (93 g, 0.46 mol, available from Aldrich) in 2.0 L of 2,2-dimethoxypropane was added 700 mL of acetone, followed by 170 g of ZnCl$_2$. After stirring for 18 hours, 1.0 M aqueous NaOH was added until the aqueous phase was basic. 1.5 L of diethyl ether was added to the slurry, and the organic phase was decanted into a seporatory funnel. The organic phase washed with brine, dried over Na$_2$SO$_4$, filtered, and concentrated under reduced pressure to give compound xx as a light orange oil. $^1$H NMR (300 MHz, DMSO-d6) δ 7.28 (m, 2H), 6.75 (d, 1H), 4.79 (s, 2H), 1.44 (s, 6H).

b. Synthesis of Compound yy

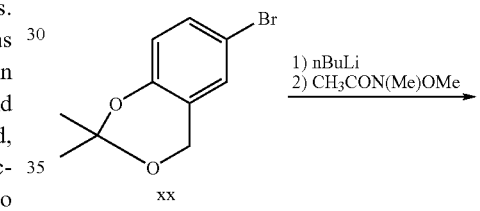

To 110 g (0.46 mol) of compound xx in 1.0 L of THF at −78° C. was added 236 mL (0.51 mol) of 2.14 M n-BuLi in hexanes via a dropping funnel. After 30 minutes, 71 g (0.69 mol) of N-Methyl-N-methoxyacetamide (available from TCI) was added. After 2 hours, the reaction was quenched with water, diluted with 2.0 L of 1.0 M aqueous phosphate buffer (pH=7.0), and extracted once with diethyl ether. The diethyl ether phase washed once with brine, dried over Na$_2$SO$_4$, filtered, and concentrated under reduced pressure to give a light orange oil. The oil was dissolved in a minimum volume of ethyl acetate, diluted with hexanes, and the product crystallized to give compound yy as a white solid. $^1$H NMR (300 MHz, CDCl$_3$) δ 7.79 (m, 1H), 7.65 (m, 1H), 6.85 (d, 1H), 4.88 (s, 2H), 2.54 (s, 3H), 1.56 (s, 6H).

c. Synthesis of Compound zz.

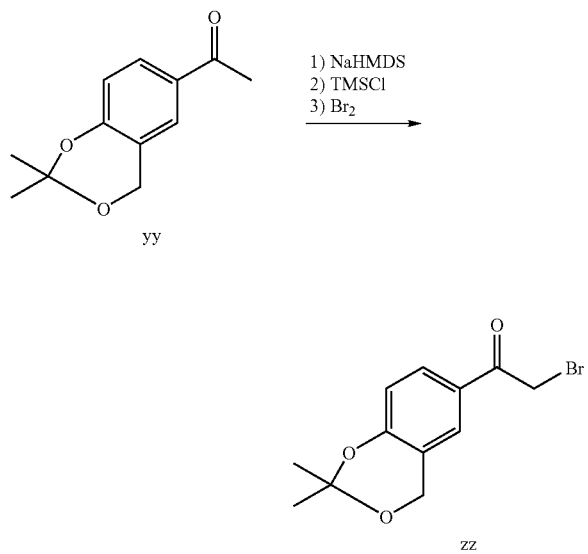

To 23.4 g (0.113 mol) of compound yy in 600 mL of THF at −78° C. was added 135 mL of 1.0 M NaHMDS in THF (Aldrich). After 1 hour, 15.8 mL (0.124 mol) of TMSCl was added. After another 30 minutes, 5.82 mL (0.113 mol) of bromine was added. After a final 10 minutes, the reaction was quenched by diluting with diethyl ether and pouring onto 500 mL of 5% aqueous $Na_2SO_3$ premixed with 500 mL of 5% aqueous $NaHCO_3$. The phases were separated, and the organic phase washed with brine, dried over $Na_2SO_4$, filtered, and concentrated under reduced pressure to give compound zz as a light orange oil that solidified in the freezer. $^1$H NMR (300 MHz, $CDCl_3$) δ 7.81 (m, 1H), 7.69 (m, 1H), 6.88 (d, 1H), 4.89 (s, 2H), 4.37 (s, 2H), 1.56 (s, 6H).

d. Synthesis of Compound aa.

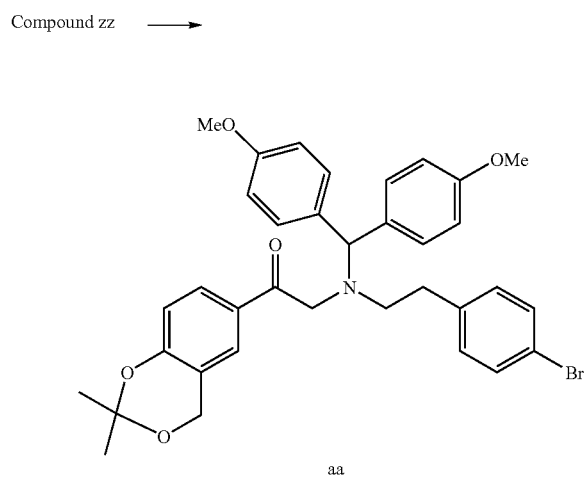

To 32 g (0.113 mol) of compound zz in 300 mL methylene chloride at 0° C. was added 31.6 mL (0.23 mol) of triethylamine, followed by 16.0 mL (0.10 mol) of 4-bromophenethylamine (Aldrich). After 2 hours, 27 g (0.10 mol) of the 4,4'-dimethoxychlorodiphenylmethane was added. After 30 minutes, the slurry was partitioned between 50% saturated aqueous $NaHCO_3$ and diethyl ether, and the phases were separated. The organic phase washed once each with water and brine, dried over $K_2CO_3$, filtered, and concentrated to an orange oil. The oil was purified by silica gel chromatography (1400 mL silica gel, eluted with 3 acetonitrile/0.5 triethylamine/96.5 methylene chloride) to give compound aa as a light orange foam. $^1$H NMR (300 MHz, DMSO-d6) δ 7.65 (m, 1H), 7.57 (m, 1H), 7.38 (d, 2H), 7.19 (d, 4H), 6.95 (d, 2H), 6.78 (m, 5H), 5.09 (s, 1H), 4.82 (s, 2H), 3.98 (s, 2H), 3.73 (m, 1H), 3.66 (s, 6H), 2.71 (m, 4H), 1.45 (s, 6H).

e. Synthesis of Compound bb.

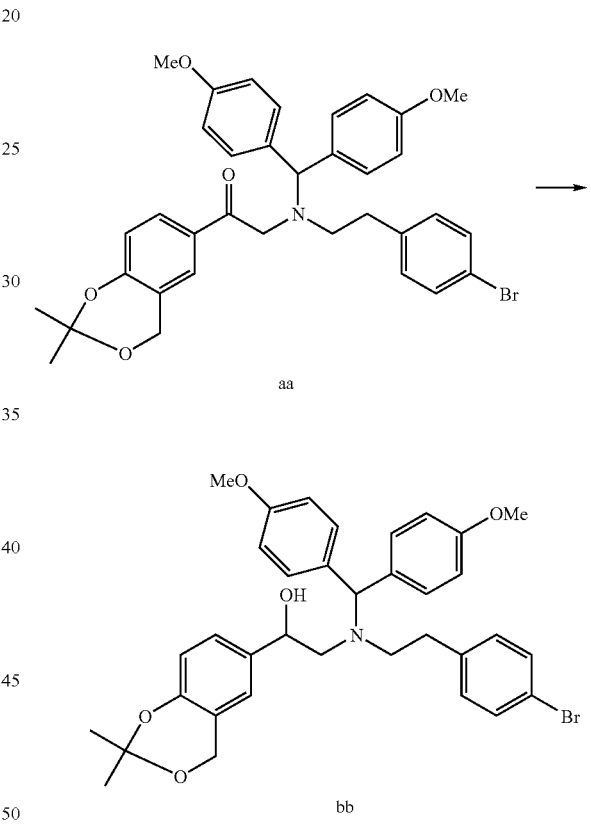

To 41 g (65 mmol) of compound aa in 120 mL of THF was added 200 mL of methanol, followed by 2.46 g (65 mmol) of sodium borohydride. After 1 hour, the solution was partitioned between 1.0 M aqueous phosphate buffer (pH=7.0) and diethyl ether, and the phases were separated. The diethyl ether phase washed with brine, dried over $K_2CO_3$, filtered, and concentrated to an oil. The oil was purified by silica gel chromatography (1200 mL silica gel, eluted with 18 acetone/ 0.5 triethylamine/81.5 hexanes) to give compound bb as a white foam. $^1$H NMR (300 MHz, DMSO-d6) δ 7.37 (d, 2H), 7.13 (m, 4H), 6.95-6.75 (m, 8H), 6.68 (d, 1H), 4.95 (d, 1H), 4.83 (s, 1H), 4.74 (s, 2H), 4.56 (m, 1H), 3.67 (2, 6H), 2.55 (m, 4H), 1.42 (s, 6H).

Example 2

Synthesis of Compound 2

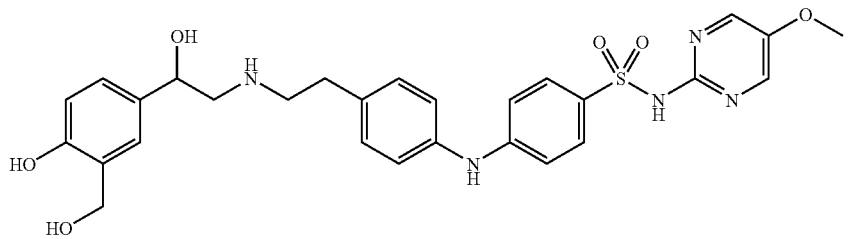

Using a coupling procedure similar to that described in Example 1, except replacing the N[1]-(4-heptyl-6-methyl-2-pyrimidinyl)sulfanilamide with N[1]-(5-methoxy-2-pyrimidinyl)sulfanilamide (sulfameter, available from Aldrich), a TFA salt of compound 2 was prepared. m/z: [M+H$^+$] calcd for $C_{28}H_{31}N_5O_6S$ 566.2. found 566.2.

Example 3

Synthesis of Compound 3

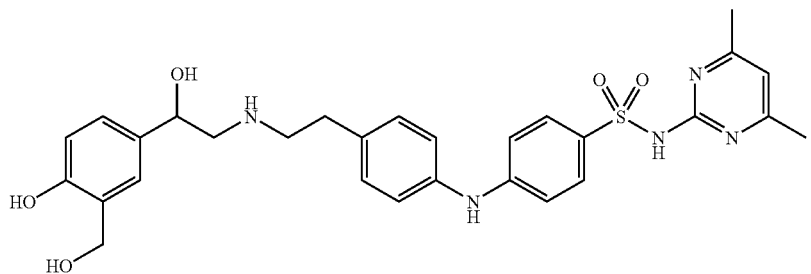

Using a coupling procedure similar to that described in Example 1, except replacing the N[1]-(4-heptyl-6-methyl-2-pyrimidinyl)sulfanilamide with N[1]-(4,6-dimethyl-2-pyrimidinyl)sulfanylamide (sulfamethazine, available from Aldrich), a TFA salt of compound 3 was prepared. m/z: [M+H$^+$] calcd for $C_{29}H_{33}N_5O_5S$ 564.2. found 564.2.

Example 4

Synthesis of Compound 4

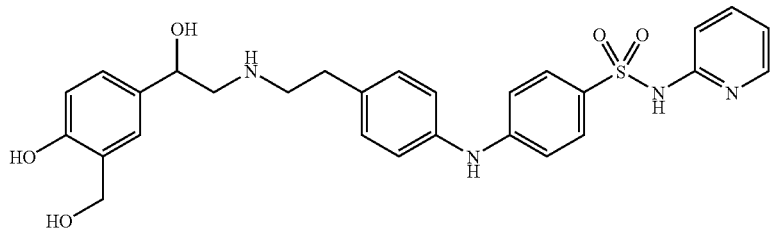

Using a coupling procedure similar to that described in Example 1, except replacing the N$^1$-(4-heptyl-6-methyl-2-pyrimidinyl)sulfanilamide with 2-sulfanilamidopyrimidine (sulfapyridine, available from Aldrich), a TFA salt of compound 4 was prepared. m/z: [M+H$^+$] calcd for $C_{28}H_{30}N_4O_5S$ 535.2. found 535.2.

Example 5

Synthesis of Compound 5

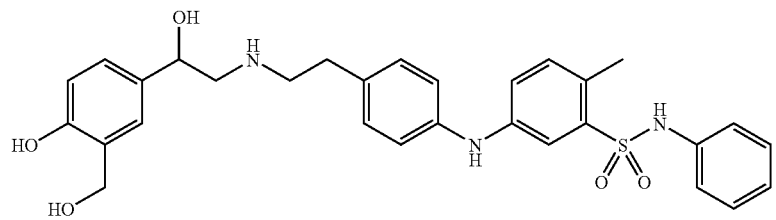

Using a coupling procedure similar to that described in Example 1, except replacing the N$^1$-(4-heptyl-6-methyl-2-pyrimidinyl)sulfanilamide with 5-amino-ortho-toluenesulfonanilide (p-toluidine-o-sulfanilide, available from Sigma-Aldrich Library of Rare Chemicals), a TFA salt of compound 5 was prepared. m/z: [M+H$^+$] calcd for $C_{30}H_{33}N_3O_5S$ 548.2. found 548.2.

Example 6

Synthesis of Compound 6

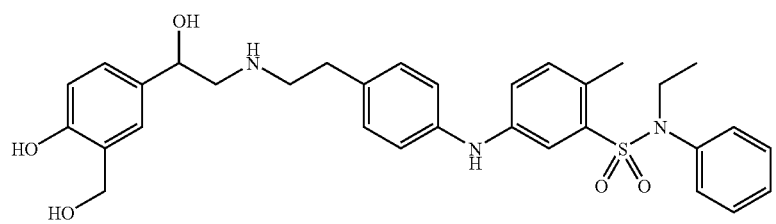

Using a coupling procedure similar to that described in Example 1, except replacing the N$^1$-(4-heptyl-6-methyl-2-pyrimidinyl)sulfanilamide with 4-aminotoluene-2-sulfethylanilide (available from Sigma-Aldrich Library of Rare Chemicals), a TFA salt of compound 6 was prepared. m/z: [M+H$^+$] calcd for $C_{32}H_{37}N_3O_5S$ 576.3. found 576.2.

Example 7

Synthesis of Compound 7

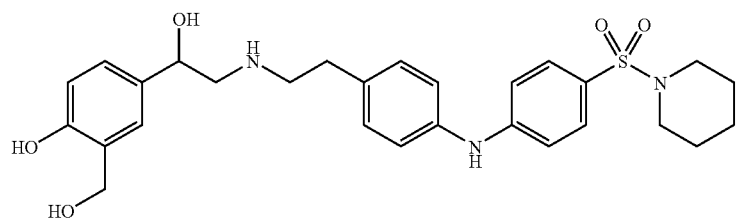

Using a coupling procedure similar to that described in Example 1, except replacing the $N^1$-(4-heptyl-6-methyl-2-pyrimidinyl)sulfanilamide with 4-(piperidinosulfonyl)aniline (available from Maybridge), a TFA salt of compound 7 was prepared. m/z: [M+H$^+$] calcd for $C_{28}H_{35}N_3O_5S$ 526.2. found 526.2.

Example 8

Synthesis of Compound 8

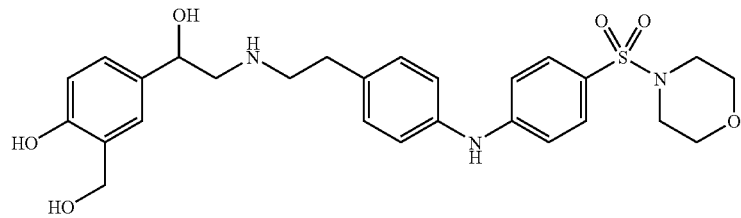

Using a coupling procedure similar to that described in Example 1, except replacing the $N^1$-(4-heptyl-6-methyl-2-pyrimidinyl)sulfanilamide with 4-(morpholinosulfonyl)aniline (available from Maybridge), a TFA salt of compound 8 was prepared. m/z: [M+H$^+$] calcd for $C_{27}H_{33}N_3O_6S$ 528.2. found 528.2.

Example 9

Synthesis of Compound 9

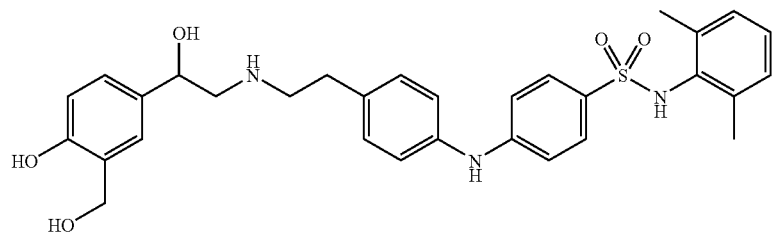

Using a coupling procedure similar to that described in Example 1, except replacing the $N^1$-(4-heptyl-6-methyl-2-pyrimidinyl)sulfanilamide with $N^1$-(2,6-dimethylphenyl)-4-aminobenzene-1-sulfonamide (available from Maybridge), a TFA salt of compound 9 was prepared. m/z: [M+H$^+$] calcd for $C_{31}H_{35}N_3O_5S$ 562.2. found 562.2.

Example 10

Synthesis of Compound 10

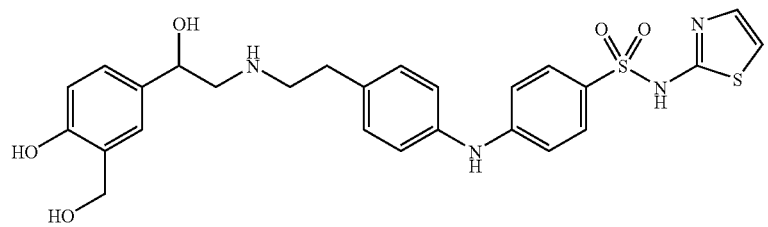

Using a coupling procedure similar to that described in Example 1, except replacing the $N^1$-(4-heptyl-6-methyl-2-pyrimidinyl)sulfanilamide with $N^1$-(2-thiazolyl)sulfanilamide (sulfathiazole, available from Aldrich), a TFA salt of compound 10 was prepared.

Example 11

Synthesis of Compound 11

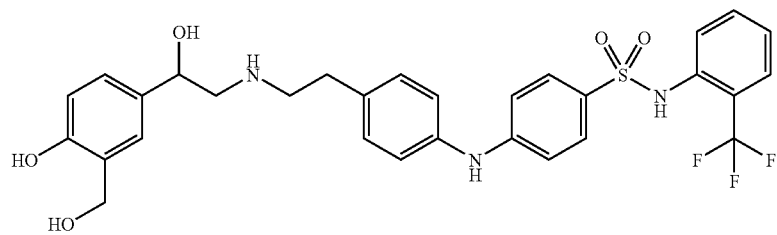

Using a coupling procedure similar to that described in Example 1, except replacing the $N^1$-(4-heptyl-6-methyl-2-pyrimidinyl)sulfanilamide with $N^1$-[2-(trifluoromethyl)phenyl]-4-aminobenzene-1-sulfonamide (available from Maybridge), a TFA salt of compound 11 was prepared.

Example 12

Synthesis of Compound 12

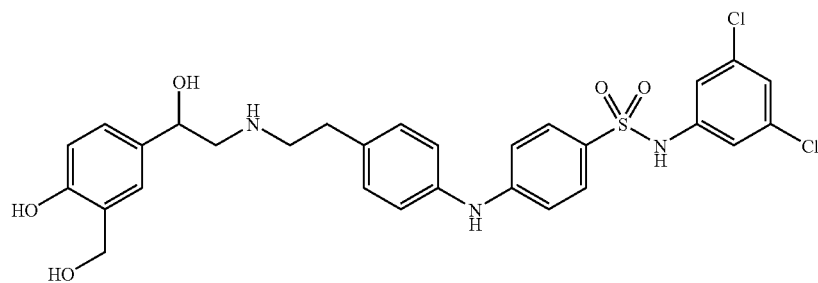

Using a coupling procedure similar to that described in Example 1, except replacing the $N^1$-(4-heptyl-6-methyl-2-pyrimidinyl)sulfanilamide with $N^1$-(3,5-dichlorophenyl)-4-aminobenzene-1-sulfonamide (available from Maybridge), a TFA salt of compound 12 was prepared.

Example 13

Synthesis of Compound 13

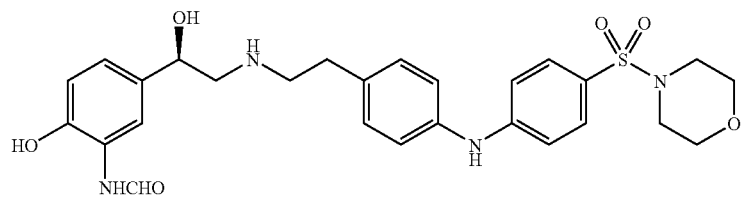

To a mixture of 0.69 g (1.83 mmol) of crude compound ee in 4 mL of methanol was added 70 mg of 10% palladium on carbon under a stream of nitrogen and the reaction was shaken under 50 psi $H_2$ for 2 days. The reaction was filtered and the residue was purified by reversed phase HPLC (gradient of 10 to 50% acetonitrile in 0.1% aqueous TFA). Fractions containing pure product were combined and lyophilized to afford a TFA salt of compound 13 as a powder. m/z: [M+H$^+$] calcd for $C_{27}H_{32}N_4O_6S$ 541.2. found 541.5.

The intermediate compound ee was prepared as follows.

a. Synthesis of Compound A.

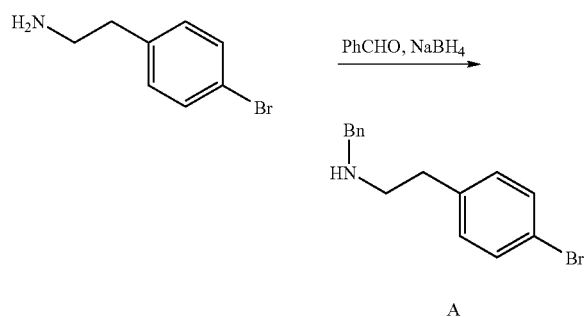

To 10.7 g (53.0 mmol) of 4-bromophenethylamine (available from Aldrich) in 100 mL of toluene was added 6.80 g (64 mmol) of benzaldehyde. After stirring for 10 minutes, the cloudy mixture was concentrated under reduced pressure. The residue was re-concentrated twice from toluene, and the clear oil was dissolved in 50 mL of tetrahydrofuran. 2.0 g (53 mmol) of sodium borohydride was added to the solution, followed by 20 mL of methanol, and the flask was stirred in a water bath at ambient temperature for one hour. 1.0 M aqueous HCl was added until the pH was below 1. The slurry was stirred in an ice bath for 30 minutes, and the solids were isolated by filtration, rinsed with cold water, and air dried to give the hydrochloride salt of compound A as a colorless solid. $^1$H NMR (300 MHz, DMSO-d6) δ 9.40 (s, 2H), 7.50-7.32 (m, 7H), 7.14 (d, 2H), 4.07 (s, 2H), 3.03 (m, 2H), 2.92 (m, 2H).

b. Synthesis of Compound B.

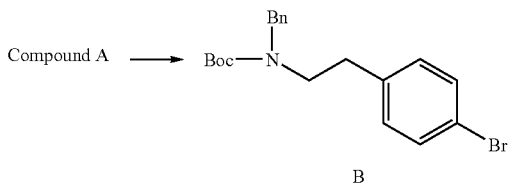

To 5.0 g (15 mmol) of compound A in 100 mL of methanol was added 1.70 g (16.5 mmol) of triethylamine. The solution was cooled in an ice/water bath, and 3.66 g (16.8 mmol) of di-tert-butyldicarbonate was added. After 3.5 hours, the solution was concentrated under reduced pressure, and the residue was partitioned between 1.0 M aqueous NaHSO$_4$ and diethyl ether, and the phases were separated. The diethyl ether phase washed with water followed by brine, dried over Na$_2$SO$_4$, filtered, and concentrated to give compound B (6.1 g, 93%) as a colorless oil. $^1$H NMR (300 MHz, DMSO-d6) δ 7.38 (d, 2H), 7.28-7.13 (m, 5H), 7.04 (m, 2H), 4.29 (br s, 2H), 3.20 (m, 2H), 2.62 (m, 2H), 1.25 (s, 9H).

c. Synthesis of Compound dd.

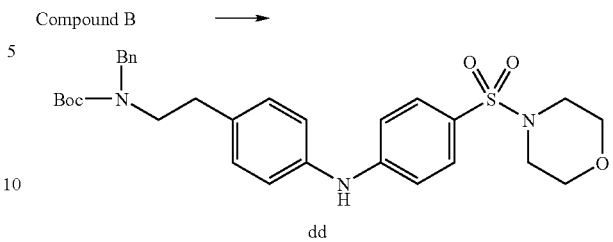

To a flask containing 3.4 g (8.8 mmol) of compound B, 2.8 g (11 mmol) of 4-morpholinosulfonyl)aniline (available from Maybridge), 0.41 g (0.45 mmol) of tris(dibenzylidineacetone)dipalladium(0), 0.83 g (1.3 mmol) of rac-2,2'-bis(diphenylphosphino)-1,1'-binaphthyl, and 1.1 g (11 mmol) of sodium tert-butoxide was added 40 mL of toluene, and the mixture was heated at 95° C. for 6 h under a nitrogen atmosphere. The mixture was diluted with 200 mL diethyl ether and washed twice with 100 mL portions of 1.0 M aqueous NaHSO$_4$, followed by 100 mL of saturated aqueous NaHCO$_3$. The diethyl ether phase was dried over MgSO$_4$, filtered, and concentrated to a dark oil. The oil was purified by silica gel chromatography (gradient of 30 to 40% ethyl acetate in hexanes) to afford compound dd as a yellow foam (2.5 g, 51%).

d. Synthesis of Compound ee.

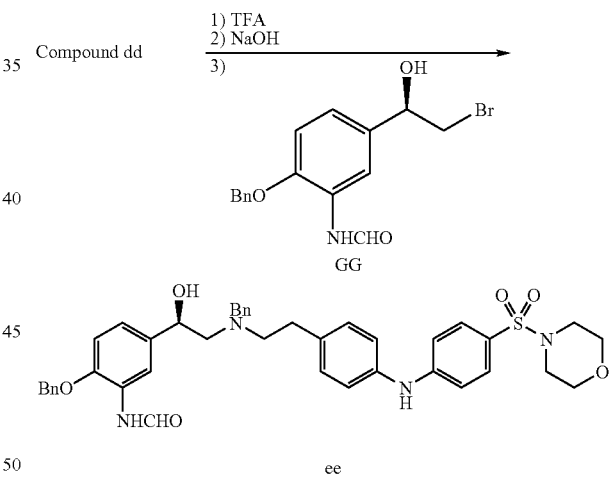

To 0.56 g of compound dd (0.6 mmol) in 6 mL CH$_2$Cl$_2$ was added 4 mL TFA. After 15 minutes, the solution was concentrated, diluted with 30 mL ethyl acetate and washed twice with 1.0 N aqueous sodium hydroxide. The ethyl acetate layer was dried over MgSO$_4$, filtered, and concentrated to an oil and dissolved in 8 mL of 1:1 methanol:THF. Bromohydrin GG (340 mg, 0.96 mmol) and K$_2$CO$_3$ (370 mg, 2.7 mmol) were added and the reaction was stirred at room temperature for 1.5 h. The reaction was concentrated and the residue was diluted with 30 mL water and extracted twice with 30 mL portions of toluene. The toluene extracts were combined, dried over Na$_2$SO$_4$, filtered, and concentrated. The residue was heated to 120° C. After 13 h, the reaction was cooled to room temperature and the crude compound dd was carried on to the next step without purification.

The intermediate bromohydrin GG can be prepared as described in U.S. Pat. No. 6,268,533 B1; and in R. Hett et al., *Organic Process Research and Development,* 1998, 2, 96-99. The intermediate bromohydrin GG can also be prepared using procedures similar to those described by Hong et al., *Tetrahedron Lett.,* 1994, 35, 6631; or similar to those described in U.S. Pat. No. 5,495,054.

Example 14

Synthesis of Compound 14

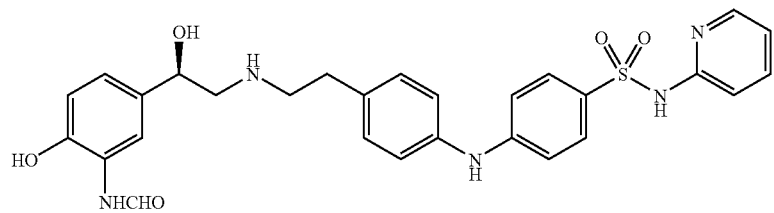

To a mixture of 0.6 g (0.83 mmol) of compound 11 in 25 mL of ethanol was added 200 mg of 10% palladium on carbon under a stream of nitrogen and the reaction was allowed to stir under H$_2$ at atmospheric pressure for 5 days. The reaction was filtered and the residue was purified by reversed phase HPLC (gradient of 10 to 50% acetonitrile in 0.1% aqueous TFA). Fractions containing pure product were combined and lyophilized to afford a TFA salt of compound 14 as a powder. m/z: [M+H$^+$] calcd for C$_{28}$H$_{29}$N$_5$O$_5$S 548.2. found 548.3.

The intermediate ii was prepared as follows.

a. Synthesis of Compound hh.

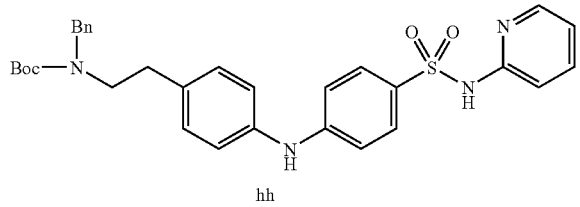

To a flask containing 3.4 g (8.8 mmol) of compound B (Example 13, part b), 2.0 g (8.0 mmol) of sulfapyridine (available from Aldrich), 0.37 g (0.40 mmol) of tris(dibenzylidineacetone)dipalladium(0), 0.75 g (1.2 mmol) of racemic-2,2'-bis(diphenylphosphino)-1,1'-binaphthyl, and 2.31 g (24.0 mmol) of sodium tert-butoxide was added 40 mL of toluene, and the mixture was heated at 90° C. for 18 h under a nitrogen atmosphere. The mixture was diluted with 200 mL methylene chloride and washed with 100 mL of saturated aqueous NaHCO$_3$, followed by 100 mL saturated aqueous NaCl. The organic phase was dried over MgSO$_4$, filtered, and concentrated. The oil was purified by silica gel chromatography (gradient of 0 to 5% methanol in methylene chloride) to afford compound hh as an orange solid.

b. Synthesis of Compound 11.

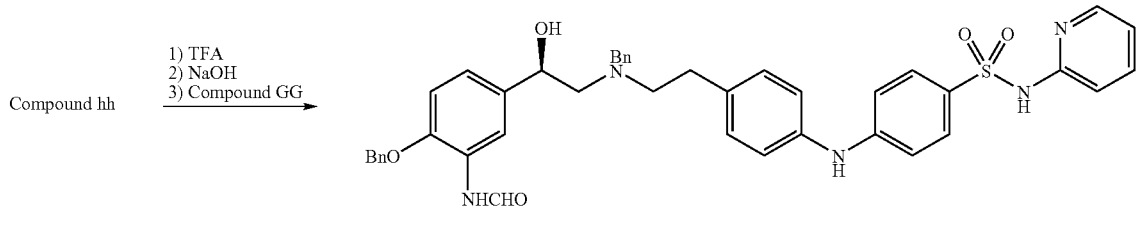

To 4.5 g of compound hh (8.1 mmol) in 20 mL CH$_2$Cl$_2$ was added 1.5 mL TFA. After 1 hour, the solution was concentrated, basified with 1.0 N aqueous sodium hydroxide and extracted twice with methylene chloride, followed by an extraction using ethyl acetate. The organic layers were combined, dried over MgSO$_4$, filtered, and concentrated to an oil. The oil was purified by silica gel chromatography (gradient of 2 to 10% methanol in methylene chloride). The purified product was dissolved in 10 mL of 1:1 methanol:THF. Bromohydrin GG (Example 13, part d) (364 mg, 1.04 mmol) and K$_2$CO$_3$ (378 mg, 2.73 mmol) were added and the reaction was stirred at room temperature for 1.5 h. The reaction was concentrated and the residue was diluted with 30 mL water and extracted twice with 30 mL portions of toluene. The toluene extracts were combined, dried over Na$_2$SO$_4$, filtered, and concentrated. The residue was heated to 120° C. After 2 h, the reaction was cooled to room temperature and the crude compound was purified by silica gel chromatography (gradient of 5 to 10% methanol in methylene chloride) to afford compound 11 as a tan solid.

Example 15

Synthesis of Compound 15

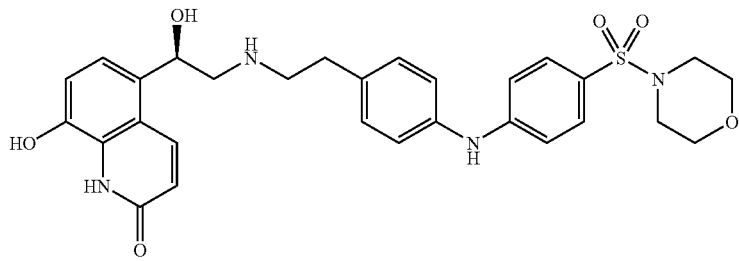

To 610 mg of compound ff (0.82 mmol) in 5.0 mL acetic acid was added 92 mg of 10% palladium on carbon. The reaction mixture was shaken under 40 psi $H_2$ for 20 h. The mixture was filtered and the filtrate was purified by reversed phase HPLC (gradient of 10 to 40% acetonitrile in 0.1% aqueous TFA). Fractions containing pure product were combined and lyophilized to afford a TFA salt of compound 15 as a powder.

m/z: [M+H$^+$] calcd for $C_{29}H_{32}N_4O_6S$ 565.2. found 565.3.

The intermediate compound ff was prepared as follows.

a. Synthesis of Compound ff.

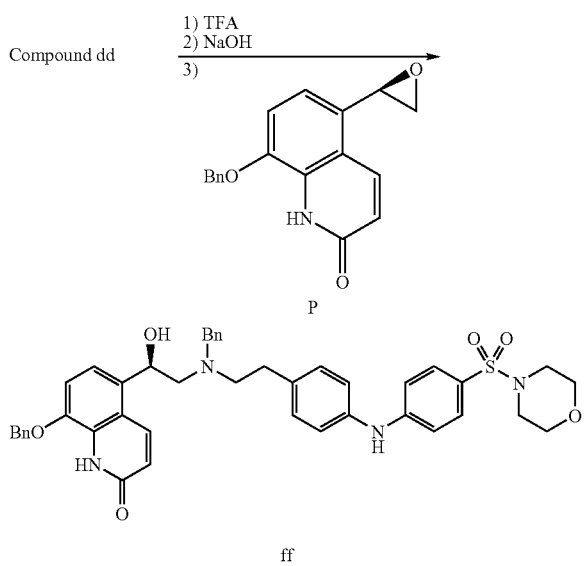

To 0.91 g of compound dd (1.6 mmol, Example 13, part c) in 8 mL $CH_2Cl_2$ was added 6 mL TFA. After 15 minutes, the solution was concentrated, diluted with 30 mL ethyl acetate and washed twice with 1.0 N aqueous sodium hydroxide. The ethyl acetate layer was dried over $MgSO_4$, filtered, and concentrated to a brown oil. The oil was dissolved in 6.0 mL of isopropanol and 375 mg (1.3 mmol) of epoxide P were added. The solution was heated to 70° C. After 24 h, the solution was concentrated and the product purified by silica gel chromatography (3% methanol in $CH_2Cl_2$). Pure fractions were combined and concentrated to afford compound ff as a yellow foam.

The intermediate epoxide P can be prepared as described in International Patent Application Publication Number WO 95/25104; and as described in EP 0 147 719 A2 and EP 0 147 791 B.

Example 16

Synthesis of Compound 16

Using a coupling procedure similar to that described in Example 1, except replacing the N$^1$-(4-heptyl-6-methyl-2-pyrimidinyl)sulfanilamide with 3-(methylthio)aniline (available from Aldrich), a TFA salt of compound 16 was prepared.

m/z: [M+H$^+$] calcd for $C_{24}H_{28}N_2O_3S$ 425.2. found 425.1.

Example 17

Synthesis of Compound 17

Using a coupling procedure similar to that described in Example 1, except replacing the N$^1$-(4-heptyl-6-methyl-2-pyrimidinyl)sulfanilamide with 4-(methylthio)aniline (available from Aldrich), a TFA salt of compound 17 was prepared. m/z: [M+H⁺] calcd for $C_{24}H_{28}N_2O_3S$ 425.2. found 425.1.

Example 18

Synthesis of Compound 18

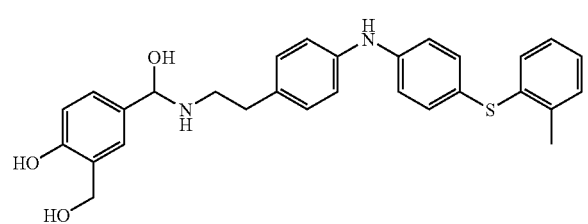

Using a coupling procedure similar to that described in Example 1, except replacing the $N^1$-(4-heptyl-6-methyl-2-pyrimidinyl)sulfanilamide 4-(m-tolylthio)aniline (available from Sigma-Aldrich Library of Rare Chemicals), a TFA salt of compound 18 was prepared. m/z: [M+H⁺] calcd for $C_{30}H_{32}N_2O_3S$ 501.2. found 501.2.

Example 19

Synthesis of Compound 19

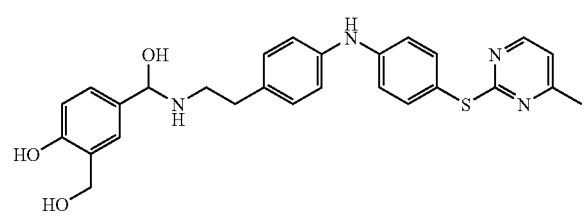

Using a coupling procedure similar to that described in Example 1, except replacing the $N^1$-(4-heptyl-6-methyl-2-pyrimidinyl)sulfanilamide with 4-[(4-methylpyrimidin-2-yl)thio]benzeneamine (available from Peakdale), a TFA salt of compound 19 was prepared. m/z: [M+H⁺] calcd for $C_{28}H_{30}N_4O_3S$ 503.2. found 503.1.

Example 20

Synthesis of Compound 20

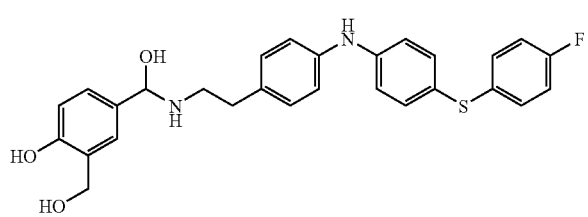

Using a coupling procedure similar to that described in Example 1, except replacing the $N^1$-(4-heptyl-6-methyl-2-pyrimidinyl)sulfanilamide with 4-[(4-fluorophenyl)sulfonyl]aniline (available from Bionet), a TFA salt of compound 20 was prepared.

Example 21

Synthesis of Compound 21

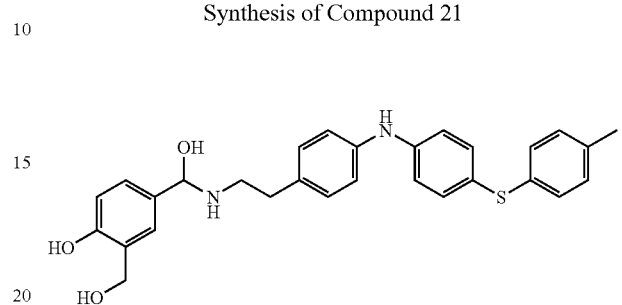

Using a coupling procedure similar to that described in Example 1, except replacing the $N^1$-(4-heptyl-6-methyl-2-pyrimidinyl)sulfanilamide with 4-[(4-methylphenyl)sulfonyl]aniline (available from Bionet), a TFA salt of compound 21 was prepared.

Example 22

Synthesis of Compound 22

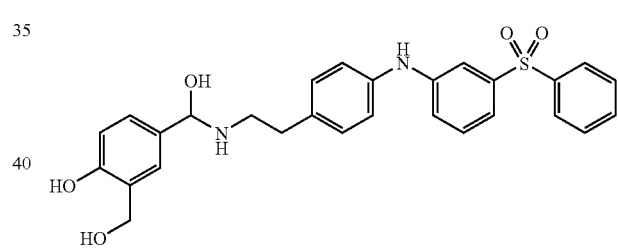

Using a coupling procedure similar to that described in Example 1, except replacing the $N^1$-(4-heptyl-6-methyl-2-pyrimidinyl)sulfanilamide with 3-aminodiphenyl sulfone (available from Sigma-Aldrich Library of Rare Chemicals), a TFA salt of compound 22 was prepared. m/z: [M+H⁺] calcd for $C_{29}H_{30}N_2O_5S$ 519.2. found 519.2.

Example 23

Synthesis of Compound 23

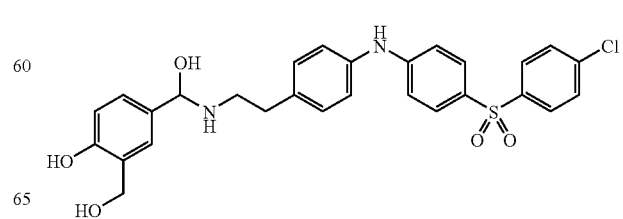

Using a coupling procedure similar to that described in Example 1, except replacing the $N^1$-(4-heptyl-6-methyl-2-pyrimidinyl)sulfanilamide with 4-(4-chloro-benzenesulfonyl)-phenylamine (available from Sigma-Aldrich Library of Rare Chemicals), a TFA salt of compound 23 was prepared. m/z: [M+H$^+$] calcd for $C_{29}H_{29}ClN_2O_5S$ 553.2. found 553.1.

Example 24

Synthesis of Compound 24

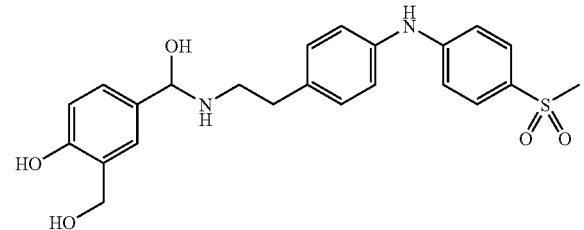

Using a coupling procedure similar to that described in Example 1, except replacing the $N^1$-(4-heptyl-6-methyl-2-pyrimidinyl)sulfanilamide with 4-(methylsulfonyl)aniline (available from Maybridge), a TFA salt of compound 24 was prepared. m/z: [M+H$^+$] calcd for $C_{24}H_{28}N_2O_5S$ 457.2. found 457.1.

Example 25

Synthesis of Compound 25

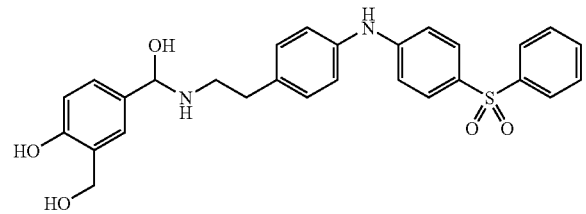

Using a coupling procedure similar to that described in Example 1, except replacing the $N^1$-(4-heptyl-6-methyl-2-pyrimidinyl)sulfanilamide with 4-(phenylsulfonyl)aniline (available from Maybridge), a TFA salt of compound 25 was prepared. m/z: [M+H$^+$] calcd for $C_{29}H_{30}N_2O_5S$ 519.2. found 519.2.

Example 26

Synthesis of Compound 26

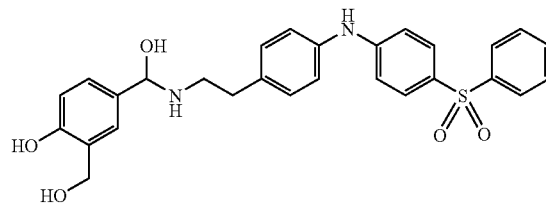

Using a coupling procedure similar to that described in Example 1, except replacing the $N^1$-(4-heptyl-6-methyl-2-pyrimidinyl)sulfanilamide with 4-[(4-fluorophenyl)sulfonyl] aniline (available from Maybridge), a TFA salt of compound 26 was prepared. m/z: [M+H$^+$] calcd for $C_{29}H_{29}FN_2O_5S$ 537.2. found 537.1.

Example 27

Synthesis of Compound 27

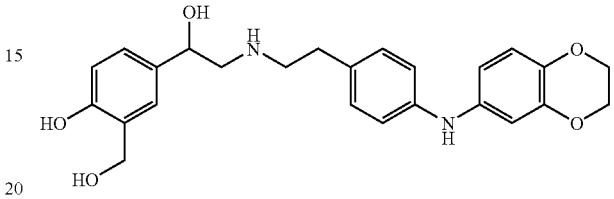

Using a coupling procedure similar to that described in Example 1, except replacing the $N^1$-(4-heptyl-6-methyl-2-pyrimidinyl)sulfanilamide with 3,4-ethylenedioxyaniline (available from Aldrich), a TFA salt of compound 27 was prepared.

Example 28

Synthesis of Compound 28

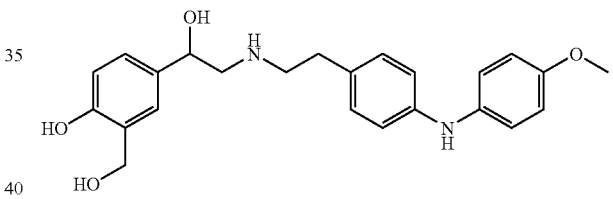

Using a coupling procedure similar to that described in Example 1, except replacing the $N^1$-(4-heptyl-6-methyl-2-pyrimidinyl)sulfanilamide with 4-methoxyaniline (p-anisidine, available from Aldrich), a TFA salt of compound 28 was prepared.

Example 29

Synthesis of Compound 29

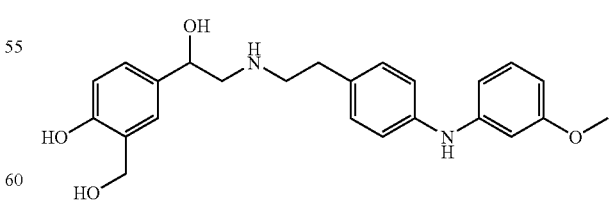

Using a coupling procedure similar to that described in Example 1, except replacing the $N^1$-(4-heptyl-6-methyl-2-pyrimidinyl)sulfanilamide with 3-ethoxyaniline (m-anisidine, available from Aldrich), a TFA salt of compound 29 was prepared.

Example 30

Synthesis of N-{2-[4-(4-ethoxyphenyl)aminophenyl]ethyl}-2-hydroxy-2-(3-hydroxymethyl-4-hydroxyphenyl)ethylamine (30)

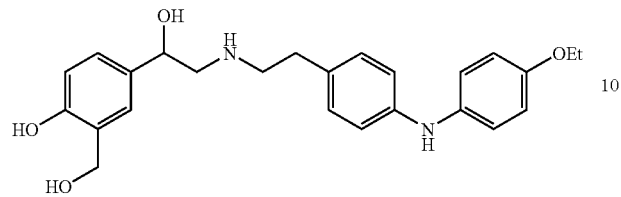

Using a coupling procedure similar to that described in Example 1, except replacing the $N^1$-(4-heptyl-6-methyl-2-pyrimidinyl)sulfanilamide with 1-amino-4-ethoxybenzene (p-phenetidine, available from Aldrich), a TFA salt of compound 30 was prepared.

Example 31

Synthesis of Compound 31

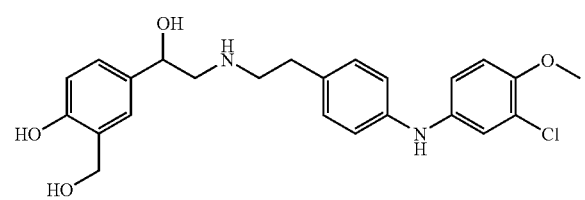

Using a coupling procedure similar to that described in Example 1, except replacing the $N^1$-(4-heptyl-6-methyl-2-pyrimidinyl)sulfanilamide with 3-chloro-4-methoxyaniline (available from Aldrich), a TFA salt of compound 31 was prepared.

Example 32

Synthesis of Compound 32

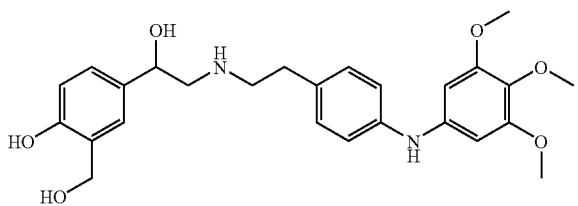

Using a coupling procedure similar to that described in Example 1, except replacing the $N^1$-(4-heptyl-6-methyl-2-pyrimidinyl)sulfanilamide with 3,4,5-trimethoxyaniline (available from Aldrich), a TFA salt of compound 32 was prepared. m/z: [M+H$^+$] calcd for $C_{26}H_{32}N_2O_6$ 469.2. found 469.2.

Example 33

Synthesis of Compound 33

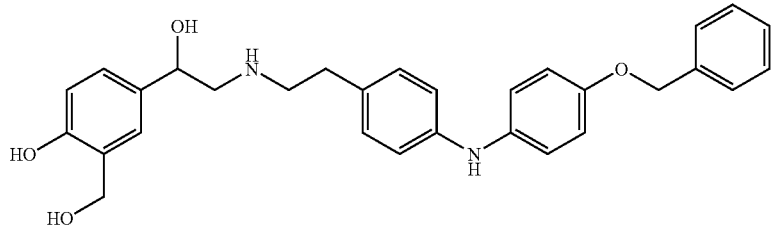

Using a coupling procedure similar to that described in Example 1, except replacing the $N^1$-(4-heptyl-6-methyl-2-pyrimidinyl)sulfanilamide with 4-benzyloxyaniline hydrochloride (available from Aldrich), a TFA salt of compound 33 was prepared. m/z: [M+H$^+$] calcd for $C_{30}H_{32}N_2O_4$ 485.2. found 485.2.

Example 34

Synthesis of Compound 34

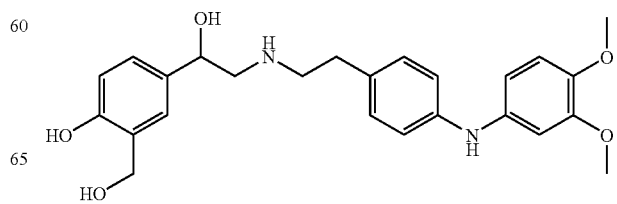

Using a coupling procedure similar to that described in Example 1, except replacing the N¹-(4-heptyl-6-methyl-2-pyrimidinyl)sulfanilamide with 3,4-dimethoxyaniline (available from Aldrich), a TFA salt of compound 34 was prepared. m/z: [M+H⁺] calcd for $C_{25}H_{30}N_2O_5$ 439.2. found 439.2.

Example 35

Synthesis of Compound 35

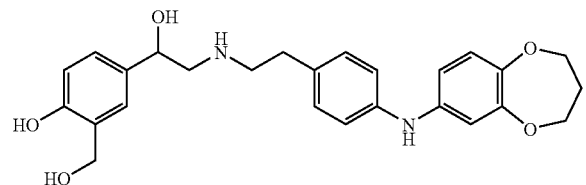

Using a coupling procedure similar to that described in Example 1, except replacing the N¹-(4-heptyl-6-methyl-2-pyrimidinyl)sulfanilamide with 3,4-(trimethylenedioxy)aniline (available from Maybridge), a TFA salt of compound 35 was prepared. m/z: [M+H⁺] calcd for $C_{26}H_{30}N_2O_5$ 451.2. found 451.2.

Example 36

Synthesis of Compound 36

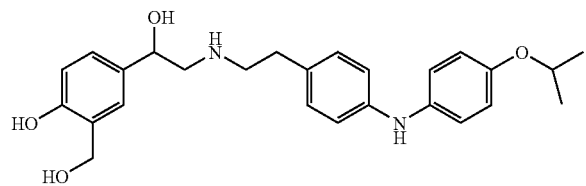

Using a coupling procedure similar to that described in Example 1, except replacing the N¹-(4-heptyl-6-methyl-2-pyrimidinyl)sulfanilamide with 4-isopropoxyaniline (available from TCI America), a TFA salt of compound 36 was prepared. m/z: [M+H⁺] calcd for $C_{26}H_{32}N_2O_4$ 437.2. found 437.2.

Example 37

Synthesis of N-{2-[4-(4-ethoxyphenyl)aminophenyl]ethyl}-(R)-2-hydroxy-2-(3-hydroxymethyl-4-hydroxyphenyl)ethylamine (37)

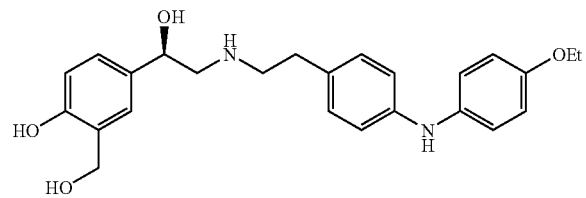

To a mixture of 3.0 g (4.98 mmol) of compound F, prepared in part c below, in 70 ml of ethanol was added 1.0 g of 10% Palladium on carbon under a stream of nitrogen. The flask was fitted with a balloon of hydrogen gas, and the reaction was vigorously stirred for 1.5 hours. The reaction was filtered through celite, using methanol to rinse, and the filtrate was concentrated under reduced pressure. The residue was dissolved in 40 ml of 1/1 isopropanol/methanol, 2.74 ml of 4M HCl in dioxane was added, and the product was precipitated as the di-HCl salt by adding the solution to a large volume of EtOAc. The solids were isolated by filtration to give the di-HCl salt of compound 37 as a white solid. ¹H NMR (300 MHz, DMSO-d6) δ 8.94 (br s, 1H), 8.63 (br s, 1H), 6.97-6.67 (m, 11H), 4.76 (m, 1H), 4.39 (s, 2H), 4.29 (br, 4H), 3.87 (dd, 2H), 3.02-2.76 (m, 6H), 1.22 (t, 3H). m/z: [M+H⁺] calcd for $C_{25}H_{30}N_2O_4$ 423.2. found 423.2.

The intermediate compound F was prepared as follows.

a. Synthesis of Compound C.

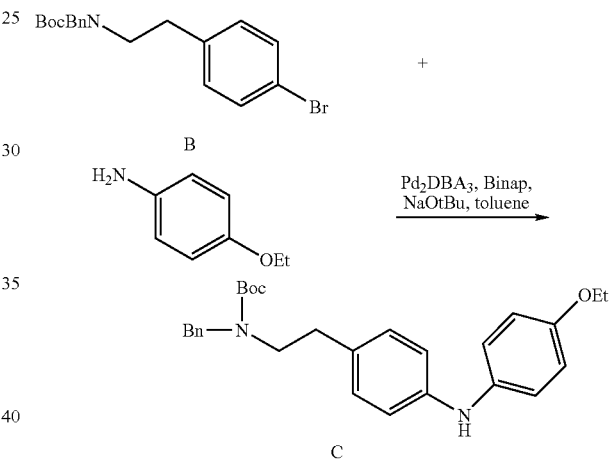

To a flask containing 3.0 g (7.7 mmol) of compound B, 1.26 g (9.1 mmol, Example 13, part b) of para-phenetidine (4-ethoxyaniline, available from Aldrich), 0.32 g (0.35 mmol) of tris(dibenzylidineacetone)dipalladium(0), 0.65 g (1.05 mmol) of racemic-2,2'-bis(diphenylphosphino)-1,1'-binaphthyl, and 0.88 g (9.1 mmol) of sodium tert-butoxide was added 35 ml of toluene, and the mixture was heated at 95° C. for 5.5 hours under a nitrogen atmosphere. The mixture was partitioned between 1.0 M aqueous NaHSO₄ and diethyl ether, and the phases were separated. The diethyl ether phase was diluted with one volume of hexanes, and washed once each with 1.0 M aqueous NaHSO₄ and brine, dried over Na₂SO₄, filtered, and concentrated to a dark oil. The oil was purified by chromatography, using 15% EtOAc/85% hexanes as eluent, to give 2.52 g (73%) of compound C as a dark orange oil. ¹H NMR (300 MHz, DMSO-d6) δ 7.64 (s, 1H), 7.28-7.13 (m,5H), 6.91-6.72 (m, 8H), 4.27 (s, 2H), 3.92 (q, 2H), 3.25 (s, 2H), 3.15 (m, 2H), 2.52 (m, 2H), 1.31 (s, 9H), 1.21 (t, 3H). m/z: [M+H⁺] calcd for $C_{28}H_{34}N_2O_3$ 447.3. found 447.8.

b. Synthesis of Compound E.

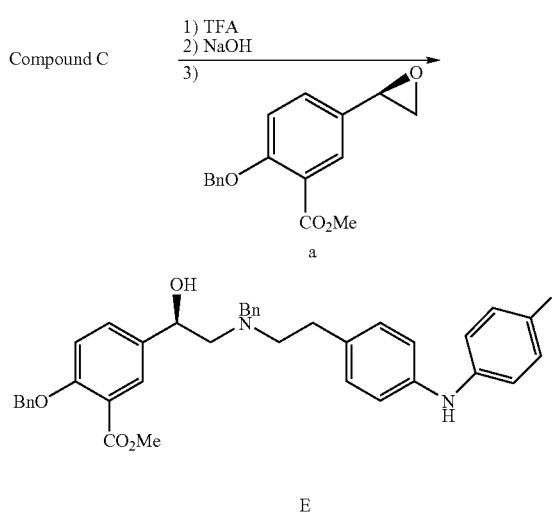

To 2.93 g (6.56 mmol) of compound C in 15 ml of CH$_2$Cl$_2$ at 0° C. was added 15 ml of trifluoroacetic acid. After 40 minutes, the solution was concentrated under reduced pressure, and the residue was partitioned between 1M NaOH and EtOAc. The phases were separated, and the EtOAc phase washed once each with water and brine, dried over Na$_2$SO$_4$, filtered, and concentrated to an orange oil. The oil was dissolved in 20 ml of isopropanol, 1.86 g (6.56 mmol) of the epoxide a was added, and the solution was heated at 78° C. overnight. The mixture was cooled to room temperature, and concentrated under reduced pressure to give compound E as an orange oil that was used without purification in the next step.

c. Synthesis of Compound F.

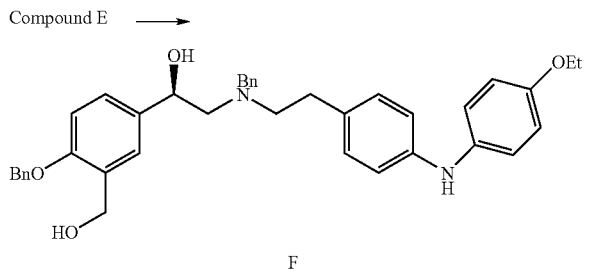

To 6.56 mmol of crude compound E from the previous step in 40 mL of tetrahydrofuran at 0° C. was added 16.4 mL (16.4 mmol) of 1M lithium aluminum hydride in tetrahydrofuran. After 2 hours, the reaction was quenched by slow addition of sodium sulfate decahydrate. The slurry was diluted with diethyl ether, dried over Na$_2$SO$_4$, filtered, and concentrated to an orange oil. The oil was purified by chromatography, using 50% EtOAc/50% hexanes as eluent, to give compound F as an off-white foam. $^1$H NMR (300 MHz, DMSO-d6) δ 7.61 (s, 1H), 7.37-6.71 (m, 21H), 5.02 (s, 2H), 4.94 (m, 1H), 4.67 (m, 1H), 4.55 (m, 1H), 4.48 (d, 2H), 3.85 (dd, 2H), 3.63 (dd, 2H), 2.53 (m, 6H), 1.21 (t, 3H).

The intermediate epoxide a can be prepared as described by R. Hett et al., *Tetrahedron Lett.*, 1994, 35, 9357-9378.

Example 38

Synthesis of N-{2-[4-(4-ethoxyphenyl)aminophenyl]ethyl}-(R)-2-hydroxy-2-(8-hydroxy-2(1H)-quinolinon-5-yl)ethylamine (38)

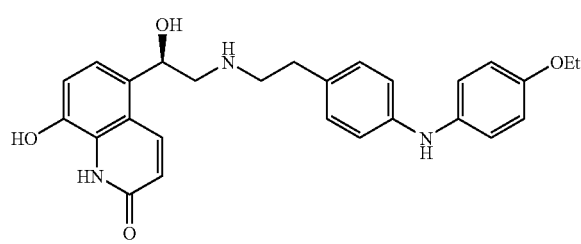

To a solution of 200 mg of compound Q (0.36 mmol) in 5.0 mL methanol was added 45 mg of 10% palladium on carbon. The reaction was placed under 1 atm H2 gas. After 20 h, an additional 25 mg of 10% palladium on carbon was added and the reaction was stirred under 1 atm H2 for an additional 24 h after which time the reaction was filtered. The filtrate was concentrated and purified by reversed phase preparative HPLC (gradient of 15-50% acetonitrile in 0.1% TFA). Fractions containing pure product were combined and lyophilized to afford a TFA salt of compound 6 as a powder. A sample of the TFA salt (39.7 mg) was dissolved in acetonitrile (1.0 mL), diluted with water (2.0 mL) and then 0.1 N HCl (5.0 mL). The solution was frozen and lyophilized to afford the hydrochloride salt of compound 38 (38.3 mg) as a yellow powder. $^1$H NMR (300 MHz, DMSO-d6) δ 10.5 (br s, 2H), 9.20 (br s, 1H), 8.75 (br s, 1H), 8.22 (d, 1H) 7.15 (d, 1H), 6.95-7.05 (m, 5H), 6.80-6.90 (m, 4H), 6.56 (d, 1H), 5.40 (dd, 1H), 3.95 (quar, 2H), 2.95-3.18 (m, 4H), 2.80-2.95 (m, 2H), 1.29 (t, 3H); m/z: [M+H$^+$] calcd for C$_{27}$H$_{29}$N$_3$O$_4$ 460.22. found 460.2.

The intermediate compound Q was prepared as follows.

a. Synthesis of Compound X.

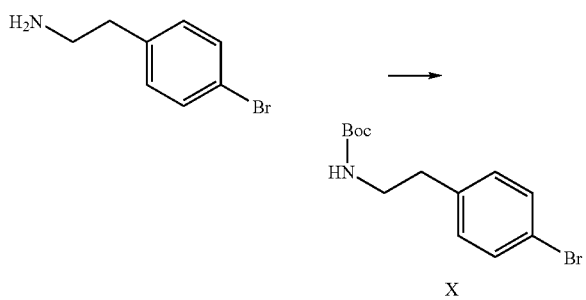

To 7.03 g (35.1 mmol) of 4-bromophenethylamine (Sigma-Aldrich) in 60 mL of THF was added 8.6 g (39.4 mmol) of di-tert-butyldicarbonate. After 10 minutes, the solution was concentrated under reduced pressure, and the residue was partitioned between saturated aqueous sodium bicarbonate and ethyl acetate. The ethyl acetate phase washed with brine, dried over MgSO$_4$, filtered, and concentrated to give compound X as a white solid.

b. Synthesis of Compound Y.

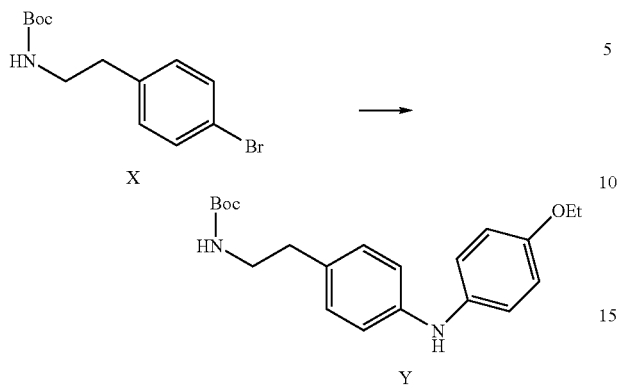

To a flask containing 1.2 g (4.1 mmol) of compound X, 0.72 g (5.3 mmol) of para-phenetidine (4-ethoxyaniline, Sigma-Aldrich), 0.19 g (0.35 mmol) of tris(dibenzylidineacetone)dipalladium(0), 0.38 g (0.61 mmol) of rac-2,2'-bis(diphenylphosphino)-1,1'-binaphthyl, and 0.51 g (5.3 mmol) of sodium tert-butoxide, was added 35 mL of toluene, and the mixture was heated at 95° C. for 16 hours under an nitrogen atmosphere. The mixture was partitioned between 1.0 M aqueous NaHSO$_4$ and diethyl ether. The diethyl ether phase washed once each with saturated NaHCO$_3$ and brine, dried over MgSO$_4$, filtered, and concentrated to a dark oil. The oil was purified by silica gel chromatography, using 15% EtOAc/85% hexanes as eluant, to give compound Y as a dark orange oil.

c. Synthesis of compound Q.

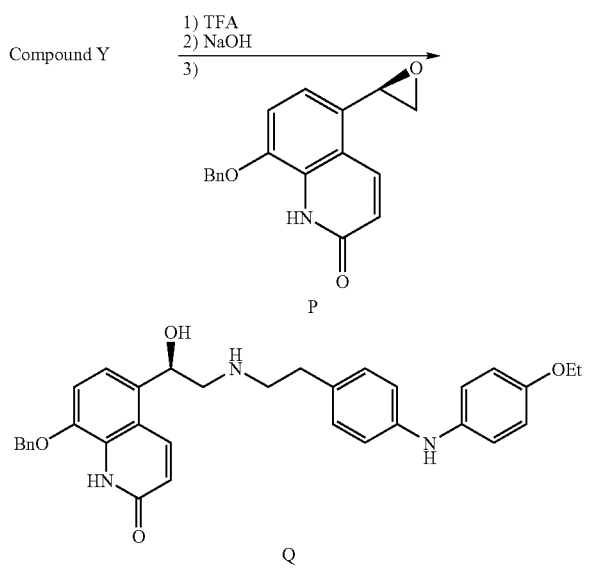

To 1.0 g of compound Y (2.8 mmol) in 5 mL CH$_2$Cl$_2$ was added 4 mL TFA. After 15 minutes, the solution was concentrated, diluted with 50 mL isopropyl acetate and washed twice with 1.0 M aqueous NaOH. The isopropyl acetate layer was dried over MgSO$_4$, filtered, and concentrated to a brown oil. The oil was dissolved in 5.0 mL of isopropanol and 390 mg (1.3 mmol) of epoxide P (Example 15, part a) were added. The solution was heated to 70° C. After 36 h, the solution was concentrated and the product purified by reversed phase HPLC (gradient of 20-70% acetonitrile in 0.1% TFA). Fractions containing pure product were combined and concentrated to remove acetonitrile. The aqueous residue was diluted with brine and extracted with ethyl acetate. The ethyl acetate layer was dried over MgSO$_4$ and concentrated to afford compound Q as a yellow foam.

Example 39

Synthesis of Compound 39

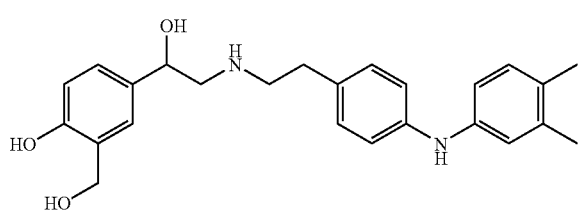

Using a coupling procedure similar to that described in Example 1, except replacing the N$^1$-(4-heptyl-6-methyl-2-pyrimidinyl)sulfanilamide with 3,4-dimethylaniline (available from Aldrich), a TFA salt of compound 39 was prepared.

Example 40

Synthesis of Compound 40

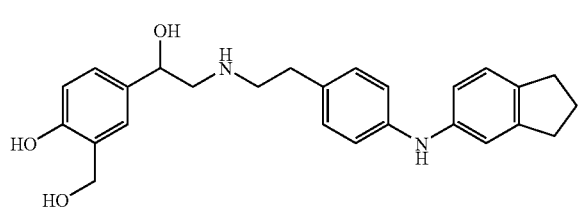

Using a coupling procedure similar to that described in Example 1, except replacing the N$^1$-(4-heptyl-6-methyl-2-pyrimidinyl)sulfanilamide with 5-aminoindan (available from Aldrich), a TFA salt of compound 40 was prepared.

Example 41

Synthesis of Compound 41

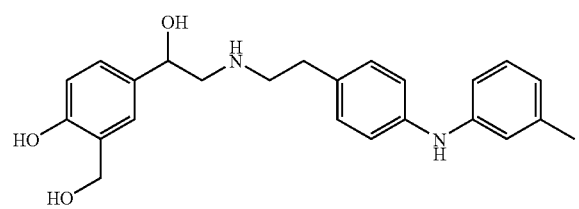

Using a coupling procedure similar to that described in Example 1, except replacing the $N^1$-(4-heptyl-6-methyl-2-pyrimidinyl)sulfanilamide with m-toluidine (available from Aldrich), a TFA salt of compound 41 was prepared.

Example 42

Synthesis of Compound 42

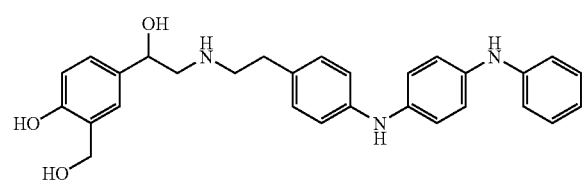

Using a coupling procedure similar to that described in Example 1, except replacing the $N^1$-(4-heptyl-6-methyl-2-pyrimidinyl)sulfanilamide with 4-aminodiphenylamine (available from Aldrich), a TFA salt of compound 42 was prepared.

Example 43

Synthesis of Compound 43

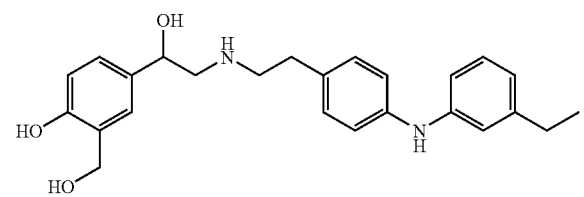

Using a coupling procedure similar to that described in Example 1, except replacing the $N^1$-(4-heptyl-6-methyl-2-pyrimidinyl)sulfanilamide with 3-ethylaniline (available from Aldrich), a TFA salt of compound 43 was prepared. m/z: [M+H$^+$] calcd for $C_{25}H_{30}N_2O_3$ 407.2. found 407.2.

Example 44

Synthesis of Compound 44

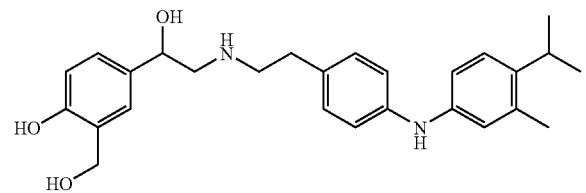

Using a coupling procedure similar to that described in Example 1, except replacing the $N^1$-(4-heptyl-6-methyl-2-pyrimidinyl)sulfanilamide with 3-methyl-4-isopropylaniline hydrochloride (available from Avocado Chemicals), a TFA salt of compound 44 was prepared. m/z: [M+H$^+$] calcd for $C_{27}H_{34}N_2O_3$ 435.3. found 435.2.

Example 45

Synthesis of Compound 45

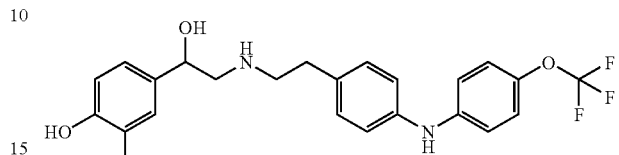

Using a coupling procedure similar to that described in Example 1, except replacing the $N^1$-(4-heptyl-6-methyl-2-pyrimidinyl)sulfanilamide with 4-(trifluoromethoxy)aniline (available from Aldrich), a TFA salt of compound 45 was prepared. m/z: [M+H$^+$] calcd for $C_{24}H_{25}F_3N_2O_4$ 463.2. found 463.2.

Example 46

Synthesis of Compound 46

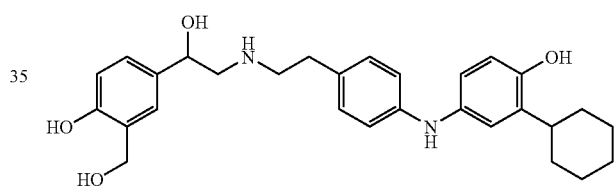

Using a coupling procedure similar to that described in Example 1, except replacing the $N^1$-(4-heptyl-6-methyl-2-pyrimidinyl)sulfanilamide with 4-amino-2-cyclohexylphenol (available from Sigma-Aldrich Library of Rare Chemicals), a TFA salt of compound 46 was prepared. m/z: [M+H$^+$] calcd for $C_{29}H_{36}N_2O_4$ 477.3. found 477.2.

Example 47

Synthesis of Compound 47

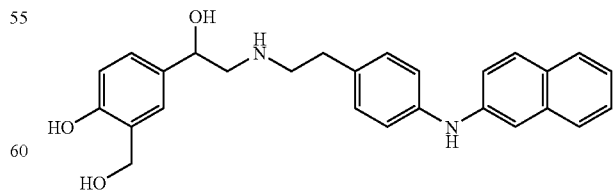

Using a coupling procedure similar to that described in Example 1, except replacing the $N^1$-(4-heptyl-6-methyl-2-pyrimidinyl)sulfanilamide with 2-naphthylamine (available from Aldrich), a TFA salt of compound 47 was prepared.

Example 48

Synthesis of N-{2-[4-(3-phenylphenyl)aminophenyl]ethyl}-2-hydroxy-2-(3-hydroxymethyl-4-hydroxyphenyl)ethylamine (48)

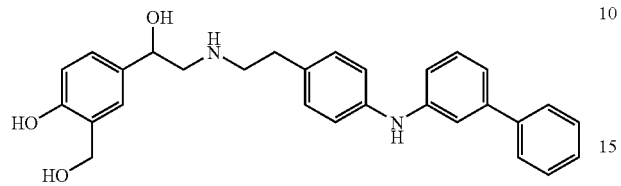

Using a coupling procedure similar to that described in Example 1, except replacing the N¹-(4-heptyl-6-methyl-2-pyrimidinyl)sulfanilamide with 3-aminobiphenyl (available from Trans World Chemicals, Inc.), a TFA salt of compound 48 was prepared.

Example 49

Synthesis of N-{2-[4-(3-phenyl-4-methoxyphenyl)aminophenyl]ethyl}-2-hydroxy-2-(3-hydroxymethyl-4-hydroxyphenyl)ethylamine (49)

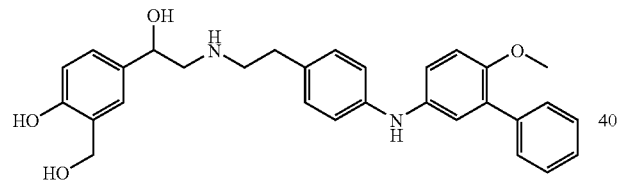

Using a coupling procedure similar to that described in Example 1, except replacing the N¹-(4-heptyl-6-methyl-2-pyrimidinyl)sulfanilamide with 3-phenyl-p-anisidine hydrochloride (available from Trans World Chemicals, Inc.), a TFA salt of compound 49 was prepared.

Example 50

Synthesis of Compound 50

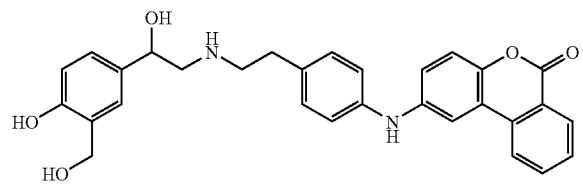

Using a coupling procedure similar to that described in Example 1, except replacing the N¹-(4-heptyl-6-methyl-2-pyrimidinyl)sulfanilamide with 6-amino-3,4-benzocoumarin (available from Aldrich), a TFA salt of compound 50 was prepared. m/z: [M+H⁺] calcd for $C_{30}H_{28}N_2O_5$ 497.2. found 497.1.

Example 51

Synthesis of Compound 51

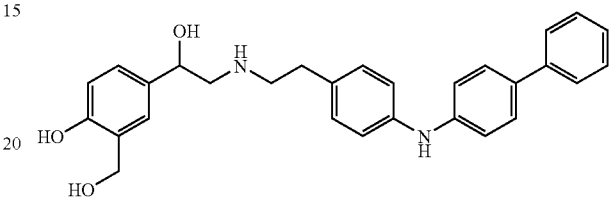

Using a coupling procedure similar to that described in Example 1, except replacing the N¹-(4-heptyl-6-methyl-2-pyrimidinyl)sulfanilamide with 4-aminobiphenyl (available from Aldrich), a TFA salt of compound 51 was prepared. m/z: [M+H⁺] calcd for $C_{29}H_{30}N_2O_3$ 455.2. found 455.2.

Example 52

Synthesis of N-{2-[4-(3-phenyl-4-methoxyphenyl)aminophenyl]ethyl}-(R)-2-hydroxy-2-(3-hydroxymethyl-4-hydroxyphenyl)ethylamine (52)

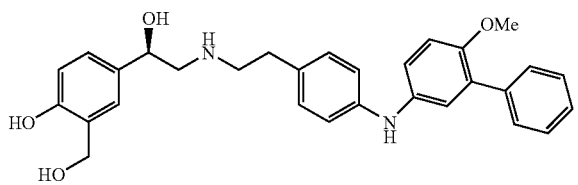

To 2.0 g (3.10 mmol) of compound H in 50 mL of ethanol was added 0.70 g of 10% palladium on carbon under a stream of nitrogen. The flask was fitted with a balloon of hydrogen gas, and the reaction was vigorously stirred for 1.5 hours. The reaction was filtered through celite, using methanol to rinse, and the filtrate was concentrated under reduced pressure. The residue was dissolved in 20 mL isopropanol, 1.65 mL of 4.0 N HCl in dioxane was added, and the product was precipitated by adding the solution to a large volume of diethyl ether. The solids were isolated by filtration to give 1.43 g (80%) of a hydrochloride salt of compound 52 as a white solid. ¹H NMR (300 MHz, DMSO-d6) δ 9.4 (b, 1H), 9.01 (br s, 1H), 8.65 (br s, 1H), 7.39-7.22 (m, 6H), 6.99-6.83 (m, 8H), 6.69 (d, 1H), 5.45 (br, 4H), 4.77 (m, 1H), 4.39 (s, 2H), 3.62 (s, 3H), 3.02-2.78 (m, 6H). m/z: [M+H⁺] calcd for $C_{30}H_{32}N_2O_4$ 485.2. found 485.4.

The intermediate compound H was prepared as follows.

a. Synthesis of Compound D.

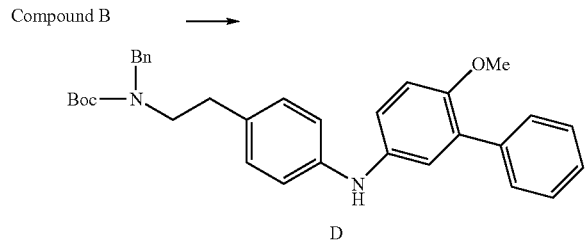

To a flask containing 3.91 g (10 mmol) of compound B (Example 13, part b), 3.06 g (13 mmol) of 4-methoxy-3-phenylaniline hydrochloride (from TCI), 0.46 g (0.5 mmol) of tris(dibenzylidineacetone)dipalladium(0), 0.93 g (1.5 mmol) of racemic-2,2'-bis(diphenylphosphino)-1,1'-binaphthyl, and 2.21 g (23 mmol) of sodium tert-butoxide was added 50 mL of toluene, and the mixture was heated at 95° C. for 5.5 hours under an nitrogen atmosphere. The mixture was partitioned between 1.0 M aqueous NaHSO$_4$ and diethyl ether, and the phases were separated. The diethyl ether phase was diluted with one volume of hexanes, and washed once each with 1.0 M aqueous NaHSO$_4$ and brine, dried over Na$_2$SO$_4$, filtered, and concentrated to a dark oil. The oil was purified by silica gel chromatography, using 12% EtOAc/88% hexanes as eluent, to give compound D as a yellow foam. $^1$H NMR (300 MHz, DMSO-d6) δ 7.76 (s, 1H), 7.38-7.13 (m, 10H), 6.95-6.81 (m, 7H), 4.28 (s, 2H), 3.61 (s, 3H), 3.16 (m, 2H), 2.53 (m, 2H), 1.29 (s, 9H).

b. Synthesis of Compound G.

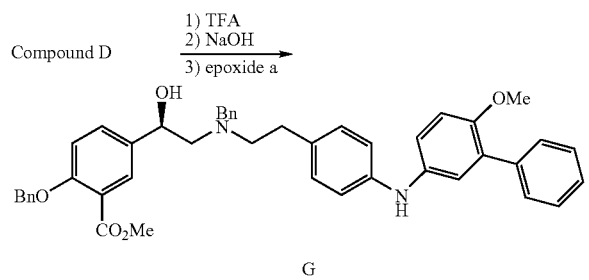

To 2.60 g (5.11 mmol) of compound D in 15 mL of CH$_2$Cl$_2$ at 0° C. was added 15 mL of trifluoroacetic acid. After 40 minutes, the solution was concentrated under reduced pressure, and the residue was partitioned between 1M aqueous NaOH and EtOAc. The phases were separated, and the EtOAc phase washed once each with water and brine, dried over Na$_2$SO$_4$, filtered, and concentrated to an orange residue. The residue was dissolved in 15 mL of isopropanol, 1.45 g (5.11 mmol) of the epoxide a (Example 37, part b) was added, and the solution was heated at 78° C. overnight. The mixture was cooled to room temperature, and concentrated under reduced pressure to give compound G as an orange oil which was used in the next step without purification.

c. Synthesis of Compound H.

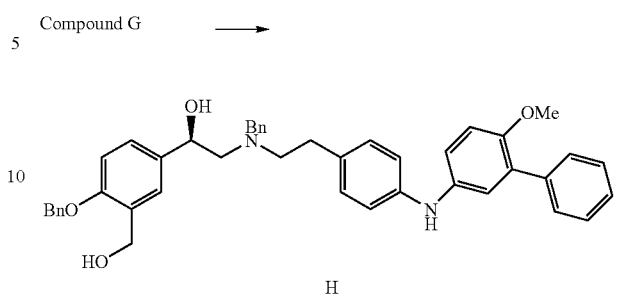

To 5.11 mmol of crude compound G from the previous step in 40 mL of tetrahydrofuran at 0° C. was added 12.7 mL (12.7 mmol) of 1.0 M lithium aluminum hydride in tetrahydrofuran. After 2 hours, the reaction was quenched by slow addition of sodium sulfate decahydrate. The slurry was diluted with diethyl ether, dried over Na$_2$SO$_4$, filtered, and concentrated to an orange oil. The oil was purified by chromatography, using 50% EtOAc/50% hexanes as eluent, to give 2.0 g (61%, 2 steps) of compound H as a white foam. $^1$H NMR (300 MHz, DMSO-d6) δ 7.72 (s, 1H), 7.38-6.77 (m, 25H), 5.00 (s, 2H), 4.92 (m, 1H), 4.65 (m, 1H), 4.55 (m, 1H), 4.45 (d, 2H), 3.62 (s, 2H), 3.61 (s, 3H), 2.52 (m, 6H).

Example 53

Synthesis of N-{2-[4-(3-phenyl-4-ethoxyphenyl)aminophenyl]ethyl}-(R)-2-hydroxy-2-(3-hydroxymethyl-4-hydroxyphenyl)ethylamine (53)

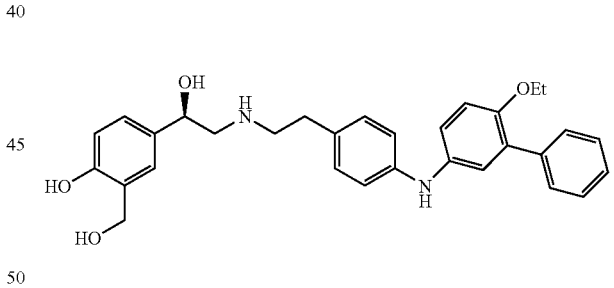

To a mixture of 825 mg (1.22 mmol) of compound N in 15 mL of ethanol was added 260 mg of 10% palladium on carbon under a stream of nitrogen. The flask was fitted with a balloon of hydrogen gas, and the reaction was vigorously stirred for 3 hours. The reaction was filtered through celite, using methanol to rinse, and the filtrate was concentrated under reduced pressure. The residue was dissolved in 10 mL isopropanol, 0.67 mL of 4.0 M HCl in dioxane was added, and the product was precipitated by adding the solution to a large volume of EtOAc. The solids were isolated by filtration to give a hydrochloride salt of compound 53 as a white solid. m/z: [M+H$^+$] calcd for C$_{31}$H$_{32}$N$_2$O$_4$ 499.3. found 499.3.

The intermediate compound N was prepared as follows.

a. Synthesis of Compound J.

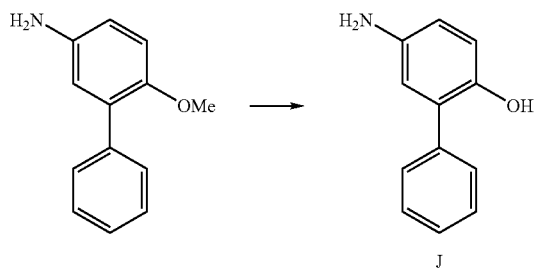

4.84 g (20.5 mmol) of 4-methoxy-3-phenylaniline hydrochloride (available from TCI) was partitioned between diethyl ether and 1.0 M aqueous NaOH, and the phases were separated. The diethyl ether phase washed once each with water and brine, dried over $K_2CO_3$, filtered, and concentrated to a brown solid. The solid was dissolved in 100 mL of $CH_2Cl_2$, the solution was cooled to 0° C., and 21.2 g (84.6 mmol) of boron tribromide was added. After 20 minutes, the reaction was poured over 500 mL of ice, and the mixture was stirred overnight. The mixture washed twice with EtOAc to remove oxidized material, and the EtOAc phases were discarded. The acidic phase was basified with solid $NaHCO_3$, and was extracted twice with EtOAc. The combined EtOAc phases were washed once with brine, dried over $Na_2SO_4$, filtered, and concentrated to give 2.48 g of compound J as a brown solid. $^1$H NMR (300 MHz, DMSO-d6) δ 8.37 (s, 1H), 7.41-7.14 (m, 5H), 6.57-6.32 (m, 3H), 4.45 (s, 2H).

b. Synthesis of Compound K.

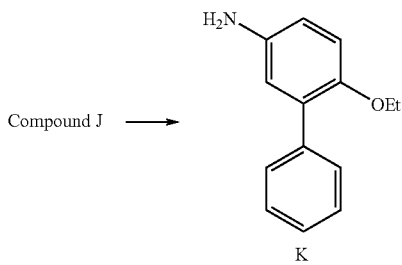

To 2.28 g (12.2 mmol) of compound J in 45 mL of dimethylformamide at 0° C. was added 734 mg (18.4 mmol) of 60% NaH in oil. After 10 minutes, 1.90 g (12.2 mmol) of iodoethane was added. After 20 minutes, the solution was partitioned between diethyl ether and 5% aqueous $Na_2SO_3$, and the phases were separated. The diethyl ether phase washed once each with 1.0 M aqueous NaOH, water, and brine, dried over $Na_2SO_4$, and concentrated to give compound K as a dark brown oil. $^1$H NMR (300 MHz, DMSO-d6) δ 7.37-7.19 (m, 5H), 6.73 (d, 1H), 6.47-6.42 (m, 2H), 4.65 (s, 2H), 3.73 (q, 2H), 1.07 (t, 3H).

c. Synthesis of Compound L.

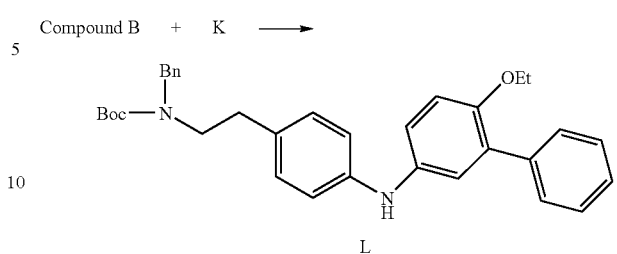

To a flask containing 3.97 g (10.7 mmol) of compound B (Example 13, part b), 2.27 g (12.2 mmol) of compound K, 0.46 g (0.5 mmol) of tris(dibenzylidineacetone)dipalladium (0), 0.95 g (1.5 mmol) of racemic-2,2'-bis(diphenylphosphino)-1,1'-binaphthyl, and 1.27 g (13.3 mmol) of sodium tert-butoxide was added 48 mL of toluene, and the mixture was heated at 95° C. for 5.5 hours under an nitrogen atmosphere. The mixture was partitioned between 1.0 M aqueous $NaHSO_4$ and diethyl ether, and the phases were separated. The diethyl ether phase was diluted with one volume of hexanes, and washed once each with 1.0 M aqueous $NaHSO_4$ and brine, dried over $Na_2SO_4$, filtered, and concentrated to a dark oil. The oil was purified by silica gel chromatography, using 10% EtOAc/90% hexanes as eluent, to give 4.13 g (77%) of compound L as a yellow foam. $^1$H NMR (300 MHz, DMSO-d6) δ 7.76 (s, 1H), 7.42-7.13 (m, 10H), 6.93-6.81 (m, 7H), 4.27 (s, 2H), 3.86 (q, 2H), 3.25 (m, 2H), 2.53 (m, 2H), 1.28 (s, 9H), 1.13 (t, 3H).

d. Synthesis of Compound M.

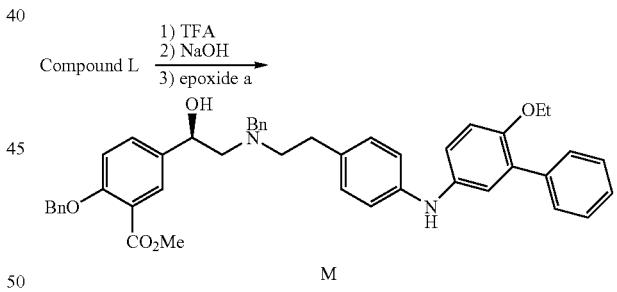

To 1.40 g (2.68 mmol) of compound L in 15 mL of $CH_2Cl_2$ at 0° C. was added 15 mL of trifluoroacetic acid. After 40 minutes, the solution was concentrated under reduced pressure, and the residue was partitioned between 1.0 M aqueous NaOH and EtOAc. The phases were separated, and the EtOAc phase washed once each with water and brine, dried over $Na_2SO_4$, filtered, and concentrated to an orange residue. The residue was dissolved in 15 mL of isopropanol, 1.45 g (2.68 mmol) of the epoxide a (Example 37, part b) was added, and the solution was heated at 78° C. overnight. The mixture was cooled to room temperature, and concentrated under reduced pressure to give an orange oil that was taken on without analysis.

e. Synthesis of Compound N.

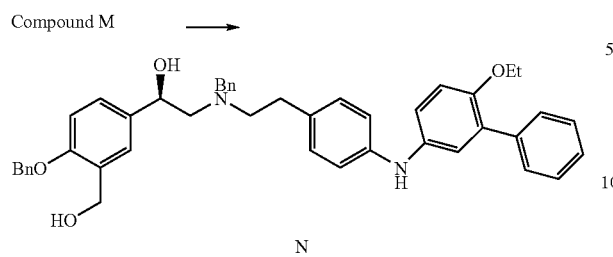

N

To 2.68 mmol of crude compound M in 20 mL of tetrahydrofuran at 0° C. was added 7.0 mL (7.0 mmol) of 1.0 M lithium aluminum hydride in tetrahydrofuran. After 2 hours, the reaction was quenched by slow addition of sodium sulfate decahydrate. The slurry was diluted with diethyl ether, dried over $Na_2SO_4$, filtered, and concentrated to an orange oil. The oil was purified by silica gel chromatography, using 50% EtOAc/50% hexanes as eluent, to give 835 mg of compound N as a white foam. $^1$H NMR (300 MHz, DMSO-d6) δ 7.73 (s, 1H), 7.42-6.77 (m, 25H), 5.00 (s, 2H), 4.93 (m, 1H), 4.66 (d, 1H), 4.51 (m, 1H), 4.47 (m, 2H), 3.86 (q, 2H), 3.62 (m, 2H), 2.55 (m, 6H), 1.13 (t, 3H).

Example 54

Synthesis of N-{2-[4-(3-phenyl-4-methoxyphenyl)aminophenyl]ethyl}-(R)-2-hydroxy-2-(3-formamido-4-hydroxyphenyl)ethylamine (54)

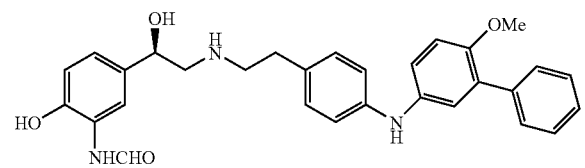

To a mixture of 1.24 g (1.83 mmol) of compound I in 30 mL of ethanol and 20 mL of methanol was added 400 mg of 10% palladium on carbon under a stream of nitrogen. The flask was fitted with a balloon of hydrogen gas, and the reaction was vigorously stirred for 1.5 hours. The reaction was filtered through celite, using methanol to rinse, and the filtrate was concentrated under reduced pressure. The residue was dissolved in 20 mL isopropanol, 0.21 mL of 4.0 M HCl in dioxane was added, and the product was precipitated by adding the solution to a large volume of EtOAc. The solids were isolated by filtration to give 447 mg of a hydrochloride salt of compound 54 as a white solid. $^1$H NMR (300 MHz, DMSO-d6) δ 10.03 (br s, 1H), 9.55 (s, 1H), 8.81 (br s, 1H), 8.59 (br s, 1H), 8.20 (d, 1H), 8.07 (d, 1H), 7.39-7.20 (m, 5H), 6.99-6.79 (m, 10H), 4.75 (m, 1H), 3.62 (s, 3H), 3.03-2.72 (m, 6H). m/z: [M+H$^+$] calcd for $C_{30}H_{31}N_3O_4$ 498.2. found 498.5.

The intermediate compound I was prepared as follows.

a. Synthesis of Compound I.

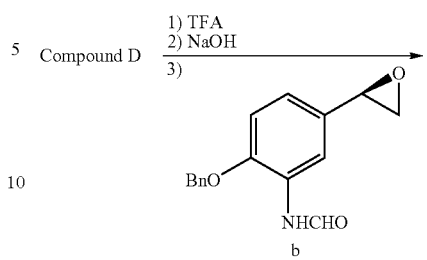

b

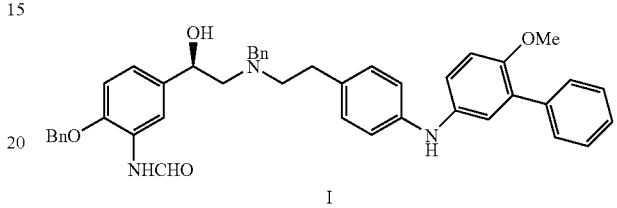

I

To 944 mg (1.85 mmol) of compound D (Example 52, part a) in 6 mL of $CH_2Cl_2$ at 0° C. was added 6 mL of trifluoroacetic acid. After 40 minutes, the solution was concentrated under reduced pressure, and the residue was partitioned between 1.0 M aqueous NaOH and EtOAc. The phases were separated, and the EtOAc phase washed once each with water and brine, dried over $Na_2SO_4$, filtered, and concentrated to an orange oil.

The residue from above was dissolved in 5 mL of isopropanol, 500 mg (1.85 mmol) of the epoxide b was added, and the solution was heated at 78° C. overnight. The mixture was cooled to room temperature, and concentrated under reduced pressure to give an orange oil. The oil was purified by silica gel chromatography, using 50 EtOAc/50 hexanes as eluent, to give 825 mg (66%) of compound I as a white foam. $^1$H NMR (300 MHz, DMSO-d6) δ 9.45 (s, 1H), 8.24 (d, 1H), 8.09 (d, 1H), 7.72 (s, 1H), 7.42-6.77 (m, 25H), 5.09 (s, 2H), 4.49 (m, 1H), 3.67 (m, 2H), 3.61 (s, 3H), 2.50 (m, 6H).

The intermediate epoxide b can be prepared as described in U.S. Pat. No. 6,268,533 B1, and in R. Hett. et al., *Organic Process Research and Development*, 1998, 2, 96-99.

Example 55

Synthesis of N-{2-[4-(3-phenyl-4-ethoxyphenyl)aminophenyl]ethyl}-(R)-2-hydroxy-2-(3-formamido-4-hydroxyphenyl)ethylamine (55)

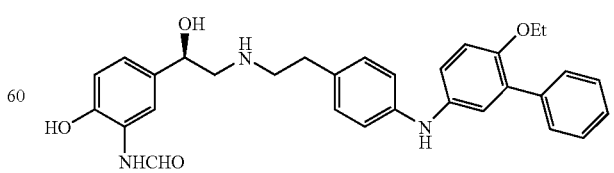

To a mixture of 746 mg (1.07 mmol) of compound O in 15 mL of ethanol and 5 mL of EtOAc was added 260 mg of 10% palladium on carbon under a stream of nitrogen. The flask was fitted with a balloon of hydrogen gas, and the reaction was vigorously stirred for 3 hours. The reaction was filtered through celite, using methanol to rinse, and the filtrate was concentrated under reduced pressure. The residue was dissolved in 20 mL isopropanol, 0.58 mL of 4.0 M HCl in dioxane was added, and the product was precipitated by adding the solution to a large volume of EtOAc. The solids were isolated by filtration to give a hydrochloride salt of compound 55 as an off white solid. $^1$H NMR (300 MHz, DMSO-d6) δ 10.12 (br s, 1H), 9.62 (s, 1H), 8.90 (br s, 1H), 8.67 (br s, 1H), 8.27 (d, 1H), 8.14 (d, 1H), 7.25 (m, 5H) 6.85-7.08 (m, 9H), 4.80 (dd, 1H), 3.94 (quar, 2H), 2.75-3.15 (m, 6H), 1.21 (t, 3H); m/z: [M+H$^+$] calcd for $C_{31}H_{33}N_3O_4$ 512.25. found 512.5.

The intermediate compound O was prepared as follows.

a. Synthesis of Compound O.

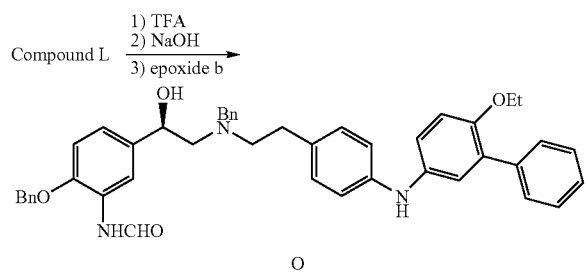

To 1.4 g (2.68 mmol) of compound L (Example 53, part c) in 6 mL of CH$_2$Cl$_2$ at 0° C. was added 6 mL of trifluoroacetic acid. After 40 minutes, the solution was concentrated under reduced pressure, and the residue was partitioned between 1.0 M aqueous NaOH and EtOAc. The phases were separated, and the EtOAc phase washed once each with water and brine, dried over Na$_2$SO$_4$, filtered, and concentrated to an orange residue. The residue was dissolved in 5 mL of isopropanol, 721 mg (2.68 mmol) of epoxide b (Example 54, part a) was added, and the solution was heated at 78° C. overnight. The mixture was cooled to room temperature, and concentrated under reduced pressure to give an orange oil. The oil was purified by silica gel chromatography using 50 EtOAc/50 hexanes as eluent, to give 756 mg of compound O as a white foam. $^1$H NMR (300 MHz, DMSO-d6) δ 9.45 (d, 1H), 8.25 (d, 1H), 8.14 (d, 1H), 7.72 (s, 1H), 7.45-6.76 (m, 25H), 5.10 (s, 2H), 5.04 (m, 1H), 3.94 (q, 2H), 3.61 (s, 2H), 2.50 (s, 6H), 1.13 (t, 3H).

Example 56

Synthesis of N-{2-[4-(3-phenyl-4-methoxyphenyl) aminophenyl]ethyl}-2-hydroxy-2-(8-hydroxy-2(1H)-quinolinon-5-yl)ethylamine (56)

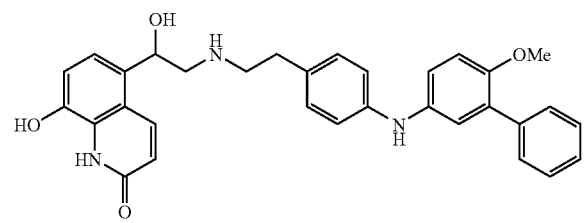

To a solution of 840 mg of compound S (1.2 mmol) in 40 mL of 1:1 methanol:THF was added 170 mg of 10% palladium on carbon. The reaction was shaken under an atmosphere of 35 psi H$_2$. After 24 h, the reaction was filtered and the filtrate purified by reversed-phase HPLC (gradient of 10 to 70% acetonitrile in 0.1% aqueous TFA). Fractions containing pure product were combined and lyophilized to afford a TFA salt of compound 56 as a powder.

A sample of the TFA salt (75 mg) was dissolved in acetonitrile (1.0 mL) and diluted with water (2.0 mL) followed by 0.1 N HCl (3.0 mL). The solution became cloudy. Addition of 1.5 mL acetonitrile afforded a clear solution which was frozen and lyophilized. The residue was redissolved in acetonitrile (1.0 mL) and diluted with water (2.0 mL) followed by 0.1 N HCl (4.0 mL). The solution became cloudy. Addition of 1.0 mL acetonitrile afforded a clear solution which was frozen and lyophilized. The hydrochloride salt of compound 56 (50 mg) was obtained as a gray solid. $^1$H NMR (300 MHz, DMSO-d6) δ 10.55 (br s, 1H), 9.30 (br s, 1H), 8.80, (br s, 1H), 8.24 (d, 1H), 7.25-7.48 (m, 5H), 6.92-7.18 (m 9H), 6.55 (d, 1H), 5.55 (d, 1H), 3.69 (s, 3H), 2.80-3.20 (m, 6H) m/z: [M+H$^+$] calcd for $C_{32}H_{31}N_3O_4$ 522.24. found 522.3.

The intermediate compound S was prepared as follows.

a. Synthesis of Compound S.

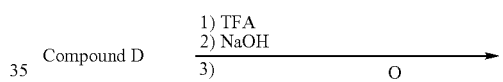
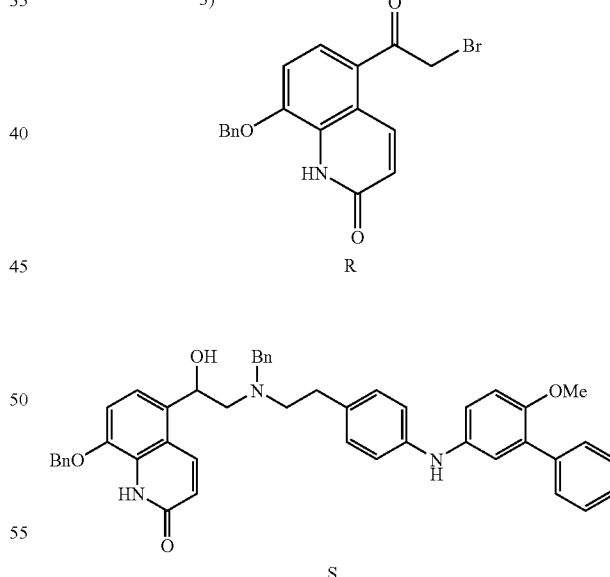

A solution of compound D (800 mg, 1.6 mmol, Example 52, part a) in 5 mL CH$_2$Cl$_2$ was cooled to 0° C. and 5 mL of TFA was added. After 20 min, the reaction was concentrated and the residue dissolved in ethyl acetate. The ethyl acetate solution was washed twice with 1.0 M aqueous NaOH followed by water and then dried over MgSO$_4$, filtered and concentrated to an oil. The oil was dissolved in 3 mL DMF and bromoketone R (800 mg, 2.1 mmol) and K$_2$CO$_3$ (650 mg, 4.7 mmol) were added. The reaction was heated to 40° C. After 1 h, the reaction was cooled and diluted with 5 mL methanol. NaBH$_4$ (150 mg, 4.0 mmol) was added and the reaction was stirred vigorously for 10 min. The reaction was quenched by dripping the suspension into 100 mL of rapidly stirred saturated aqueous NH$_4$Cl. Compound S precipitated and was isolated by filtration, washed with water and dried.

The intermediate bromoketone R can be prepared as described in Example 61B, parts a-d. See also EP 0 147 791 B.

Example 57

Synthesis of Compound 57

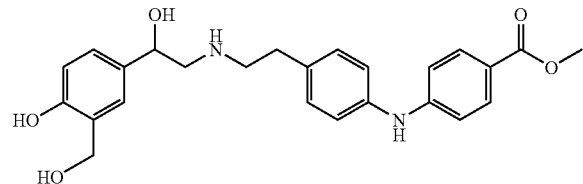

Using a coupling procedure similar to that described in Example 1, except replacing the N$^1$-(4-heptyl-6-methyl-2-pyrimidinyl)sulfanilamide with methyl-4-aminobenzoate (available from Aldrich), a TFA salt of compound 57 was prepared. m/z: [M+H$^+$] calcd for C$_{25}$H$_{28}$N$_2$O$_5$ 437.2. found 437.2.

Example 58

Synthesis of Compound 58

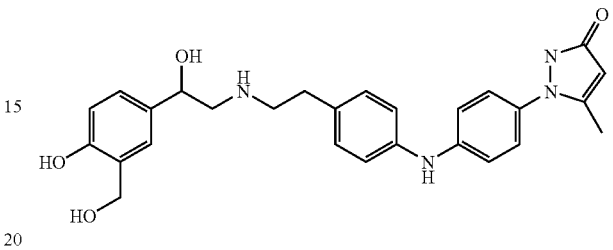

Using a coupling procedure similar to that described in Example 1, except replacing the N$^1$-(4-heptyl-6-methyl-2-pyrimidinyl)sulfanisamide with 2-(4-aminophenyl)-3-methyl-3-pyrazolin-5-one (available from Sigma-Aldrich Library of Rare Chemicals), a TFA salt of compound 58 was prepared. m/z: [M+H$^+$] calcd for C$_{27}$H$_{30}$N$_4$O$_4$ 475.2. found 475.2.

Example 59

Synthesis of Compound 59

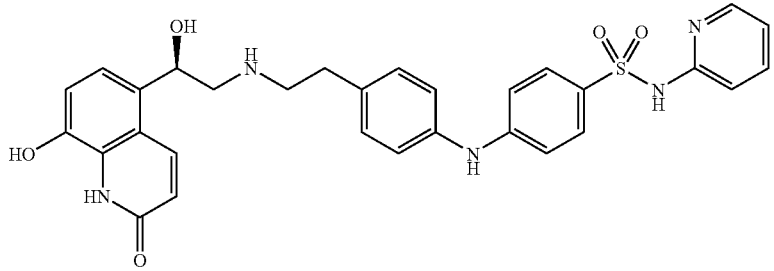

To a mixture of compound jj (0.2 g, 0.27 mmol) in 6 mL DMF/EtOH (1:1) was added 50 mg of 10% palladium on carbon. The reaction was agitated under H$_2$ at 40 psi for 8 hours. The slurry was filtered and purified by reversed phase HPLC (gradient of 10 to 50% acetonitrile in 0.1% aqueous TFA). Fractions containing pure product were combined and lyophilized to afford compound 59 as a TFA salt. The TFA salt product was solubilized in acetonitrile/water (1:1, 2 mL) to which 1.5 mL of 0.1 N aqueous HCl was added. The solution was frozen and lyophilized to afford compound 59 as an HCl salt. m/z: [M+H$^+$] calcd for C$_{30}$H$_{29}$N$_5$O$_5$S 572.7. found 572.3.

The intermediate jj was prepared as follows.

a. Synthesis of Compound jj

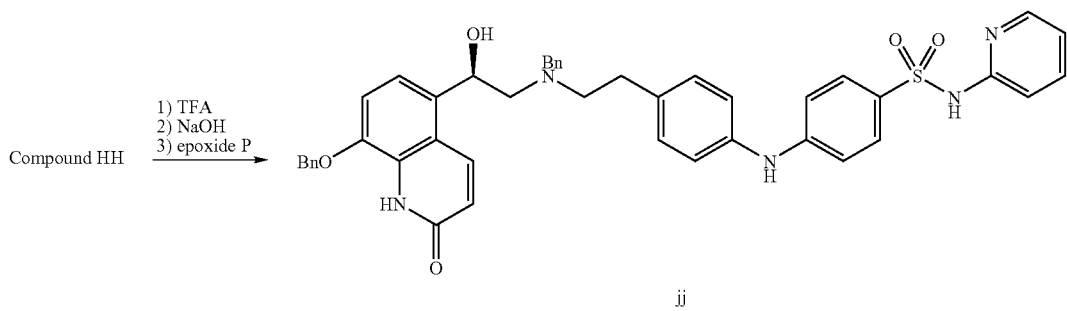

jj

To compound HH (4.5 g, 8.1 mmol) (Example 14, part a), in 20 ml CH$_2$Cl$_2$ was added 1.5 mL TFA. After 1 hour, the solution was concentrated, basified with 1.0 N aqueous sodium hydroxide and extracted twice with CH$_2$Cl$_2$, followed by an extraction using ethyl acetate. The organic layers were combined, dried over MgSO$_4$, filtered and concentrated to an oil. The oil was purified by silica gel chromatography (gradient of 2 to 10% methanol in methylene chloride). To the purified product (0.42 g, 0.92 mmol) was added epoxide P (Example 15, part a) (022 g, 0.76 mmol) and isopropanol (410 mL). The slurry was stirred at 70° C. Methylene chloride was added until a homogenous solution was obtained. After 40 h, the reaction was cooled to room temperature and the solvents were evaporated under reduced pressure. The residue was purified by silica gel chromatography (2% methanol in methylene chloride) to afford compound jj.

Example 60

Synthesis of Compound 60

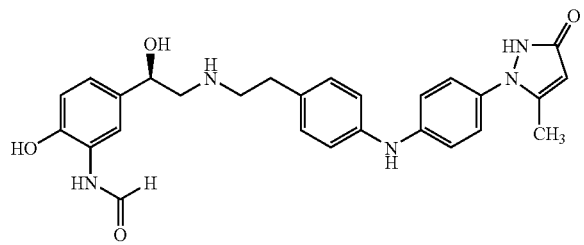

To a mixture of compound pp (0.3 g, 0.45 mmol) in 10 mL anhydrous EtOH was added 100 mg of 10% palladium on carbon. The reaction was agitated under H$_2$ at 40 psi for 18 h. The reaction was filtered and purified by reversed phase HPLC (gradient of 10 to 50% acetonitrile in 0.1% aqueous TFA). Fractions containing pure product were combined and lyophilized to afford compound 60 as a TFA salt. The TFA salt product was solubilized in acetonitrile/water (1:2, 100 mL) to which 6 mL of 0.1 N aqueous HCl was added. The solution was frozen and lyophilized to afford compound 60 as an HCl salt. m/z: [M+H$^+$] calcd for C$_{27}$H$_{29}$N$_5$O$_4$ 488.6. found 488.3.

The intermediate compound pp was prepared as follows.

a. Synthesis of Compound cc

Compound B ⟶

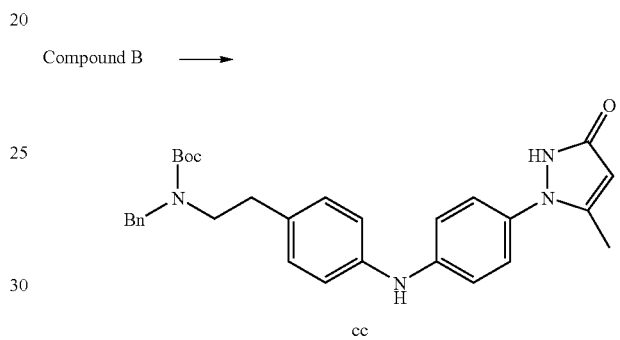

cc

To a flask containing compound B (Example 13, part b) (3.75 g, 9.6 mmol), 2-(4-aminophenyl)-3-methyl-3-pyrazolin-5-one (2.0 g, 10.6 mmol) (available from Sigma-Aldrich Library of Rare Chemicals), tris(dibenzylidineacetone)dipalladium(0) (0.44 g, 0.48 mmol), racemic-2,2'-bis(diphenylphosphino)-1,1'-binaphthyl (0.90 g, 1.44 mmol), and sodium tert-butoxide (2.20 g, 12.5 mmol) was added toluene (50 mL). The mixture was stirred at 95° C. for 6 h under a nitrogen atmosphere. The mixture was diluted with 200 mL diethyl ether and washed twice with 100 mL portions of 1.0 M aqueous NaHSO$_4$, followed by 100 mL of saturated aqueous NaHCO$_3$. The diethyl ether phase was dried over MgSO$_4$, filtered, and concentrated to a dark oil. The oil was purified by silica gel chromatography (gradient of 30 to 40% ethyl acetate in hexanes) to afford compound cc as an orange foam.

b. Synthesis of Compound pp.

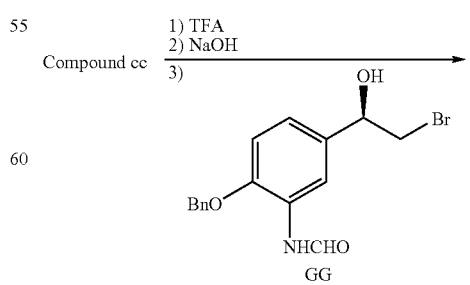

GG

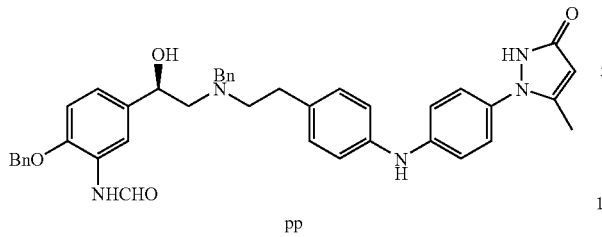

pp

To compound cc (0.99 g, 1.99 mmol) in 5 mL CH$_2$Cl$_2$ was added 2 mL TFA. After 1 h, the solution was concentrated, diluted with 15 mL CH$_2$Cl$_2$ and washed with 1.0 N aqueous sodium hydroxide. The aqueous was collected and washed again with CH$_2$Cl$_2$ (10 mL) followed by a wash with ethyl acetate (10 mL). The organic layers were combined and dried over MgSO$_4$, filtered, and concentrated under reduced pressure. The crude product was purified by silica gel chromatography (gradient of 2-10% MeOH in CH$_2$Cl$_2$) to afford an oil (2.1 g). A portion of this product (0.5 g, 1.26 mmol) was solubilized in 10 mL of 1:1 methanol:THF. Bromohydrin GG (Example 13, part d) (0.42 g, 1.20 mmol) and K$_2$CO$_3$ (0.44 g, 3.15 mmol) were added and the slurry was stirred at room temperature for 1.5 h. The reaction was concentrated and the residue was diluted with 30 mL water and extracted twice with 30 mL portions of toluene. The toluene extracts were combined, dried over Na$_2$SO$_4$, filtered, and concentrated. The residue was heated to 120° C. After 2 h, the reaction was cooled to room temperature and the crude compound was purified by silica gel chromatography (gradient of 5-10% MeOH in CH$_2$Cl$_2$) to afford compound pp as a tan colored solid (0.7 g).

Example 61A

Synthesis of N-{2-[4-(3-phenyl-4-methoxyphenyl)aminophenyl]ethyl}-(R)-2-hydroxy-2-(8-hydroxy-2(1H)-quinolinon-5-yl)ethylamine (61)

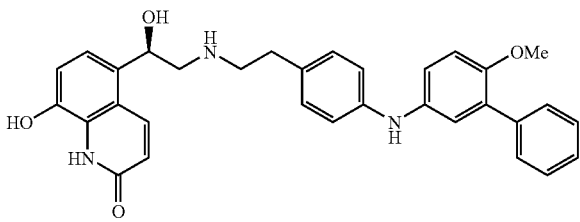

To a solution of 200 mg of compound T (0.28 mmol) in 4 mL of acetic acid was added 100 mg of 10% palladium on carbon. The reaction was shaken under an atmosphere of 40 psi H$_2$. After 17 h, the reaction was filtered and the filtrate purified by reversed-phase HPLC (gradient of 10 to 70% acetonitrile in 0.1% aqueous TFA). Fractions containing pure product were combined and lyophilized to afford compound 61 as a powder.

The intermediate compound T was prepared as follows:

a. Synthesis of Compound T

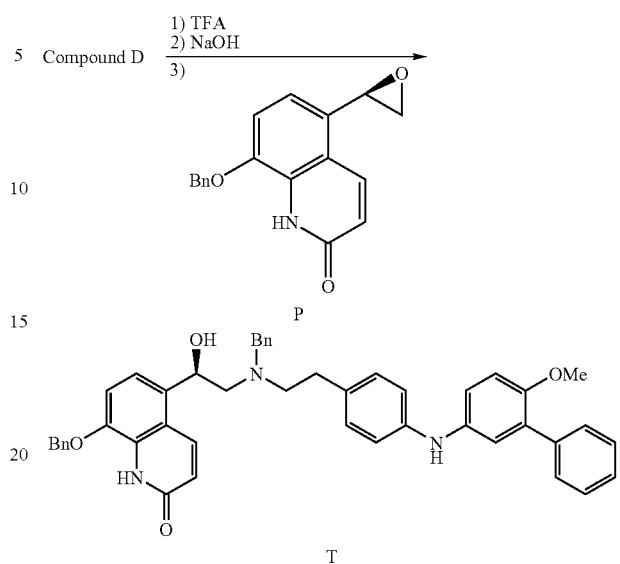

To 1.13 g of compound D (2.2 mmol, Example 52, part a) in 4 mL CH$_2$Cl$_2$ was added 4 mL TFA. After 30 minutes, the solution was concentrated and diluted with 20 mL ethyl acetate and 20 mL water. The pH was raised to 11 by addition of 6.0 N aqueous sodium hydroxide and the layers were separated. The ethyl acetate layer washed once with 1.0 N aqueous sodium hydroxide, dried over MgSO$_4$, filtered, and concentrated to a brown oil. The oil was dissolved in 7.0 mL of isopropanol and 600 mg (2.0 mmol) of epoxide P (Example 15, part a) were added. The solution was heated to 70° C. After 34 h, the solution was concentrated and the product partially purified by silica gel chromatography (gradient of 1 to 2% methanol in CH$_2$Cl$_2$). Fractions containing product were combined and concentrated to afford T as a yellow oil.

Example 61B

Synthesis of N-{2-[4-(3-phenyl-4-methoxyphenyl)aminophenyl]ethyl}-(R)-2-hydroxy-2-(8-hydroxy-2(1H)-quinolinon-5-yl)ethylamine (61)

To a solution of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP) (4.0 g, 6.5 mmol) in tetrahydrofuran (100 mL) and water (16 mL) was added 10% palladium on carbon (800 mg). The reaction was stirred vigorously under one atmosphere of hydrogen for 6.5 h. The solids were filtered off and washed with tetrahydrofuran (4×25 mL) and then 50% methanol/tetrahydrofuran (2×25 mL). The combined filtrates were evaporated to dryness and the crude product was purified by reverse-phase HPLC. Fractions containing pure product were combined and lyophilized. The product from several runs was combined to give 4.68 g which was dissolved in acetonitrile (200 mL) and water (200 mL). 1.0 N HCl (18.7 mL) was added, and the solution was lyophilized. The residue was again dissolved in acetonitrile (125 mL) and water (125 mL). 1.0 N HCl was added and the solution was lyophilized to give a hydrochloride salt of compound 61 as an off white powder. $^1$H NMR (300 MHz, DMSO-d6) δ 10.55 (br s, 1H), 9.40 (br s, 1H), 8.80, (br s, 1H), 8.26 (d, 1H), 7.60, (br s, 2H) 7.25-7.45 (m, 5H), 6.92-7.16 (m 10H), 6.55 (d, 1H), 5.45 (d, 1H), 3.69 (s, 3H), 2.80-3.15 (m, 6H); m/z: [M+H+] calcd for $C_{32}H_{31}N_3O_4$ 522.24. found 522.4.

The intermediate PP was prepared as follows:

a. Synthesis of 8-acetoxy-2(1H)-quinolinone (CC)

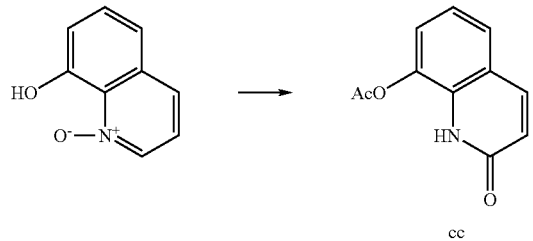

8-Hydroxyquinoline-N-oxide (160.0 g, 1.0 mol) and acetic anhydride (800 mL, 8.4 mol) were heated at 100° C. for 3 hours and then cooled in ice. The product was collected on a Buchner funnel, washed with acetic anhydride (2×100 mL) and dried under reduced pressure to give 8-acetoxy-2(1H)-quinolinone (CC) (144 g) as a tan solid.

b. Synthesis of 5-acetyl-8-hydroxy-2(1H)-quinolinone (DD)

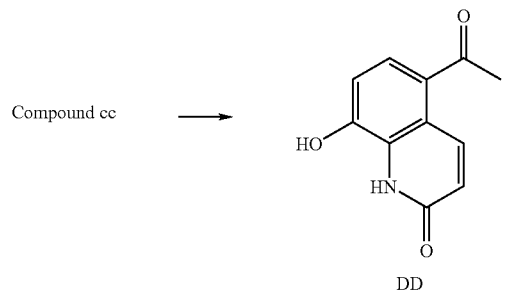

A slurry of aluminum chloride (85.7 g, 640 mmol) in 1,2-dichloroethane (280 mL) was cooled in ice, and compound CC (56.8 g, 280 mmol) was added. The mixture was warmed to room temperature, and then heated at 85° C. After 30 minutes acetyl chloride (1.5 mL, 21 mmol) was added and the mixture was heated an additional 60 minutes. The reaction mixture was then cooled and added to 1N HCl (3 L) at 0° C. with stirring. After stirring for 2 hours, the solids were collected on a Buchner funnel, washed with water (3×250 mL) and dried under reduced pressure. The crude product isolated from several batches (135 g) was combined and triturated with dichloromethane (4 L) for 6 hours. The product was collected on a Buchner funnel and dried under reduced pressure to give 5-acetyl-8-hydroxy-2(1H)-quinolinone (DD) (121 g).

c. Synthesis of 5-acetyl-8-benzyloxy-2(1H)-quinolinone (EE)

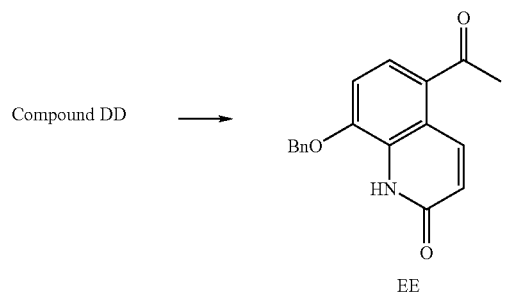

To 5-acetyl-8-hydroxy-2-quinolone (37.7 g, 186 mmol) was added dimethylformamide (200 mL) and potassium carbonate (34.5 g, 250 mmol) followed by benzyl bromide (31.8 g, 186 mmol). The mixture was stirred at room temperature for 2.25 hour and then poured into saturated sodium chloride (3.5 L) at 0° C. and stirred well for 1 hour. The product was collected and dried on a Buchner funnel for 1 hour, and the resulting solids were dissolved in dichloromethane (2 L) and dried over sodium sulfate. The solution was filtered through a pad of Celite and washed with dichloromethane (5×200 mL). The combined filtrate was then concentrated to dryness and the resulting solids were triturated with ether (500 mL) for 2 hours. The product was collected on a Buchner funnel, washed with ether (2×250 mL) and dried under reduced pressure to give 5-acetyl-8-benzyloxy-2(1H)-quinolinone (EE) (44 g) as an off white powder.

d. Synthesis of 5-(2-bromo-1-oxy)ethyl-8-benzyloxy-2(1H)-quinolinone (R)

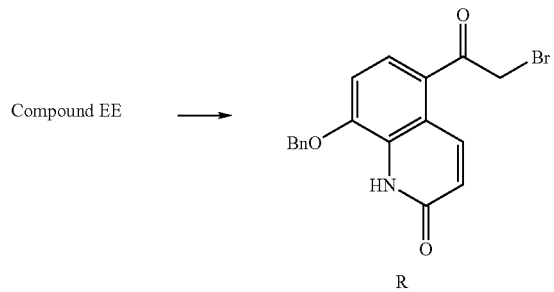

5-Acetyl-8-benzyloxy-2(1H)-quinolinone (EE) (20.0 g, 68.2 mmol) was dissolved in dichloromethane (200 mL) and cooled to 0° C. Boron trifluoride diethyl etherate (10.4 mL, 82.0 mmol) was added via syringe and the mixture was warmed to room temperature to give a thick suspension. The suspension was heated at 45° C. (oil bath) and a solution of bromine (11.5 g, 72.0 mmol) in dichloromethane (100 mL) was added over 40 minutes. The mixture was kept 45° C. for an additional 15 minutes and then cooled to room temperature. The mixture was concentrated under reduced pressure and then triturated with 10% aqueous sodium carbonate (200 mL) for 1 hour. The solids were collected on a Buchner funnel, washed with water (4×100 mL) and dried under reduced pressure. The product of two runs was combined for purification. The crude product (52 g) was triturated with 50% methanol in chloroform (500 mL) for 1 hour. The product was collected on a Buchner funnel and washed with 50% methanol in chloroform (2×50 mL) and methanol (2×50 mL). The solid was dried under reduced pressure to give 5-(2-bromo-1-oxy)ethyl-8-benzyloxy-2(1H)-quinolinone (R) (34.1 g) as an off white powder.

e. Synthesis of 5-(2-bromo-(R)-1-hydroxy)ethyl-8-benzyloxy-2(1H)-quinolinone (FF)

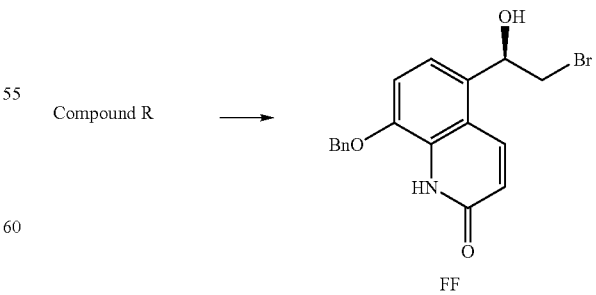

Using a procedure described in Mathre et al., *J. Org. Chem.*, 1991, 56, 751-762, a catalyst was prepared as follows. (R)-(+)-α, α-Diphenylprolinol (10.0 g, 39 mmol) and trimethylboroxine (3.7 mL, 26 mmol) were combined in toluene (200 mL) and stirred at room temperature for 30 min. The mixture was placed in a 150° C. oil bath and 150 mL liquid was distilled away. Toluene (50 mL) was added, and another 50 mL of distillate was collected. Another portion of toluene (50 mL) was added and a further 50 mL of distillate was collected. A 1.00 mL aliquot of the material remaining in the pot was evaporated to dryness and weighed (241.5 mg) to determine that the concentration of catalyst was 0.87 M.

5-(2-Bromo-1-oxy)ethyl-8-benzyloxy-2(1H)-quinolinone (R) (30.0 g, 81 mmol) was suspended in, tetrahydrofuran (1.2 L) under a nitrogen atmosphere and the catalyst from above (13 mL, 11 mmol) was added. The suspension was cooled to −5° C. in an ice/isopropanol bath and borane (1.0 M in THF, 97 mL, 97 mmol) was added over 3 h. The reaction was stirred an additional 45 min at −5° C., then methanol (200 mL) was added slowly. The mixture was concentrated under vacuum to give 5-(2-bromo-(R)-1-hydroxy)ethyl-8-benzyloxy-2(1H)-quinolinone (FF).

f. Synthesis of 5-(2-bromo-(R)-1-tert-butyldimethylsiloxy) ethyl-8-benzyloxy-2(1H)-quinolinone (HH)

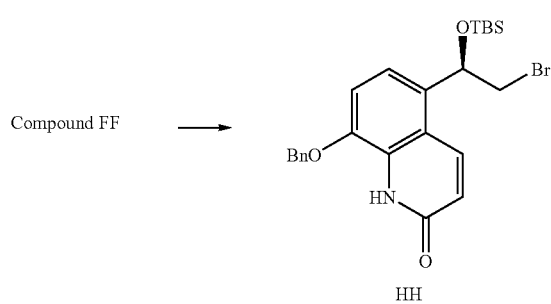

Compound FF (15 g, 40 mmol) and 2,6-lutidine (9.3 mL, 80 mmol) were suspended in dichloromethane at 0° C. tert-Butyldimethylsilyl trifluoromethanesulfonate (18.5 mL, 80 mmol) was added dropwise. The mixture was allowed to warm to room temperature and stirred overnight. The reaction was diluted with dichloromethane (200 mL) and washed twice with 1N hydrochloric acid, then three times with brine. The organics were dried over magnesium sulfate and the volume was reduced to 100 mL under vacuum. The organics were applied to a silica gel column equilibrated with 30% ethyl acetate in hexanes and the product was eluted with 50% ethyl acetate in hexanes. Removal of the solvent under reduced pressure gave 5-(2-bromo-(R)-1-tert-butyldimethyl-siloxy)ethyl-8-benzyloxy-2(1H)-quinolinone (HH). (10.3 g). Unreacted starting material (compound FF, 2 g) was also recovered.

g. Synthesis of N-tert-butoxycarbonyl-2-[4-(3-[phenyl-4-methoxyphenyl)aminophenyl]ethylamine (LL)

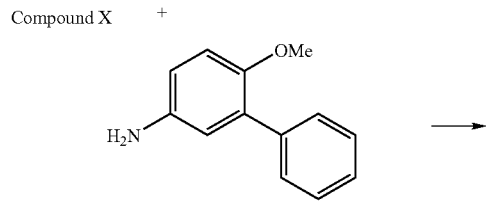

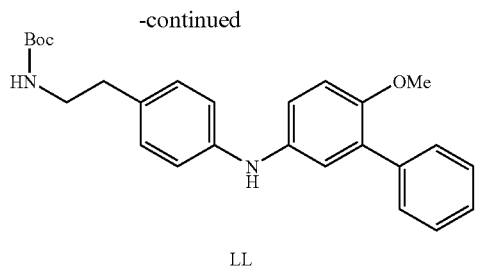

Under nitrogen, compound X (from Example 38 part a) (5.0 g, 16.7 mmol) was mixed with toluene (80 mL) and 4-methoxy-3-phenylaniline hydrochloride (4.3 g, 18.3 mmol) was added to form a slurry. 2,2'-Bis(diphenylphosphino)-1,1'-binaphthyl (1.6 g, 2.5 mmol) was added, followed by tris(dibenzylideneacetone)dipalladium(0) (760 mg, 0.83 mmol) and finally sodium tert-butoxide (5.3 g, 55 mmol). The mixture was heated at 90° C. for 150 min and then cooled to room temperature. Water (150 mL) was added followed by ethyl acetate (150 mL) and the phases partitioned. The aqueous layer was extracted with ethyl acetate (150 mL) and the combined organics washed three times with 0.5 M sodium bisulfate (200 mL), once with saturated sodium bicarbonate (150 mL) and twice with saturated sodium chloride (150 mL). The organics were dried over magnesium sulfate (50 g) and the volatiles removed under vacuum to give N-tert-butoxycarbonyl-2-[4-(3-[phenyl-4-methoxyphenyl)aminophenyl] ethylamine (LL) (8.4 g) which was used without further purification.

h. Synthesis of 2-[4-(3-[phenyl-4-methoxyphenyl)aminophenyl]ethylamine (MM)

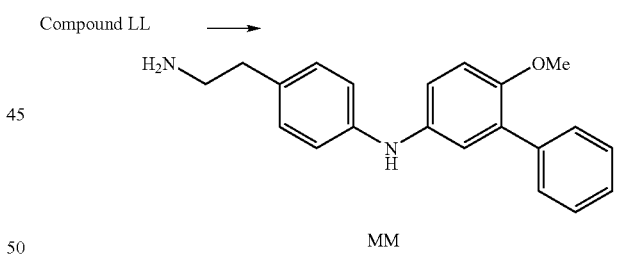

Under nitrogen, compound LL (94.6 g) was treated with dichloromethane (500 mL) and cooled in an ice bath. Hydrogen chloride (4 M in dioxane, 125 mL, 500 mmol) was added in 10 portions over 20 min. The reaction was kept at room temperature for 130 minutes, during which time the product precipitated. The solid was filtered and washed with dichloromethane (350 mL) and dried under vacuum in the dark to give the dihydrochloride salt of 2-[4-(3-[phenyl-4-methoxyphenyl)aminophenyl]ethylamine (MM) (37.1 g). $^1$H NMR (300 MHz, DMSO-d6) δ 8.29 (br s, 2H), 8.04 (br s, 1H) 7.25-7.50 (m, 5H), 6.90-7.08 (m, 7H), 3.69 (s, 3H), 2.93 (m, 2H), 2.75 (m, 2H); m/z: [M+H$^+$] calcd for $C_{21}H_{22}N_2O$ 319.18. found 319.3.

91 i. Synthesis of N-{2-[4-(3-phenyl-4-methoxyphenyl)aminophenyl]ethyl}-(R)-2-tert-butyldimethylsiloxy-2-(8-benzyloxy-2(1H)-quinolinon-5-yl)ethylamine (NN)

Compound HH + MM ⟶

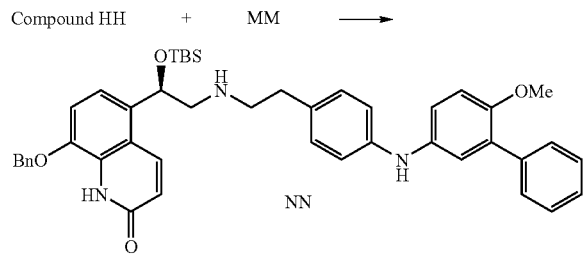

The dihydrochloride salt of compound MM was partitioned between isopropyl acetate and 1.0 N sodium hydroxide. The organic layer was dried over sodium sulfate and concentrated to give the free base as a dark oil.

Sodium iodide (4.2 g, 28 mmol), compound HH (9.1 g, 18.6 mmol) and sodium bicarbonate (4.7 g, 55.9 mmol) were weighed into a flask. Under nitrogen, compound MM (7 g, 22 mmol) in dimethyl sulfoxide (20 mL) was added and the mixture stirred at 140° C. (oil bath) for 30 min, then cooled to room temperature. Ethyl acetate was added (200 mL) and the mixture washed three times with 1N hydrochloric acid, then with 1N sodium hydroxide, saturated sodium bicarbonate and finally saturated sodium chloride (200 mL each). The organics were dried over sodium sulfate and evaporated to dryness to give N-{2-[4-(3-phenyl-4-methoxyphenyl)aminophenyl]ethyl}-(R)-2-tert-butyldimethylsilyl-2-(8-benzyloxy-2(1H)-quinolinon-5-yl)ethylamine (NN) (13.9 g) which was used in the next step without further purification.

j. Synthesis of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP)

Compound NN ⟶

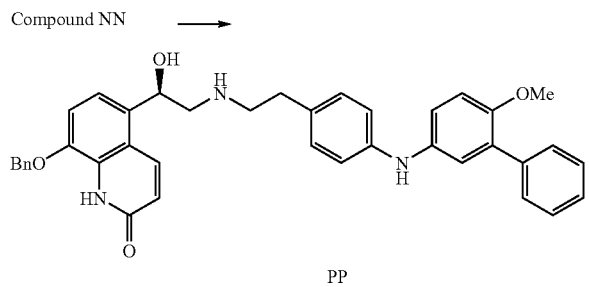

Compound NN (13.9 g) was combined with methanol (200 mL) and concentrated hydrochloric acid (170 mL) was added in portions (exothermic). The solution turned orange and cloudy after the addition and more methanol (100 mL) was added until a clear solution was obtained. The mixture was stirred at room temperature overnight, in which time a brown gum had formed. The solvent was removed under vacuum, and ethyl acetate (300 mL) was added. The resulting mixture was cooled in an ice bath, and neutralized (pH 7) with 10 N sodium hydroxide. The pH was then raised to 10 with 1 M sodium hydroxide to give a clear biphasic mixture. The phases were separated and the aqueous layer was extracted with ethyl acetate (300 mL). The combined organic layers were dried over sodium sulfate, and evaporated to dryness. The crude product was purified by flash chromatography on

92 silica gel (500 g, 0-10% methanol in dichloromethane) to give N-{2-[4-(3-phenyl-4-methoxyphenyl)aminophenyl]ethyl}-(R)-2-hydroxy-2-(8-benzyloxy-2(1H)-quinolinon-5-yl)ethylamine (PP) (5.6 g).

Example 61C

Synthesis of N-{2-[4-(3-phenyl-4-methoxyphenyl)aminophenyl]ethyl}-(R)-2-hydroxy-2-(8-hydroxy-2(1H)-quinolinon-5-yl)ethylamine (61)

a. Synthesis of 5-(2-bromo-(R)-1-hydroxy)ethyl-8-benzyloxy-2(1H)-quinolinone (FF)

(R)-(+)-α,α-Diphenylprolinol (30.0 g, 117 mmol) and trimethylboroxine (11.1 mL, 78 mmol) were combined in toluene (300 mL) and stirred at room temperature for 30 minutes. The mixture was placed in a 150° C. oil bath and liquid was distilled off. Toluene was added in 20 mL aliquots, and distillation was continued for 4 hours. A total of 300 mL toluene was added. The mixture was finally cooled to room temperature. A 500 µL aliquot was evaporated to dryness, weighed (246 mg) to determine that the concentration of catalyst was 1.8 M.

5-(2-Bromo-1-oxy)ethyl-8-benzyloxy-2(1H)-quinolinone (R) (90.0 g, 243 mmol) was placed under nitrogen, tetrahydrofuran (900 mL) was added followed by the catalyst from above (1.8 M in toluene, 15 mL, 27 mmol). The suspension was cooled to −10±5° C. in an ice/isopropanol bath. Borane (1.0 M in THF, 294 mL, 294 mmol) was added over 4 hours. The reaction was stirred an additional 45 minutes at −10° C., then methanol (250 mL) was added slowly. The mixture was concentrated under vacuum. The residue was dissolved in boiling acetonitrile (1.3 L), filtered while hot and cooled to room temperature. The crystals were filtered, washed with acetonitrile and dried under reduced pressure to give 5-(2-bromo-(R)-1-hydroxy)ethyl-8-benzyloxy-2(1H)-quinolinone (FF) (72.5 g, 196 mmol, 81% yield, 95% ee, 95% pure by HPLC area ratio).

b. Synthesis of 5-(2-bromo-(R)-1-tert-butyldimethylsiloxy)ethyl-8-benzyloxy-2(1H)-quinolinone (HH)

Compound FF (70.2 g, 189 mmol) was treated with N,N-dimethylformamide (260 mL) and cooled in an ice bath under nitrogen. 2,6-Lutidine (40.3 g, 376 mmol) was added over 5 minutes followed slowly by tert-butyldimethylsilyl trifluoromethanesulfonate (99.8 g, 378 mmol), keeping the temperature below 20° C. The mixture was allowed to warm to room temperature for 45 minutes. Methanol (45 mL) was added to the mixture dropwise over 10 minutes and the mixture was partitioned between ethyl acetate/cyclohexane (1:1, 500 mL) and water/brine (1:1, 500 mL). The organics were washed twice more with water/brine (1:1, 500 mL each). The combined organics were evaporated under reduced pressure to give a light yellow oil. Two separate portions of cyclohexane (400 mL) were added to the oil and distillation continued until a thick white slurry was formed. Cyclohexane (300 mL) was added to the slurry and the resulting white crystals were filtered, washed with cyclohexane (300 mL) and dried under reduced pressure to give 5-(2-bromo-(R)-1-tert-butyldimethylsiloxy)ethyl-8-benzyloxy-2(1H)-quinolinone (HH) (75.4 g, 151 mmol, 80% yield, 98.6% ee).

c. Synthesis of N-[2-(4-bromophenyl)ethyl}-(R)-2-tert-butyldimethylsiloxy-2-(8-benzyloxy-2(1H)-quinolinon-5-yl)ethylamine (JJ)

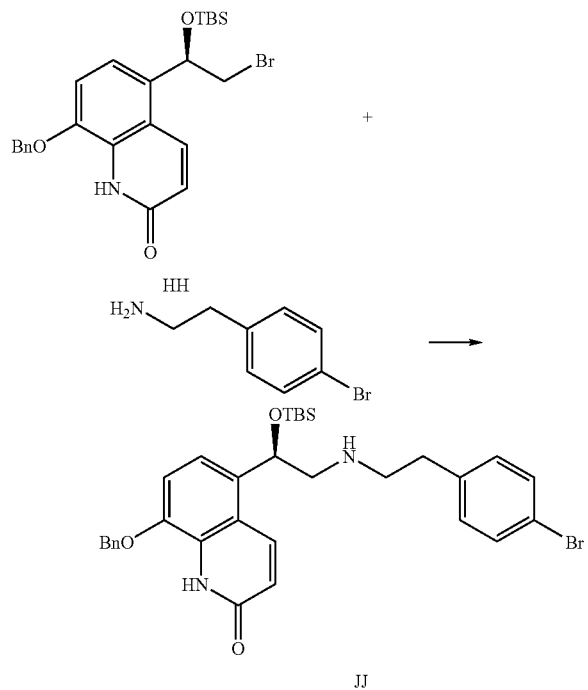

Compound HH (136.5 g, 279 mmol), 4-bromophenethylamine (123 g, 615 mmol) and dimethyl sulfoxide (180 mL) were mixed at room temperature under nitrogen. Another 40 mL of dimethyl sulfoxide was added. The mixture was heated to 85° C. for 5 hours. The reaction was partitioned between ethyl acetate (1 L) and 10% aqueous acetic acid (500 mL). The organics were washed with 10% aqueous acetic acid (3×500 mL), then with 1N sodium hydroxide (3×500 mL). The last wash was filtered through Celite (100 g). The organic layer was concentrated to 300 mL and cyclohexane (2×500 mL) was added and the solution concentrated to 300 mL. Sufficient cyclohexane was added to form 1.8 L final volume which was filtered through Celite (50 g). A solution of HCl in isopropanol, prepared by slowly adding concentrated HCl (23.5 mL) to isopropanol (180 mL) at 10° C. (internal), was added to the crude product and the reaction mixture was stirred for 5 hours, washed with cyclohexane (2×500 mL) and dried under reduced pressure for 24 hours to give N-[2-(4-bromophenyl)ethyl}-(R)-2-tert-butyldimethylsiloxy-2-(8-benzyloxy-2(1H)-quinolinon-5-yl)ethylamine (JJ) hydrochloride (145 g, 80 mol %, 106 wt %, HPLC purity 97.9%).

d. Synthesis of N-{2-[4-(3-phenyl-4-methoxyphenyl)aminophenyl]ethyl}-(R)-2-tert-butyldimethylsilyl-2-(8-benzyloxy-2(1H)-quinolinon-5-yl)ethylamine (NN)

To compound JJ hydrochloride (73.7 g, 114 mmol) and 4-methoxy-3-phenylaniline hydrochloride (32.4 g, 137 mmol), toluene (380 mL) was added with mild agitation for 5 minutes, followed by sodium tert-butoxide (49.3 g, 513 mmol) in portions over 1 minute, and finally 2,2'-bis(diphenylphosphino)-1,1'-binaphthyl (10.65 g, 17 mmol) and tris (dibenzylideneacetone)dipalladium(0) (5.22 g, 5.7 mmol). The resulting mixture was stirred and heated to 85-89° C. (internal) for 2.5 hours. The solution was cooled to room temperature, water (400 mL) was added and the mixture was stirred for 5 minutes, filtered through Celite (80 g), and partitioned with toluene (100 mL). The organic layer was collected and concentrated under reduced pressure in a 40° C. bath to give N-{2-[4-(3-phenyl-4-methoxyphenyl)aminophenyl]ethyl}-(R)-2-tert-butyldimethylsilyl-2-(8-benzyloxy-2(1H)-quinolinon-5-yl)ethylamine (NN) as a dark viscous oil.

e. Synthesis of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP)

Compound NN from the previous step was dissolved in 280 ml of THF. Triethylamine trihydrofluoride (27.6 g, 171 mmol) was added to the solution, an additional 20 mL of THF was used to rinse down residual reagent, and the reaction was stirred at 25° C. under nitrogen for 16 hours. The reaction mixture was concentrated under reduced pressure in a 25° C. bath to give a dark viscous oil to which dichloromethane (400 mL) was added, followed by 1N aqueous NaOH (200 mL). The reaction mixture was stirred for 5 hours. The top layer was discarded and the organic layer was concentrated to a viscous oil.

The oil was dissolved in dichloromethane to give a total volume of 630 mL. A 60 mL aliquot was taken and concentrated to 30 mL. Toluene (60 mL) was added, followed by a mixture of concentrated hydrochloric acid (2.7 mL) and methanol (4.5 mL) to give a thick paste covered in a free-flowing liquid. The liquid was carefully removed and the paste washed with toluene (50 mL). The gum was partitioned between dichloromethane (40 mL) and 1N aqueous sodium hydroxide (40 mL) and the organic solvents were removed under reduced pressure. The residue was purified chromatographically over silica using a gradient of 0-10% methanol in dichloromethane to give N-{2-[4-(3-phenyl-4-methoxyphenyl)aminophenyl]ethyl}-(R)-2-hydroxy-2-(8-benzyloxy-2 (1H)-quinolinon-5-yl)ethylamine (PP). (98.6% pure by HPLC area ratio)

f. Purification of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP)

Intermediate PP (0.5 g, 0.82 mmol, Pd level ~850 ppm by ICP) was dissolved in 1:1 dichloromethane:methanol (5 mL) and 4M hydrochloric acid in dioxane (0.445 mL, 1.78 mmol) was added. The resulting dark brown solution was diluted further with dichloromethane (7.5 mL) and 3-(1-thioureido) propyl functionalized silica gel (0.05 g) was added (Sigma-Aldrich, St. Louis, Mo.). The suspension was stirred at room temperature for 20 h followed by filtration through filter paper. The remaining yellow silica washed with a mixture of 5 mL of methanol and 30 mL of dichloromethane. Combined organic solutions were washed with saturated aqueous sodium bicarbonate (50 mL) and brine (50 mL). The organic solution was treated with anhydrous sodium sulfate for 30 minutes, filtered and evaporated under reduced pressure to give N-{2-[4-(3-phenyl-4-methoxyphenyl)aminophenyl]ethyl}-(R)-2-hydroxy-2-(8-benzyloxy-2(1H)-quinolinon-5-yl)ethylamine (PP) (~90% yield, Pd level by ICP 30 ppm, purity 97.4% by HPLC area ratio).

g Synthesis of N-{2-[4-(3-phenyl-4-methoxyphenyl)aminophenyl]ethyl}-(R)-2-hydroxy-2-(8-hydroxy-2(1H)-quinolinon-5-yl)ethylamine (61) hydrochloride To compound PP from the previous step (2.1 g, 3.43 mmol) was added under nitrogen 10% palladium on carbon (420 mg) followed by ethylene glycol (16 mL) and concentrated hydrochloric acid (0.57 mL, 6.9 mmol). The suspension was stirred vigorously under 1 atmosphere of hydrogen for 5 h. The solids were filtered off and washed with ethylene glycol (5 mL). The filtrate was warmed to 50° C. and water (21 mL) was added over 5 minutes under stirring. A brown gum formed which broke up to an off-white solid under continued stirring at 50° C. for 40 min. The solid was filtered off, washed with water (2×20 mL) and air dried to afford an amorphous hydrochloride salt of compound 61 (2.5 g containing 44.3% water, 74% yield)

To improve the purity of the title compound, (2.5 g, 4.8 mmol) was dissolved in methanol (25 mL) at 40° C. The dark blue solution was cooled to room temperature, decolorizing charcoal (Darco-KB, 2.5 g) was added and the suspension stirred at room temperature overnight. Solids were filtered off over Celite (2.0 g), filter cake washed with methanol (2×10 mL) and solvent was evaporated under reduced pressure to leave an amorphous hydrochloride salt of N-{2-[4-(3-phenyl-4-methoxyphenyl)aminophenyl]ethyl}-(R)-2-hydroxy-2-(8-hydroxy-2(1H)-quinolinon-5-yl)ethylamine (61) as a light gray solid (1.5 g)

Example 62

Synthesis of Compound 62

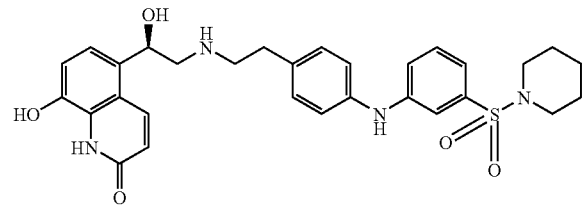

To a solution of 70 mg of compound nn (0.09 mmol) in 5 mL of glacial acetic acid was added 21 mg of 10% palladium on carbon. The reaction was shaken under an atmosphere of H$_2$ at 40 psi. After 18 h, the reaction was filtered and the filtrate purified by reversed-phase HPLC (gradient of 10 to 50% acetonitrile in 0.1% aqueous TFA) to afford compound 62 (10 mg, 0.0126 mmol) as the TFA salt. $^1$H NMR (300 MHz, DMSO-d$_6$) δ 1.21-1.33 (m, 2H), 1.39-1.52 (m, 4H), 2.74 (m, 4H), 2.82 (m, 2H), 2.96-3.20 (m, 4H), 5.25 (m, 1H), 6.13 (m, 1H), 6.51 (m, 1H), 6.90 (d, 1H, J=8.2 Hz), 7.01 (d, 2H, J=8.8 Hz), 7.07-7.15 (m, 5H), 7.43 (d, 2H, J=9.1 Hz), 8.07 (d, 2H, J=9.9 Hz), 8.61 (br s, 2H), 8.76 (s, 1H), 10.39 (s, 1H), 10.46 (s, 1H). m/z: [M+H$^+$] calcd for C$_{30}$H$_{34}$N$_4$O$_5$S 563.7. found 563.3.

The intermediate compound nn was prepared as follows.

a. Synthesis of Compound kk.

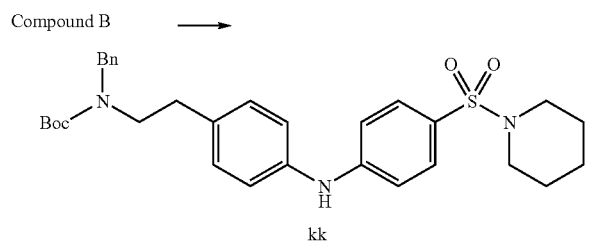

To a flask containing 4.51 g (11.6 mmol) of compound B (Example 13, part b), 3.61 g (15.0 mmol) of 4-(piperidinosulfonyl)aniline (available from Maybridge), 0.53 g (0.58 mmol) of tris(dibenzylidineacetone)dipalladium(0), 1.19 g (1.91 mmol) of racemic-2,2'-bis(diphenylphosphino)-1,1'-binaphthyl, and 1.45 g (15.1 mmol) of sodium tert-butoxide was added toluene (60 mL), and the mixture was stirred at 95° C. for 6 h under a nitrogen atmosphere. The mixture was diluted with 200 mL diethyl ether and washed twice with 100 mL portions of 1.0 M aqueous NaHSO$_4$, followed by 100 mL of saturated aqueous NaHCO$_3$. The diethyl ether phase was dried over MgSO$_4$, filtered, and concentrated to a dark oil. The oil was purified by silica gel chromatography (gradient of 30 to 40% ethyl acetate in hexanes) to afford compound kk as an orange foam.

b. Synthesis of Compound mm.

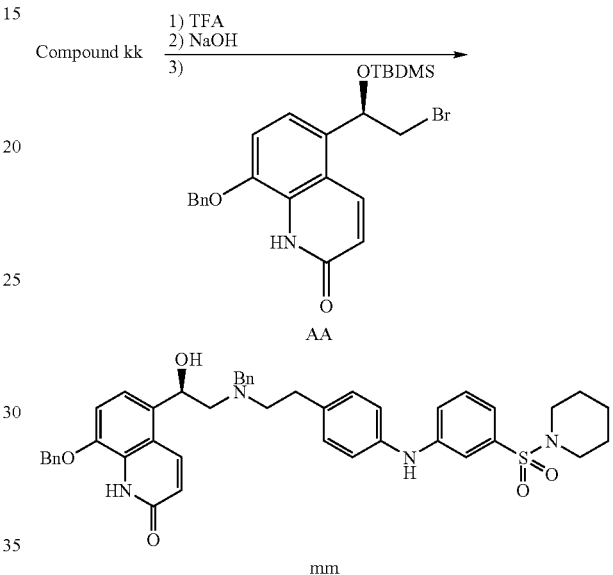

A solution of compound kk (2.88 g, 5.24 mmol) in 20 mL CH$_2$Cl$_2$ was cooled to 0° C. and 20 mL of TFA was added. After 20 min, the reaction was concentrated and the residue dissolved in isopropyl acetate. The isopropyl acetate solution washed twice with 1.0 N aqueous NaOH followed by water and then dried over MgSO$_4$, filtered and concentrated to an oil. The oil was dissolved in 2 mL DMF and intermediate AA (337 mg, 0.69 mmol), diethyl isopropyl amine (179 mg, 1.38 mmol) and potassium iodide (172 mg, 1.04 mmol) were added. The reaction was heated to 100° C. After 18 h, the reaction was cooled and added to vigorously stirred ice water. Compound mm precipitated, was isolated by filtration and purified by silica gel chromatography (1:1 ethyl acetate/hexanes) to afford 544 mg solid.

c. Synthesis of Compound nn.

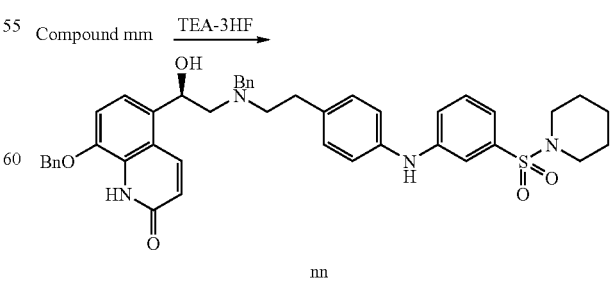

To a solution of compound mm (83 mg, 0.01 mmol) in CH$_2$Cl$_2$ (0.9 mL) and triethylamine (0.09 mL) was added triethylamine trihydrofluoride (313 mg, 1.94 mmol). The solution was stirred at room temperature under a N₂ atmosphere. After 18 h, the reaction mixture was diluted with CH₂Cl₂ and washed with 1.0 N aqueous HCl, followed by two washes with saturated NaCl solution. The organic phase was dried over MgSO₄, filtered and concentrated under reduced pressure to afford compound nn (70 mg).

Example 63

Synthesis of Compound 63

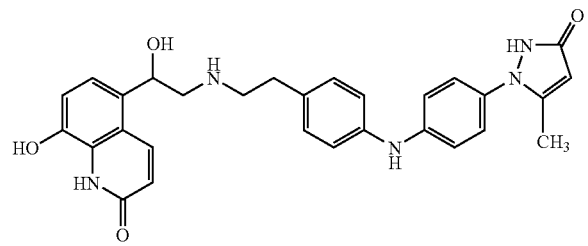

To a solution of 730 mg of compound rr (1.05 mmol) in 10 mL of glacial acetic acid was added 100 mg of 10% palladium on carbon. The reaction was stirred under an atmosphere of H₂. After 65 h, the reaction was filtered and the filtrate purified by reversed-phase HPLC (gradient of 10 to 50% acetonitrile in 0.1% aqueous TFA) to afford 90 mg (0.14 mmol) the TFA salt. The TFA salt product was solubilized in acetonitrile/water (1:2, 10 mL) to which 3 mL of 0.1 N aqueous HCl was added. The solution was frozen and lyophilized to afford compound 63 as an HCl salt. m/z: [M+H⁺] calcd for C₂₉H₂₉N₅O₄ 512.6. found 512.3.

Intermediate rr was prepared as follows.

a. Synthesis of Compound qq

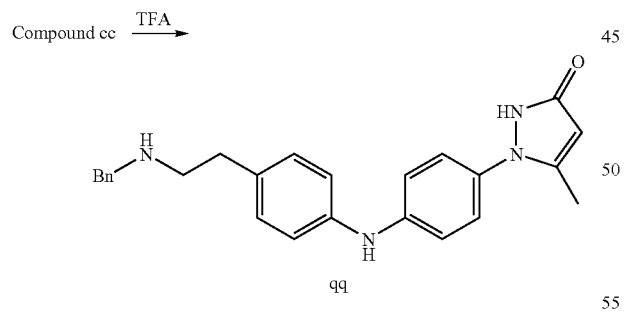

To 0.99 g of compound cc (Example 60, part a) (1.99 mmol) in 5 mL CH₂Cl₂ was added 2 mL TFA. After 1 h, the solution was concentrated, diluted with 15 mL CH₂Cl₂ and washed with 1.0 N aqueous sodium hydroxide. The aqueous was collected and washed again with CH₂Cl₂ (10 mL) followed by a wash with ethyl acetate (10 mL). The organic layers were combined and dried over MgSO₄, filtered, and concentrated under reduced pressure. The crude product was purified by silica gel chromatography (gradient of 2-10% MeOH in CH₂Cl₂) to afford intermediate qq as an oil.

a. Synthesis of Compound rr.

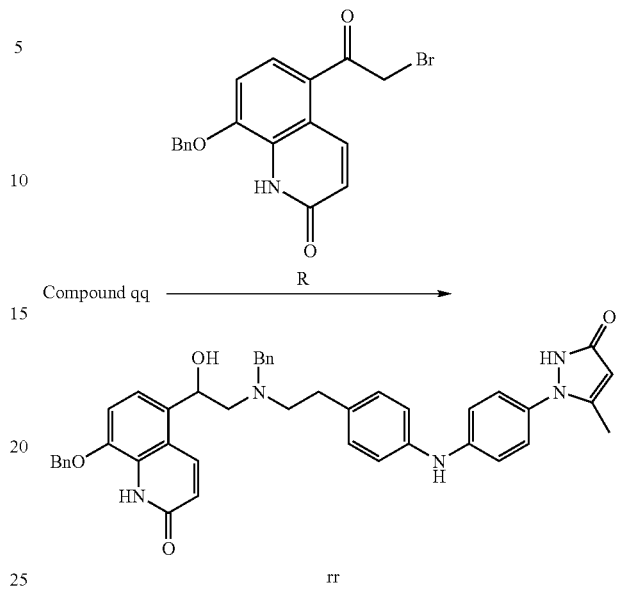

To a solution of compound qq (2.0 6, 5.0 mmol) in 27 mL DMF were added bromoketone R (from Example 56, part a) (1.71 g, 4.5 mmol) and K₂CO₃ (1.91 g, 13.8 mmol). The reaction was heated to 50° C. After 1 h, the reaction was allowed to cool to room temperature and the K₂CO₃ was filtered off. The filtrate was diluted with CH₂Cl₂ (50 mL) and washed with 0.1N HCl (30 mL). The organic layer washed once with saturated sodium bicarbonate solution, followed by aqueous saturated sodium chloride, dried over Na₂SO₄ and concentrated under reduced pressure to afford an oil. The product (1.14 g, 1.65 mmol) was solubilized in 12 mL THF/EtOH (1:1) and NaBH₄ (380 mg, 10.0 mmol) was added. After 20 minutes of vigorous stirring. The reaction was quenched with saturated aqueous NH₄Cl which was added until effervescence of the reaction mixture ceased. The reaction mixture was partitioned between ethyl acetate and saturated sodium bicarbonate solution. The organic layer washed twice with saturated sodium bicarbonate, followed by saturated sodium chloride, dried over Na₂SO₄ and concentrated under reduced pressure. The crude product was purified by silica gel chromatography (2% MeOH in CH₂Cl₂) to yield 230 mg of intermediate rr.

Example 64

Synthesis of N-{2-[4-(4-ethoxyphenyl)aminophenyl]ethyl}-(R)-2-hydroxy-2-(3-formamido-4-hydroxyphenyl)ethylamine (64)

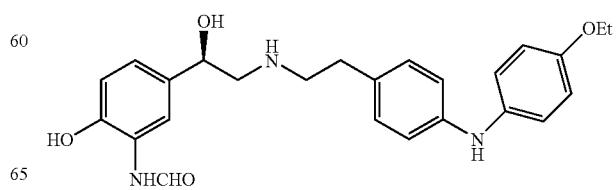

To a mixture of 580 mg (0.93 mmol) of compound V in 25 mL of ethanol was added 173 mg of 10% palladium on carbon under a stream of nitrogen. The flask was fitted with a balloon of hydrogen gas, and the reaction was vigorously stirred for 4 days. The reaction was filtered and the filtrate was concentrated under reduced pressure. The residue was purified by reverse phase HPLC using a gradient of 10 to 50% acetonitrile in 0.1% aqueous TFA. Fractions containing pure product were combined and lyophilized to afford a TFA salt of compound 64 as an off-white powder.

A sample of the TFA salt of compound 64 (150 mg) was dissolved in acetonitrile (2.0 mL) and water (2.0 mL). 0.1 N HCl (7.0 mL, 0.70 mmol) was added, and the resulting precipitate was redissolved by the addition of acetonitrile. The resulting solution was lyophilized to give a solid which was again dissolved in acetonitrile (5.0 mL) and water (5.0 mL). 0.1N HCl (7.0 mL, 0.7 mmol) was added and the resulting solution was lyophilized to give a hydrochloride salt of compound 64 as an off white powder. $^1$H NMR (300 MHz, DMSO-d6) δ 10.10 (br s, 1H), 9.62 (s, 1H), 8.80 (br s, 1H), 8.65 (br s, 1H), 8.27 (d, 1H), 8.15 (d, 1H), 6.80-7.15 (m, 11H), 4.78 (dd, 1H), 3.94 (quar, 2H), 2.80-3.15 (m, 6H), 1.29 (t, 3H); m/z: [M+H$^+$] calcd for $C_{25}H_{29}N_3O_4$ 436.22. found 436.3.

The intermediate compound V was prepared as follows.

a. Synthesis of Compound V.

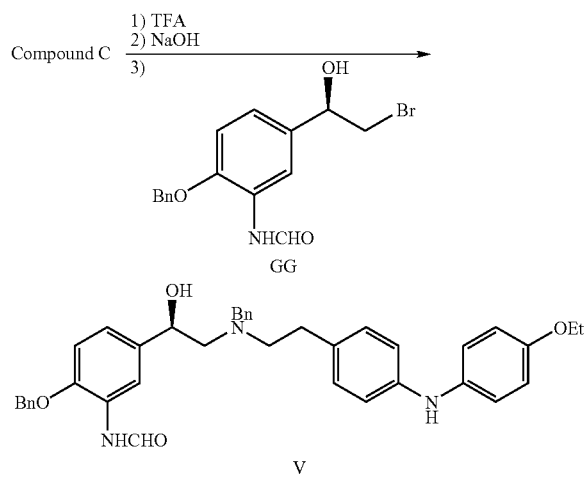

To 0.60 g (1.3 mmol) of compound C (Example 37, part a) in 20 mL of CH$_2$Cl$_2$ at 0° C. was added 2.0 mL of trifluoroacetic acid. After 1 h, the solution was concentrated under reduced pressure, and the residue was partitioned between 1.0 M aqueous NaOH and EtOAc. The phases were separated, and the EtOAc phase was dried over MgSO$_4$, filtered, and concentrated to an oil and dissolved in 10 mL of 1:1 methanol:THF. Bromohydrin GG (Example 13, part d) (360 mg, 1.0 mmol) and K$_2$CO$_3$ (380 mg, 2.7 mmol) were added and the reaction was stirred at room temperature for 1.5 h. The reaction was diluted with 30 mL water and extracted twice with 30 mL portions of toluene. The toluene extracts were combined, dried over MgSO$_4$, filtered, and concentrated. The residue was heated to 120° C. After 2 h, the residue was cooled to room temperature and purified by silica gel chromatography (gradient of 5 to 10% methanol in CH$_2$Cl$_2$). Fractions containing pure product were combined and concentrated to afford compound V as a tan solid.

Example 65

Synthesis of N-{2-[4-(3-phenylphenyl)aminophenyl]ethyl}-(R)-2-hydroxy-2-(8-hydroxy-2(1H)-quinolinon-5-yl)ethylamine (65)

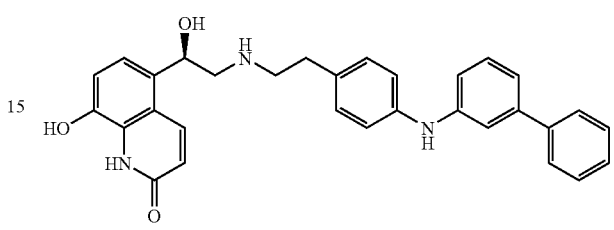

Compound W (55.2 mg, 0.094 mmol), phenyl boronic acid (13.2 mg, 0.113 mmol) and [1,1'-bis(diphenylphosphinoferrocene)dichloropalladium (II), complex with dichloromethane (PdCl$_2$(dppf)-DCM) (5.0 mg, 0.006 mmol) were combined in a small pressure tube and purged with N$_2$. 1,2-Dimethoxyethane (1.0 mL) and 2.0 N cesium carbonate (150 µL, 0.3 mmol) were added. The tube was sealed, and then placed in an oil bath at 90° C. for 4 hours. The solution was then cooled to room temperature and DCM (10 mL) was added. The solution was filtered and concentrated to dryness. To the residue there was added DMF (1.0 mL), 10% Pd/C (100 mg) and ammonium formate (200 mg) and the solution was heated to 50° C. for 1.5 hours. At this time, water:acetonitrile 1:1 and 200 µL TFA was added and the solution was filtered to remove the catalyst. The filtrate was purified by reverse phase HPLC. Fractions containing pure product were combined and lyophilized to give compound 65 as a TFA salt. $^1$H NMR (300 MHz, DMSO-d6) δ 10.46 (s, 1H), 10.39 (s, 1H), 8.60 (br s, 2H), 8.19 (s, 1H), 8.07 (d, 1H), 7.50 (d, 2H), 7.37 (t, 2H) 7.15-7.30 (m, 3H), 6.85-7.10 (m, 9H), 6.51 (dd, 1H), 6.11 (d, 1H), 5.23 (d, 1H), 2.70-3.15 (m, 6H); m/z: [M+H$^+$] calcd for $C_{31}H_{29}N_3O_3$ 492.23. found 492.3.

a. Synthesis of Compound U

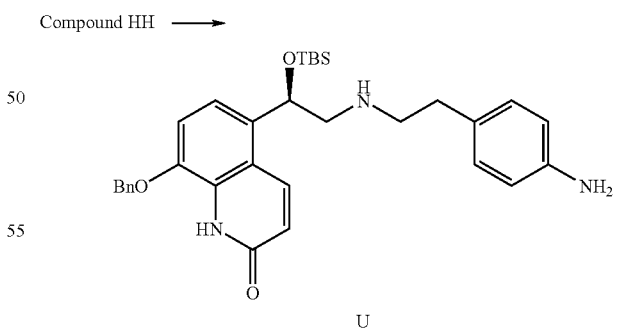

Compound HH (Example 61B, part f) (9.1 g, 18.62 mmol), 4-aminophenethylamine (9.8 mL, 74.8 mmol) and sodium iodide (4.2 g, 27.93 mmol) were placed in a flask and purged with nitrogen. Methyl sulfoxide (25 mL) was added, and the solution was placed in an oil bath heated at 140° C. The solution was the stirred for 20 min at 140° C. The reaction was allowed to cool to room temperature, then ethyl acetate (300 mL) and H₂O (300 mL) were added. The phases were partitioned, and the organic layer washed with water (4×200 mL) and saturated sodium chloride (4×200 mL). The organic phase was dried over sodium sulfate, filtered and concentrated under vacuum to yield compound U (10.5 g).

b. Synthesis of Compound W

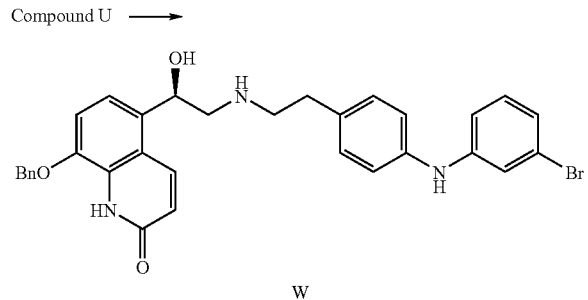

Compound U (5.18 g, 9.53 mmol), tris(dibenzylideneacetone)dipalladium(0) (0.44 g, 0.48 mmol), 2,2'-bis(diphenylphosphino)-1,1'-binaphthyl (0.63 g, 0.95 mmol), and sodium t-butoxide (1.83 g, 19.06 mmol) were combined in a flask and purged with nitrogen. 1-Bromo-3-iodobenzene (2.0 mL, 11.44 mmol) was added and the flask was purged again. o-Xylene (50 mL) was added, and the solution was heated at reflux under nitrogen for 2.5 hours, at which time HPLC analysis indicated complete reaction. The o-xylene was removed under vacuum with heating, and dichloromethane (200 mL) was added. Once the residue was dissolved, celite (30 g) was added, and the mixture was filtered and filter cake washed with dichloromethane until all of the product was collected. The solution was concentrated to dryness under vacuum, redissolved in THF (20 mL), and purged with nitrogen. Tetrabutylammonium fluoride (20 mL, 1.0 M in THF, 20 mmol) was added via syringe, and the solution was stirred for 18 hours at room temperature. The THF was then removed, and the residue was dissolved in DCM, and washed with water (1×200 mL) and half-saturated sodium chloride (1×200 mL). The organic phase was dried over sodium sulfate, concentrated and chromatographed over silica gel (50 g, 0-10% MeOH in dichloromethane) to yield compound W as a yellow solid.

Synthesis of Compounds of Formula (X)—Compounds 66-93

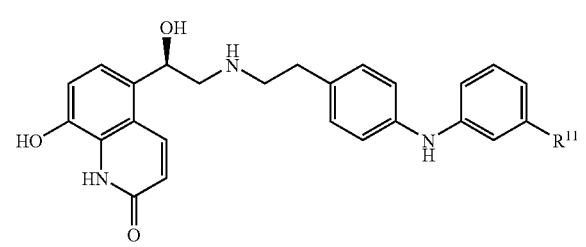

Examples 66-69

Synthesis of Compounds 66-69

Using procedures similar to that described in Example 65, except replacing the phenylboronic acid with the appropriate substituted phenylboronic acid, TFA salts of compounds 66-69 were prepared.

Compound 66: N-{2-[4-(3-(2-chlorophenyl)phenyl)aminophenyl]ethyl}-(R)-2-hydroxy-2-(8-hydroxy-2(1H)-quinolinon-5-yl)ethylamine (Formula (X) where $R^{11}$ is 2-chlorophenyl): ¹H NMR (300 MHz, DMSO-d6) δ 10.47 (s, 1H), 10.37 (s, 1H), 8.55, (br s, 2H), 8.22, (s, 1H), 8.06 (d, 1H), 7.46 (m, 1H), 7.32 (m, 3H), 7.22 (t, 1H), 7.01 (m, 8H), 6.89 (d, 1H), 6.74 (dd, 1H), 6.51 (d, 1H), 6.10 (d, 1H), 3.18 (m, 4H), 2.80 (m, 2H); m/z: [M+H⁺] calcd for $C_{31}H_{28}ClN_3O_3$ 526.19. found 526.4.

Compound 67: N-{2-[4-(3-(2-methoxyphenyl)phenyl)aminophenyl]ethyl}-(R)-2-hydroxy-2-(8-hydroxy-2(1H)-quinolinon-5-yl)ethylamine (Formula (X) where $R^{11}$ is 2-methoxyphenyl): ¹H NMR (300 MHz, DMSO-d6) δ 10.46 (s, 1H), 10.40 (s, 1H), 8.60 (br s, 2H), 8.12 (s, 1H), 8.06 (d, 1H), 7.16 (m, 13H), 6.80 (d, 1H), 6.51 (d, 1H) 6.11 (s, 1H) 5.24 (d, 1H), 3.69 (s, 3H), 3.10 (m, 4H), 2.80 (m, 2H); m/z: [M+H⁺] calcd for $C_{32}H_{31}N_3O_4$ 522.24. found 522.7.

Compound 68: Formula (X) where $R^{11}$ is 4-hydroxymethylphenyl: ¹H NMR (300 MHz, DMSO-d6) δ 10.47 (s, 1H), 10.39 (s, 1H), 8.60 (br s, 2H), 8.18 (s, 1H), 8.07 (d, 1H), 7.46 (d, 2H), 7.30 (d, 2H), 7.20 (m, 2H), 7.00 (m, 8H), 6.51 (dd, 1H), 6.11 (s, 1H), 5.23 (d, 1H), 4.44 (s, 2H), 3.10 (m, 4H), 2.80 (m, 2H); m/z: [M+H⁺] calcd for $C_{32}H_{31}N_3O_4$ 522.24. found 522.4.

Compound 69: Formula (X) where $R^{11}$ is 4-methoxyphenyl: ¹H NMR (300 MHz, DMSO-d6) δ 10.47 (s, 1H), 10.39 (s, 1H) 8.60 (br s, 2H), 8.16 (s, 1H), 8.07 (d, 1H), 7.44 (d, 2H), 6.85-7.20 (m, 12H), 6.51 (dd, 1H), 6.12 (d, 1H), 5.23 (d, 1H), 3.70 (s, 3H), 3.10 (m, 4H), 2.80 (m, 2H); m/z: [M+H⁺] calcd for $C_{32}H_{31}N_3O_4$ 522.24. found 522.4.

Example 70

Synthesis of Compound 70

Compound 70: Formula (X) where $R^{11}$ is 4-chlorophenyl Compound W (84.0 mg, 0.143 mmol), 4-chlorophenyl boronic acid (27.2 mg, 0.172 mmol) and [1,1'-bis(diphenylphosphinoferrocene)dichloropalladium (II), complex with dichloromethane (PdCl₂(dppf)-DCM) (5.9 mg, 0.007 mmol) were combined in a small pressure tube and purged with N₂. 1,2-Dimethoxyethane (2.0 mL) and 2.0 N cesium carbonate (150 uL, 0.3 mmol) were added. The tube was sealed, and then placed in an oil bath at 90° C. for 4 hours. The solution was then cooled to room temperature and DCM (10 mL) was added. The solution was filtered and concentrated to dryness. To the residue there was added DMF (1.0 mL) and 10% palladium on carbon (10 mg), and the reaction was stirred under one atmosphere of hydrogen for 4 hours. At this time, water:acetonitrile 1:1 and 200 uL TFA was added and the solution was filtered to remove the catalyst. The filtrate was purified by reverse phase HPLC. Fractions containing pure product were combined and lyophilized to give compound 70 as a TFA salt. ¹H NMR (300 MHz, DMSO-d6) δ 10.46 (s, 1H), 10.40 (s, 1H), 8.61 (br s, 2H), 8.22 (s, 1H), 8.07 (d, 1H), 7.53 (d, 2H), 7.42 (d, 2H), 7.23 (t, 1H), 7.14 (s, 1H), 6.85-7.10 (m, 8H), 6.51 (s, 1H), 6.12 (s, 1H), 5.24 (d, 1H), 3.10 (m, 4H), 2.80 (m, 2H); m/z: [M+H⁺] calcd for $C_{31}H_{28}ClN_3O_3$ 526.19. found 526.4.

Examples 71-72

Synthesis of Compounds 71-72

Using procedures similar to that described in Example 70, except replacing the 4-chlorophenylboronic acid with the appropriate substituted boronic acid, TFA salts of compounds 71-72 were prepared.

Compound 71: Formula (X) where $R^{11}$ is 5-indolyl: $^1$H NMR (300 MHz, DMSO-d6) δ 11.07 (s, 1H), 10.47 (s, 1H), 10.40 (s, 1H), 8.60 (br s, 2H), 8.15 (s, 1H), 8.11 (d, 1H), 7.65 (s, 1H), 7.15-7.40 (m, 5H), 7.00-7.15 (m, 5H), 6.89 (d, 2H), 6.51 (dd, 1H), 6.39 (s, 1H), 6.11 (s, 1H), 5.24 (d, 1H), 3.10 (m, 4H), 2.80 (m, 2H); m/z: [M+H$^+$] calcd for $C_{33}H_{30}N_4O_3$ 531.24. found 531.4.

Compound 72: Formula (X) where $R^{11}$ is 4-pyridyl: $^1$H NMR (300 MHz, DMSO-d6) δ 10 48 (s, 1H) 10.38 (s, 1H), 8.60 (br m, 4H), 8.32 (s, 1H), 8.07 (d, 1H), 7.69 (d, 2H), 7.31 (m, 2H), 7.16 (d, 1H) 7.05 (m, 6H), 6.90 (d, 1H), 6.52 (dd, 1H), 6.11 (s, 1H), 5.24 (d, 1H), 3.10 (m, 4H), 2.80 (m, 2H); m/z: [M+H$^+$] calcd for $C_{30}H_{28}N_4O_3$ 493.23. found 493.5.

Example 73

Synthesis of Compound 73

Compound 73: Formula (X) where $R^{11}$ is hydrogen: A TFA salt of compound 73 was prepared: $^1$H NMR (300 MHz, DMSO-d6) δ 10.48 (s, 1H), 10.39 (s, 1H), 8.59 (br s, 2H), 8.07 (dd, 2H), 6.85-7.17 (m, 10H), 6.72 (t, 1H), 6.52 (dd, 1H), 6.11 (d, 1H), 5.22 (d, 1H), 3.10 (m, 4H), 2.80 (m, 2H); m/z: [M+H$^+$] calcd for $C_{25}H_{25}N_3O_3$ 416.20. found 416.3.

Example 74

Synthesis of N-{2-[4-(3-(3-cyanophenyl)phenyl)aminophenyl]ethyl}-(R)-2-hydroxy-2-(8-hydroxy-2(1H)-quinolinon-5-yl)ethylamine (74)

Compound 74: Formula (X) where $R^{11}$ is 3-cyanophenyl

Compound W (Example 65, part b) (58.1 mg, 0.100 mmol), 3-cyanophenyl boronic acid (17.6 mg, 0.120 mmol) and [1,1'-bis(diphenylphosphinoferrocene)dichloropalladium (II), complex with dichloromethane (PdCl$_2$(dppf)-DCM) (approximately 6 mg, 0.007 mmol) were combined in a small pressure tube and purged with N$_2$. 1,2-Dimethoxyethane (2.0 mL) and 2.0 N cesium carbonate (200 uL, 0.4 mmol) were added, the tube was sealed, and then placed in an oil bath at 90° C. for 5 hours. The solution was then cooled to room temperature and DCM (10 mL) was added. The solution was dried (Na$_2$SO$_4$) for 30 minutes, then filtered, concentrated and dried under vacuum. The residue was dissolved in DCM (2 mL) and cooled to 0° C., then boron trichloride (1.0 N in DCM, 1.0 mL, 1.0 mmol) was added. After 10 minutes the reaction was quenched with methanol (10 mL), and concentrated under reduced pressure. The residue was purified by reverse phase HPLC. Fractions containing pure product were combined and lyophilized to give compound 74 as a TFA salt. $^1$H NMR (300 MHz, DMSO-d6) δ 10.45 (s, 1H), 10.40 (s, 1H), 8.70 (br 2, 2H), 8.34 (m, 1H), 8.09 (d, 1H), 7.97 (s, 1H), 7.85 (dt, 1H), 7.74 (dt, 1H), 7.58 (t, 1H), 7.20-7.30 (m, 2H), 6.95-7.10 (m, 7H), 6.90 (d, 1H), 6.50 (d, 1H), 6.12 (s, 1H), 5.25 (d, 1H), 3.10 (m, 4H), 2.80 (m, 2H); m/z: [M+H$^+$] calcd for $C_{32}H_{28}N_4O_3$ 517.23. found 517.4.

Examples 75-93

Synthesis of Compounds 75-93

Using procedures similar to that described in Example 74, except replacing the 3-cyanophenyl boronic acid with the appropriate substituted boronic acid, TFA salts of compounds 75-93 were prepared.

Compound 75: Formula (X) where $R^{11}$ is trans-2-phenylvinyl: m/z: [M+H$^+$] calcd for $C_{33}H_{31}N_3O_3$ 518.25. found 518.3.

Compound 76: N-{2-[4-(3-(3-pyridyl)phenyl)aminophenyl]ethyl}-(R)-2-hydroxy-2-(8-hydroxy-2(1H)-quinolinon-5-yl)ethylamine (Formula (X) where $R^{11}$ is 3-pyridyl): $^1$H NMR (300 MHz, DMSO-d6) δ 10.38 (br s, 2H), 8.84 (s, 2H), 8.67 (s, 1H), 8.58 (d, 1H), 8.25 (s, 1H), 8.14 (d, 1H), 8.11 (d, 1H), 7.59 (dd, 1H), 7.27 (m, 2H), 7.05 (m, 7H), 6.90 (d, 1H), 6.50 (d, 1H), 5.28 (d, 1H), 3.10 (m, 4H), 2.83 (m, 2H). m/z: [M+H$^+$] calcd for $C_{30}H_{28}N_4O_3$ 493.23. found 493.5.

Compound 77: Formula (X) where $R^{11}$ is 4-cyanophenyl: $^1$H NMR (300 MHz, DMSO-d6) δ10.45 (br s, 1H), 10.40 (s, 1H), 8.62 (br, s, 2H), 8.27 (s, 1H), 8.07 (d, 1H), 7.84 (d, 2H), 7.72 (d, 2H), 7.27 (m, 2H), 7.18 (m, 7H), 6.91 (d, 1H), 6.52 (d, 1H), 6.12 (s, 1H), 5.24 (m, 1H), 3.12 (m, 4H), 2.81 (m, 2H). m/z: [M+H$^+$] calcd for $C_{32}H_{28}N_4O_3$ 516.60. found 517.4.

Compound 78: Formula (X) where $R^{11}$ is 3,5-dimethylisoxazole-4-yl: m/z: [M+H$^+$] calcd for $C_{30}H_{30}N_4O_4$ 511.24. found 511.5.

Compound 79: Formula (X) where $R^{11}$ is 2-furanyl: $^1$H NMR (300 MHz, DMSO-d6) δ 11.15 (s, 1H), 10.47 (s, 1H), 10.41 (s, 1H), 8.64 (br s, 1H), 8.10 (t, 2H), 7.08 (m, 9H), 6.77 (s, 1H), 6.74 (s, 1H), 6.52 (d, 1H), 6.30 (s, 1H), 6.12 (s, 1H), 6.02 (q, 1H), 5.25 (d, 1H), 3.10 (m, 4H), 2.85 (m, 2H). m/z [M+H$^+$] calcd for $C_{29}H_{27}N_3O_4$ 482.21. found 481.4.

Compound 80: Formula (X) where $R^{11}$ is thiophene-2-yl: $^1$H NMR (300 MHz, DMSO-d6) δ 10.47 (s, 1H), 10.38 (s, 1H), 8.62 (br s, 2H), 8.22 (s, 1H), 8.07 (d, 1H), 7.44 (d, 1H), 7.33 (d, 1H), 7.35 (m, 2H), 7.06 (m, 7H), 6.90 (d, 2H), 6.50 (d, 1H), 6.10 (d, 1H), 5.23 (m, 1H), 3.10 (m, 4H), 2.85 (m, 2H). m/z [M+H$^+$] calcd for $C_{29}H_{27}N_3O_3S$ 498.19. found 498.5.

Compound 81: Formula (X) where $R^{11}$ is 3-nitrophenyl: m/z: [M+H$^+$] calcd for $C_{31}H_{28}N_4O_5$ 537.22. found 537.3.

Compound 82: Formula (X) where $R^{11}$ is 4-formylphenyl: m/z: [M+H$^+$] calcd for $C_{32}H_{29}N_3O_4$ 520.23. found 520.5.

Compound 83: Formula (X) where $R^{11}$ is 2-pyrrolyl: Using a procedure similar to that described in Example 74, except replacing the 3-cyanophenylboronic acid with 1-(tert-butoxycarbonyl)pyrrole-2-boronic acid, a TFA salt of compound 83 was prepared. Deprotection of the Boc group occurred under reaction conditions. $^1$H NMR (300 MHz, DMSO-d6) δ 11.13 (s, 1H), 10.46 (s, 1H), 10.37 (s, 1H), 8.58 (br s, 2H), 8.08 (s, 1H), 8.05 (s, 1H), 7.05 (m, 9H), 6.75 (s, 1H), 6.73 (s, 1H), 6.51 (d, 1H), 6.23 (s, 1H), 6.08 (s, 1H), 6.01 (s, 1H), 5.22 (m, 1H), 3.12 (m, 4H), 2.80 (m, 2H). m/z: [M+H$^+$] calcd for $C_{29}H_{28}N_4O_3$ 481.23. found 481.3.

Compound 84: Formula (X) where $R^{11}$ is 4-carboxyphenyl: m/z: [M+H$^+$] calcd for $C_{32}H_{29}N_3O_5$ 536.22. found 536.3.

Compound 85: Formula (X) where $R^{11}$ is 4-methylsulfonylphenyl: $^1$H NMR (300 MHz, DMSO-d6) δ 10.45 (s, 1H), 10.38 (s, 1H), 8.58 (br s, 1H), 8.27 (s, 1H), 8.05 (d, 1H), 7.90 (d, 2H), 7.77 (d, 2H), 7.26 (m, 2H), 7.04 (m, 7H), 6.88 (d, 1H), 6.50 (d, 1H), 6.11 (s, 1H), 5.22 (d, 1H), 3.16 (s, 3H), 3.11 (m, 4H), 2.80 (m, 2H). m/z: [M+H$^+$] calcd for $C_{32}H_{31}N_3O_5S$ 570.21. found 570.3.

Compound 86: Formula (X) where $R^{11}$ is 4-hydroxyphenyl: Using a procedure similar to that described in Example 74, except replacing the 3-cyanophenylboronic acid with 4-benzyloxyphenylboronic acid, a TFA salt of compound 86 was prepared. $^1$H NMR (300 MHz, DMSO-d6) δ 10.46 (s, 1H), 10.40 (s, 1H), 9.47 (s, 1H), 8.71 (br s, 2H), 8.12 (m, 2H), 7.32 (d, 2H), 7.02 (m, 9H), 6.75 (d, 2H), 6.51 (d, 1H), 6.10 (s, 1H), 5.25 (d, 1H), 3.10 (m, 4H), 2.80 (m, 2H). m/z: [M+H$^+$] calcd for $C_{31}H_{29}N_3O_4$ 508.23. found 508.3.

Compound 87: N-{2-[4-(3-(4-aminomethylphenyl)phenyl)aminophenyl]ethyl}-(R)-2-hydroxy-2-(8-hydroxy-2(1H)-quinolinon-5-yl)ethylamine (Formula (X) where $R^{11}$ is 4-(aminomethyl)phenyl): m/z: [M+H$^+$] calcd for $C_{32}H_{32}N_4O_3$ 521.26. found 521.3.

Compound 88: Formula (X) where $R^{11}$ is 4-ethoxyphenyl: m/z: [M+H$^+$] calcd for $C_{33}H_{33}N_3O_4$ 536.26. found 536.3.

Compound 89: Formula (X) where $R^{11}$ is thiophene-3-yl: m/z: [M+H$^+$] calcd for $C_{29}H_{27}N_3O_3S$ 498.19. found 498.3.

Compound 90: Formula (X) where $R^{11}$ is 2-indolyl: m/z: [M+H$^+$] calcd for $C_{33}H_{30}N_4O_3$ 531.24. found 531.3.

Compound 91: N-{2-[4-(3-(3-chlorophenyl)phenyl)aminophenyl]ethyl}-(R)-2-hydroxy-2-(8-hydroxy-2(1H)-quinolinon-5-yl)ethylamine (Formula (X) where $R^{11}$ is 3-chlorophenyl): $^1$H NMR (300 MHz, DMSO-d6) δ 10.45 (s, 1H), 10.38 (s, 1H), 8.58 (br s, 2H), 8.20 (s, 1H), 8.06 (d, 1H), 7.21 (m, 14H), 6.51 (d, 1H), 6.10 (s, 1H), 5.23 (d, 1H), 3.10 (m, 4H), 2.80 (m, 2H). [M+H] calcd for $C_{31}H_{28}ClN_3O_3$ 526.03. found 526.3.

Compound 92: Formula (X) where $R^{11}$ is 3-methoxyphenyl: m/z: [M+H] calcd for $C_{32}H_{31}N_3O_4$ 522.24. found 522.0.

Compound 93: Formula (X) where $R^{11}$ is 3-fluorophenyl: $^1$H NMR (300 MHz, DMSO-d6) δ 10.42 (s, 1H), 10.39 (s, 1H), 8.60 (br s, 2H), 8.20 (s, 1H), 8.15 (d, 1H), 7.2 (m, 14H), 6.51 (d, 1H), 6.11 (s, 1H), 5.23 (d, 1H), 3.10 (m, 4H), 2.81 (m, 2H). m/z: [M+H$^+$] calcd for $C_{31}H_{28}FN_3O_3$ 509.58. found 510.3.

Synthesis of Compounds of Formula (XI)—Compounds 94-101

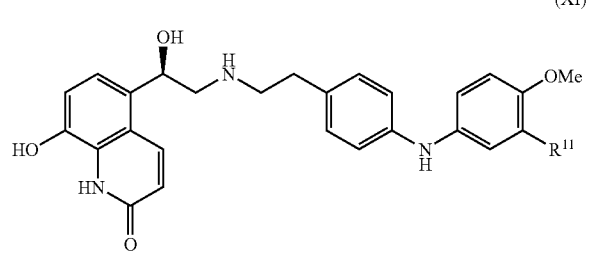

(XI)

Example 94

Synthesis of N-{2-[4-(3-(3-pyridyl)-4-methoxyphenyl)aminophenyl]ethyl}-(R)-2-hydroxy-2-(8-hydroxy-2(1H)-quinolinon-5-yl)ethylamine (94)

Compound 94: Formula (XI) where $R^{11}$ is 3-pyridyl a. Synthesis of 4-iodophenethylamine 4-Iodophenylacetonitrile (4.80 g, 19.7 mmol) was dissolved in tetrahydrofuran (25 mL) under nitrogen, and 1.0 M borane in tetrahydrofuran (29.6 mL, 29.6 mmol) was added via syringe. The reaction was heated at reflux for 1 hour, then cooled in ice and the excess borane was quenched by the addition of methanol (100 mL). When hydrogen evolution ceased, the solvents were removed under reduced pressure. The residue was dissolved in tetrahydrofuran (25 mL) and 4N HCl in dioxane (6.0 mL, 24 mmol) was added, followed by ether (75 mL). The hydrochloride salt of 4-iodophenethylamine was collected on a Buchner funnel, washed with ether (2×50 mL) and dried under reduced pressure. To generate the free base, the solid was partitioned between dichloromethane (200 mL) and 1N NaOH (100 mL). The aqueous layer was extracted with dichloromethane (2×100 mL). The combined organic layers were dried (Na$_2$SO$_4$) and concentrated to give 4-iodophenethylamine (4.52 g) as a colorless oil.

b. Synthesis of Compound QQ

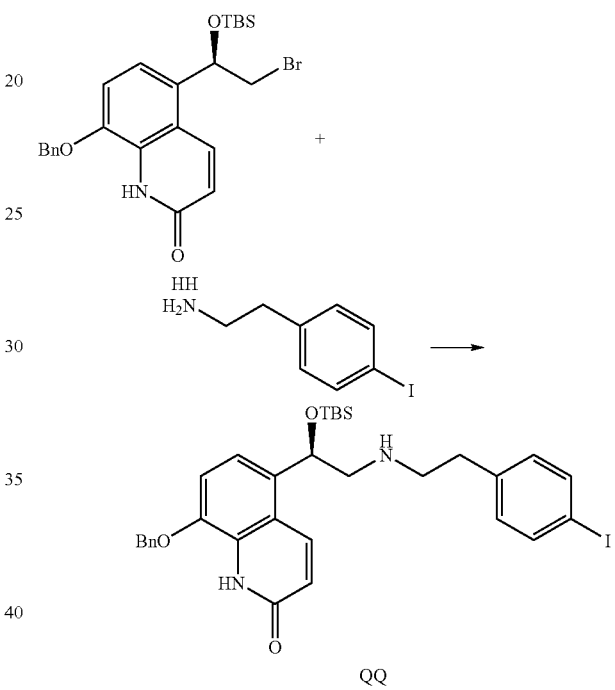

To a solution of 4-iodophenethylamine (4.5 g, 22 mmol) in methyl sulfoxide (13 mL) under nitrogen was added compound HH (from Example 61B part f) (7.3 g, 15 mmol), sodium bicarbonate (3.7 g, 44 mmol) and sodium iodide (3.3 g, 22 mmol). The mixture was heated at 140° C. in an oil bath for 25 minutes. After cooling to room temperature, water (100 mL) was added and the resulting mixture was extracted with ethyl acetate (2×150 mL). The combined extracts were washed with 1N HCl (2×50 mL), water (50 mL) 10% sodium thiosulfate (50 mL), saturated sodium bicarbonate (50 mL) and brine (50 mL). The solution was dried (Na$_2$SO$_4$) and concentrated. The crude product was purified in two lots by flash chromatography on silica gel (75 g) eluting with 0-5% methanol in dichloromethane containing 0.5% triethylamine. Compound QQ (6.1 g) was isolated as a dark yellow oil.

c. Synthesis of 4-amino-2-bromoanisole

To a mixture of 2-bromo-4-nitroanisole (5.0 g, 21.5 mmol, Lancaster), ethanol (25 mL) and water (25 mL), was added powdered iron (4.8 g, 86 mmol) and 12 N HCl (0.5 mL). The solution was heated at reflux for 20 minutes. 1N NaOH (10 mL) was added and the reaction mixture was filtered through a pad of celite while still hot, and then rinsed with ethanol (2×50 mL). The ethanol was removed under reduced pressure and the residue extracted with dichloromethane (2×100 mL). The organic extracts were dried (Na₂SO₄) and concentrated. The crude product was purified by flash chromatography on silica gel (75 g) eluting with dichloromethane, to give 4-amino-2-bromoanisole as a light tan solid.

d. Synthesis of Compound RR

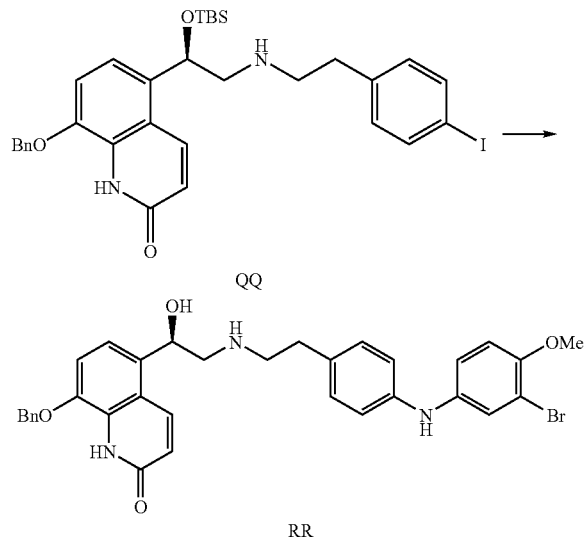

A flask containing compound QQ (0.966 g, 1.48 mmol), 4-amino-2-bromoanisole (0.35 g, 1.78 mmol), tris(dibenzylidineacetone)dipalladium(0) (0.068 g, 0.074 mmol), BINAP (0.092 g, 0.148 mmol), and sodium tert-butoxide (0.569 g, 5.92 mmol) was flushed with nitrogen, and then anhydrous o-xylene (30 mL) was added. The mixture was heated at 115° C. in an oil bath for two hours. At this time, the reaction was cooled to room temperature and the solvent was removed under reduced pressure. The brownish residue was redissolved in dichloromethane and filtered through a bed of celite. The filtrate was concentrated to dryness under reduced pressure, dissolved in THF (20 mL) and purged with nitrogen. Tetrabutylammonium fluoride (1.0 N in THF, 4.5 mL, 4.5 mmol) was added and the solution was stirred for 18 hours at room temperature. The solvent was removed under reduced pressure, and the residue partitioned between water and DCM. The organic layer washed with saturated sodium bicarbonate and brine, dried over sodium sulfate and concentrated under reduced pressure. The crude product was purified by flash chromatography on silica gel (1-10% MeOH in DCM) to give compound RR.

e. Synthesis of Compound 94

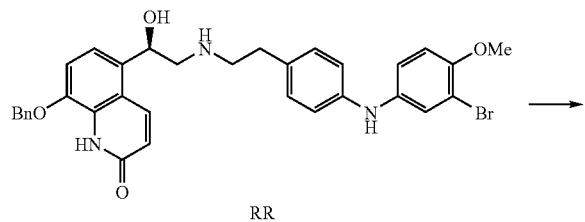

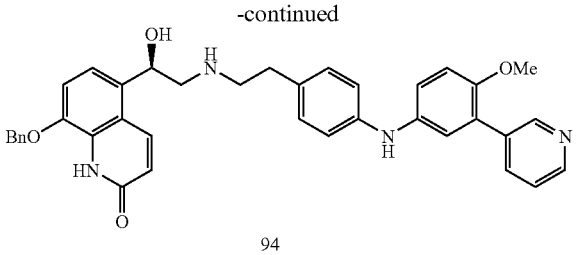

Into a nitrogen purged test tube with a screw cap was placed compound RR (73 mg, 0.12 mmol), [1,1'-bis(diphenylphosphino)-ferrocene]dichloropalladium(II) dichloromethane complex (10 mg) and 3-pyridylboronic acid (18 mg, 0.14 mmol). Dimethoxyethane (2.5 mL) was added, followed by 2.0 N cesium carbonate (0.20 mL, 0.40 mmol). The mixture was heated at 90° C. for 4 hours. The solution was then cooled to room temperature and DCM (20 mL) was added. The solution was dried (Na₂SO₄) for 30 minutes, then filtered, concentrated and dried under vacuum. The residue was dissolved in DCM (2 mL) and cooled to 0° C., and then boron trichloride (1.0 N in DCM, 1.0 mL, 1.0 mmol) was added. After 10 minutes the reaction was quenched with methanol (10 mL), and concentrated under reduced pressure. The residue was purified by reverse phase HPLC. Fractions containing pure product were combined and lyophilized to give a TFA salt of N-{2-[4-(3-(3-pyridyl)-4-methoxyphenyl)aminophenyl]ethyl}-(R)-2-hydroxy-2-(8-hydroxy-2(1H)-quinolinon-5-yl)ethylamine (94). ¹H NMR (300 MHz, DMSO-d6) δ 10.; m/z: [M+H⁺] calcd for $C_{31}H_{30}N_4O_4$ 523.24. found 523.3.

A sample of the TFA salt (25 mg) was dissolved in acetonitrile (0.5 mL) and water (0.5 mL), followed by 1N HCl (0.10 mL, 0.10 mmol). The solution was lyophylized to a powder which was redissolved in acetonitrile (0.5 mL) and water (0.5 mL). 1N HCl was then added (0.10 mL, 0.10 mmol). Lyophylization gave a hydrochloride salt of compound 94 as an off white powder. ¹H NMR (300 MHz, DMSO-d6) δ 10.49 (br s, 1H), 9.44 (br s, 1H), 8.97 (d, 1H), 8.78 (d, 1H), 8.77 (br s, 1H), 8.61 (dt, 1H), 8.20 (d, 1H), 8.01 (dd, 1H), 6.90-7.15 (m, 8H), 6.47 (d, 1H), 5.39 (d, 1H), 3.70 (s, 3H), 3.02 (m, 4H), 2.82 (m, 2H); m/z: [M+H⁺] calcd for $C_{31}H_{30}N_4O_4$ 523.24. found 523.6.

Example 95

Synthesis of N-{2-[4-(3-(3-cyanophenyl)-4-methoxyphenyl)aminophenyl]ethyl}-(R)-2-hydroxy-2-(8-hydroxy-2(1H)-quinolinon-5-yl)ethylamine (95)

Compound 95: Formula (XI) where $R^{11}$ is 3-cyanophenyl.

Into a nitrogen purged test tube with a screw cap was placed compound RR (from Example 94, part d) (100 mg, 0.163 mmol), [1,1'-bis(diphenylphosphino)-ferrocene]dichloropalladium(II) dichloromethane complex (10 mg) and 3-cyanophenylboronic acid (35 mg, 0.20 mmol). Dimethoxyethane (3 mL) was added, followed by 2.0 N cesium carbonate (0.30 mL, 0.60 mmol). The mixture was heated at 90° C. for 4 hours. The solution was then cooled to room temperature and partitioned between ethyl acetate and water. The organic layer was dried (Na₂SO₄), concentrated and dried under reduced pressure. The residue was dissolved in DCM (5 mL) and cooled to 0° C., and then boron trichloride (1.0 N in DCM, 2.0 mL, 2.0 mmol) was added. After 10 minutes the reaction was quenched with methanol (20 mL), and concentrated under reduced pressure. The residue was purified by reverse phase HPLC. Fractions containing pure product were combined and lyophilized to give a TFA salt of compound 95. $^1$H NMR (300 MHz, DMSO-d6) δ 10.47 (s, 1H), 10.38 (s, 1H), 8.57 (br s, 2H) 8.05 (d, 1H), 7.89 (m, 1H), 7.82 (m, 1H), 7.70 (m, 2H), 7.53 (t, 2H), 7.07 (d, 1H), 6.95-7.00 (m, 4H), 6.85-6.92 (m, 3H), 6.50 (dd, 1H), 6.09 (d, 1H), 5.22 (d, 1H), 3.65 (s, 3H), 3.10 (m, 4H), 2.80 (m, 2H); m/z: [M+H$^+$] calcd for $C_{33}H_{30}N_4O_4$ 547.24. found 547.5.

Examples 96-102

Synthesis of Compounds 96-102

Using procedures similar to that described in Example 95, except replacing the 3-cyanophenylboronic acid with the appropriate substituted phenylboronic acid, TFA salts of compounds 96-102 were prepared.

Compound 96: N-{2-[4-(3-(4-aminomethylphenyl)-4-methoxyphenyl)aminophenyl]ethyl}-(R)-2-hydroxy-2-(8-hydroxy-2(1H)-quinolinon-5-yl)ethylamine (Formula (XI) where $R^{11}$ is 4-(aminomethyl)phenyl): $^1$H NMR (300 MHz, DMSO-d6) δ 10.47 (s, 1H), 10.40 (s, 1H), 8.58 (br s, 2H), 8.07 (m, 4H), 7.87 (s, 1H), 7.40 (dd, 4H), 7.07 (d, 1H), 6.84-7.05 (m, 8H), 6.50 (dd, 1H), 6.11 (d, 1H), 5.23 (d, 1H), 3.98 (m, 2H), 3.62 (s, 3H), 3.05 (m, 2H), 2.95 (m, 2H), 2.75 (m, 2H); m/z: [M+H$^+$] calcd for $C_{33}H_{34}N_4O_4$ 551.27. found 551.5.

Compound 97 N-{2-[4-(3-(4-pyridyl)-4-methoxyphenyl)aminophenyl]ethyl}-(R)-2-hydroxy-2-(8-hydroxy-2(1H)-quinolinon-5-yl)ethylamine (Formula (XI) where $R^{11}$ is 4-pyridyl): $^1$H NMR (300 MHz, DMSO-d6) δ 10.46 (s, 1H), 10.42 (s, 1H), 8.65 (d, 2H), 8.62 (br s, 1H), 8.06 (d, 2H), 7.97 (br s, 1H), 7.73 (d, 2H) 6.95-7.10 (m, 7H), 6.90 (dd, 2H), 6.12 (br s, 1H), 5.23 (d, 1H), 3.69 (s, 3H), 3.10 (m, 4H), 2.80 (m, 2H); m/z: [M+H$^+$] calcd for $C_{31}H_{30}N_4O_4$ 523.24. found 523.6.

Compound 98: Formula (XI) where $R^{11}$ is 4-formylphenyl: $^1$H NMR (300 MHz, DMSO-d6) δ 10.46 (s, 1H), 10.39 (s, 1H), 9.95 (s, 1H), 8.57 (br s, 2H), 8.05 (d, 1H), 7.91 (br s, 1H), 7.85 (d, 2H), 7.61 (d, 2H), 6.95-7.10 (m, 7H), 6.89 (dd, 2H), 6.50 (dd, 1H), 6.10 (s, 1H), 5.22 (d, 1H), 3.65 (s, 3H), 3.05 (m, 4H), 2.75 (m, 2H); m/z: [M+H$^+$] calcd for $C_{33}H_{31}N_3O_5$ 550.24. found 550.6.

Compound 99: Formula (XI) where $R^{11}$ is 4-methylsulfonyl: $^1$H NMR (300 MHz, DMSO-d6) δ 10.46 (s, 1H), 10.38 (s, 1H), 8.55 (br s, 2H), 8.05 (d, 1H), 7.91 (s, 1H), 7.86 (d, 2H), 6.74 (d, 2H), 6.93-7.10 (m, 6H), 6.85-6.92 (m, 3H), 6.51 (dd, 1H), 6.09 (d, 1H), 5.22 (d, 1H), 3.65 (s, 3H), 3.17 (s, 3H), 3.05 (m, 4H), 2.75 (m, 2H); m/z: [M+H$^+$] calcd for $C_{33}H_{33}N_3O_6S$ 600.22. found 600.5.

Compound 100: N-{2-[4-(3-(4-hydroxyphenyl)-4-methoxyphenyl)aminophenyl]ethyl}-(R)-2-hydroxy-2-(8-hydroxy-2(1H)-quinolinon-5-yl)ethylamine (Formula (XI) where $R^{11}$ is 4-hydroxyphenyl): Using a procedure similar to that described in Example 95, except replacing the 3-cyanophenylboronic acid with 4-benzyloxyphenylboronic acid, a TFA salt of compound 100 was prepared. $^1$H NMR (300 MHz, DMSO-d6) δ 10.46 (s, 1H), 10.38 (s, 1H), 9.34 (s, 1H), 8.57 (br s, 2H), 8.06 (d, 1H), 7.80 (s, 1H), 7.18 (d, 2H), 7.07 (d, 1H), 6.97 (d, 2H), 6.80-6.90 (m, 6H), 6.69 (d, 2H), 6.51 (dd, 1H), 6.09 (s, 1H), 5.23 (d, 1H), 3.60 (s, 3H), 3.05 (m, 4H), 2.78 (m, 2H); m/z: [M+H] calcd for $C_{32}H_{31}N_3O_5$ 538.24. found 538.5.

Compound 101: N-{2-[4-(3-(thiophen-3-yl)-4-methoxyphenyl)aminophenyl]ethyl}-(R)-2-hydroxy-2-(8-hydroxy-2(1H)-quinolinon-5-yl)ethylamine (Formula (XI) where $R^{11}$ is thiophen-3-yl): $^1$H NMR (300 MHz, DMSO-d6) δ 10.47 (s, 1H), 10.38 (s, 1H), 8.57 (br s, 2H), 8.06 (d, 1H), 7.83 (s, 1H), 6.74 (dd, 1H), 7.48 (dd, 1H), 7.31 (dd, 1H), 7.13 (s, 1H), 7.06 (d, 1H), 6.80-7.00 (m, 7H), 6.51 (dd, 1H), 6.01 (s, 1H), 5.23 (d, 1H), 3.70 (s, 3H), 3.07 (m, 4H), 2.77 (m, 2H); m/z: [M+H$^+$] calcd for $C_{30}H_{29}N_3O_4S$ 528.20. found 528.3.

Compound 102: N-{2-[4-(3-(3-chlorophenyl)-4-methoxyphenyl)aminophenyl]ethyl}-(R)-2-hydroxy-2-(8-hydroxy-2(1H)-quinolinon-5-yl)ethylamine (Formula (XI) where $R^{11}$ is 3-chlorophenyl): $^1$H NMR (300 MHz, DMSO-d6) δ 10.46 (s, 1H), 10.38 (s, 1H), 8.76 (br s, 1H), 8.62 (br s, 1H), 8.10 (s, 1H), 7.88 (br s, 1H), 7.15-7.23 (m, 5H), 6.85-7.10 (m, 11H), 6.50 (d, 1H), 6.09 (br s, 1H), 5.27 (d, 1H), 3.65 (s, 3H), 3.10 (m, 4H), 2.80 (m, 2H); m/z: [M+H$^+$] calcd for $C_{32}H_{30}ClN_3O_4$ 556.20. found 556.2.

Example 103

Synthesis of N-{2-[4-(3-(4-(4-morpholino)methylphenyl)-4-methoxyphenyl)aminophenyl]ethyl}-(R)-2-hydroxy-2-(8-hydroxy-2(1H)-quinolinon-5-yl)ethylamine (103)

Compound 103: Formula (XI) where $R^{11}$ is 4-(4-morpholino)methylphenyl.

A trifluoroacetate salt of compound 98 (13 mg, 17 μmol) was dissolved in N,N-dimethylformamide (75 μL) and morpholine (7.5 uL, 86 μmol) added at room temperature. After 5 minutes sodium cyanoborohydride (1.1 mg, 17 μmol) was added followed by methanol (75 μL) and then trifluoroacetic acid (9.0 μL, 120 μmol). The mixture was kept at room temperature for 55 minutes at which point HPLC analysis showed the reaction to be substantially complete. The title compound was purified by reverse-phase HPLC. $^1$H NMR (300 MHz, DMSO-d6) δ 10.41-10.47 (m, 3H), 8.82 (br s, 1H), 8.63 (br s, 1H), 8.10 (d, 1H, J=10.2 Hz), 7.88 (br s, 1H), 7.48 (s, 4H), 7.07 (d, 1H, J=8.2 Hz), 6.85-7.0 (m, 8H), 6.50 (d, 1H, J=9.9 Hz), 6.11 (br s, 1H), 5.27 (br m, 1H), 4.27 (br s, 2H), 3.82-3.93 (br m, 2H), 3.64 (s, 3H), 3.58-3.67 (m, 2H), 3.04 (m, 6H), 2.78 (m, 2H); m/z: [M+H$^+$] calcd for $C_{37}H_{40}N_4O_5$ 621.3. found 621.6

Examples 104-110

Synthesis of Compounds 104-110

Using procedures similar to that described in Example 74, except replacing the 3-cyanophenyl boronic acid with the appropriate substituted boronic acid, TFA salts of compounds 104-110 were prepared.

Compound 104: N-{2-[4-(3-(2-isopropylphenyl)phenyl)aminophenyl]ethyl}-(R)-2-hydroxy-2-(8-hydroxy-2(1H)-quinolinon-5-yl)ethylamine (Formula (X) where $R^{11}$ is 2-isopropylphenyl): m/z: [M+H$^+$] calcd for $C_{34}H_{35}N_3O_3$ 534.3. found 534.5.

Compound 105: N-{2-[4-(3-(2,6-dimethylphenyl)phenyl)aminophenyl]ethyl}-(R)-2-hydroxy-2-(8-hydroxy-2(1H)-quinolinon-5-yl)ethylamine (Formula (X) where $R^{11}$ is 2,6-dimethylphenyl): m/z: [M+H$^+$] calcd for $C_{33}H_{33}N_3O_3$ 520.3. found 520.5.

Compound 106: N-{2-[4-(3-(2-cyanophenyl)phenyl)aminophenyl]ethyl}-(R)-2-hydroxy-2-(8-hydroxy-2(1H)-quinolinon-5-yl)ethylamine (Formula (X) where $R^{11}$ is 2-cyanophenyl): m/z: [M+H$^+$] calcd for $C_{32}H_{28}N_4O_3$ 517.2. found 517.4.

Compound 107: N-{2-[4-(3-(2-ethoxyphenyl)phenyl)aminophenyl]ethyl}-(R)-2-hydroxy-2-(8-hydroxy-2(1H)- quinolinon-5-yl)ethylamine (Formula (X) where $R^{11}$ is 2-ethoxyphenyl): m/z: [M+H$^+$] calcd for $C_{33}H_{33}N_3O_4$ 536.3. found 536.3.

Compound 108: N-{2-[4-(3-(2-ethoxy-5-chlorophenyl)phenyl)aminophenyl]ethyl}-(R)-2-hydroxy-2-(8-hydroxy-2(1H)-quinolinon-5-yl)ethylamine (Formula (X) where $R^{11}$ is 2-ethoxy-5-chlorophenyl): m/z: [M+H$^+$] calcd for $C_{33}H_{32}ClN_3O_4$ 570.2. found 570.4.

Compound 109: N-{2-[4-(3-(2-hydroxyphenyl)phenyl)aminophenyl]ethyl}-(R)-2-hydroxy-2-(8-hydroxy-2(1H)-quinolinon-5-yl)ethylamine (Formula (X) where $R^{11}$ is 2-hydroxyphenyl): m/z: [M+H$^+$] calcd for $C_{31}H_{29}N_3O_4$ 508.2. found 508.4.

Compound 110: N-{2-[4-(3-(2-dimethylaminomethylphenyl)phenyl)aminophenyl]ethyl}-(R)-2-hydroxy-2-(8-hydroxy-2(1H)-quinolinon-5-yl)ethylamine (Formula (X) where $R^{11}$ is 2-dimethylaminomethylphenyl): m/z: [M+H$^+$] calcd for $C_{34}H_{36}N_4O_3$ 549.3. found 549.3.

Example 111

Synthesis of N-{2-[4-(3-(3-cyanophenyl)-4-methoxyphenyl)aminophenyl]ethyl}-(R)-2-hydroxy-2-(8-hydroxy-2(1H)-quinolinon-5-yl)ethylamine (95) and N-{2-[4-(3-(3-carbamoylphenyl)-4-methoxyphenyl)aminophenyl]ethyl}-(R)-2-hydroxy-2-(8-hydroxy-2(1H)-quinolinon-5-yl)ethylamine (111)

Compound 95: Formula (XI) where $R^{11}$ is 3-cyanophenyl
Compound 111: Formula (XI) where $R^{11}$ is 3-carbamoylphenyl Using procedures similar to those described in Example 61C and the deprotection step of Example 61B, except replacing the 4-methoxy-3-phenylaniline hydrochloride with 3-(3-cyanophenyl)-4-methoxyaniline in Example 61C, part d, compound 95 was prepared. In addition, compound III was isolated from the reaction sequence. $^1$H NMR (300 MHz, DMSO-d6) δ 10.47 (s, 1H), 10.40 (s, 1H), 8.58 (br 2, 2H), 8.06 (d, 1H), 7.94 (s, 1H), 7.86 (s, 2H), 7.73 (d, 1H), 7.54 (d, 1H), 7.39 (t, 1H), 7.31 (s, 1H), 7.07 (d, 1H), 6.84-7.00 (m, 9H), 6.50 (d, 1H), 6.10 (s, 1H), 5.23 (d, 1H), 3.54 (s, 3H), 3.10 (m, 4H), 2.80 (m, 2H); m/z: [M+H$^+$] calcd for $C_{33}H_{32}N_4O_5$ 565.64. found 565.5.

The intermediate compound 3-(3-cyanophenyl)-4-methoxyaniline was prepared as follows:

a. Synthesis of 2-(3-cyanophenyl)-4-nitroanisole

[1,1'Bis(diphenylphosphino)ferrocene]dichloropalladium (II), complex with dichloromethane(1:1) (1.43 g) was added to a stirred mixture of 3-cyanophenylboronic acid (10.0 g, 61.8 mmol) and 2-bromo-4-nitroanisole (14.35 g, 62 mmol) in 2.0 N cesium carbonate (92.7 mL, 185.4 mmol) and ethylene glycol dimethylether (200 mL). The flask was purged with nitrogen and heated at 90° C. (oil bath) for 4 hours. The mixture was allowed to cool to room temperature overnight, during which time the product precipitated from solution. The solid was collected on a Buchner funnel, washed with water and dried under reduced pressure to give 2-(3-cyanophenyl)-4-nitroanisole (15.7 g).

b. Synthesis of 3-(3-cyanophenyl)-4-methoxyaniline

Zinc dust (20.26 g, 310 mmol) was added in portions over five minutes to a solution of 2-(3-cyanophenyl)-4-nitroanisole (15.7 g, 62 mmol) and ammonium formate (19.48 g, 310 mmol) in methanol (500 mL) and tetrahydrofuran (500 mL). The reaction was complete after stirring for one hour at room temperature. The resulting mixture was filtered and the filtrate was concentrated under reduced pressure. The residue was purified using flash chromatography on silica gel eluting with 5% methanol in dichloromethane to give 3-(3-cyanophenyl)-4-methoxyaniline (10 g, 44 mmol) as a yellow oil.

Example 112

Synthesis of N-{2-[4-(3-(3-aminomethylphenyl)-4-methoxyphenyl)aminophenyl]ethyl}-(R)-2-hydroxy-2-(8-hydroxy-2(1H)-quinolinon-5-yl) ethylamine (112)

Compound 112: Formula (XI) where $R^{11}$ is 3-aminomethylphenyl

Using procedures similar to those described in Example 61C and the deprotection step of Example 61B, except replacing the 4-methoxy-3-phenylaniline hydrochloride with 3-(3-aminomethylphenyl)-4-methoxyaniline in Example 61C, part d, the HCl salt of compound 112 was prepared. $^1$H NMR (300 MHz, DMSO-d6) δ 10.54 (s, 2H), 9.60 (br s, 1H), 8.85 (br s, 1H), 8.46 (s, 3H), 8.30 (d, 1H), 7.57 (s, 1H), 7.44 (m, 3H) 6.90-7.10 (m, 11H), 6.54 (d, 1H), 5.50 (d, 1H), 4.05 (d, 2H), 3.71 (s, 3H), 3.10 (m, 4H), 2.90 (m, 2H). m/z: [M+H$^+$] calcd for $C_{33}H_{34}N_4O_4$ 551.27. found 551.4.

The intermediate compound 3-(3-aminomethylphenyl)-4-methoxyaniline was prepared as follows:

a. Synthesis of 2-(3-aminomethylphenyl)-4-nitroanisole 2-(3-cyanophenyl)-4-nitroanisole (8.0 g) from Example 111, part a, was dissolved in THF (200 mL) and purged with nitrogen. A 11.0M solution of borane in THF (135 mL) was then added, and the reaction was heated at reflux for 4 hours. When the reaction was complete, the mixture was cooled to room temperature and 4.0N HCl in dioxane (25 mL) was added dropwise over 30 minutes. Methanol (200 mL) was slowly added to the acidified solution, and the solvent was removed in vacuo. The resulting gum was redissolved in methanol (150 mL) and concentrated in vacuo to give a solid. The product was dissolved in dichloromethane (150 mL) and cooled to −20° C. to give 2-(3-aminomethylphenyl)-4-nitroanisole which was collected on a filter and dried in vacuo.

b. Synthesis of 3-(3-aminomethylphenyl)-4-methoxyaniline

To a solution of 2-(3-aminomethylphenyl)-4-nitroanisole (5.88 g) in methanol (100 mL) was added 10% palladium on carbon (3.9 g). The reaction mixture was stirred under one atmosphere of hydrogen for 12 hours. The catalyst was removed by filtration and the solvent was removed in vacuo. The residue was partitioned between 1N NaOH and dichloromethane. The organic layer was dried over $Na_2SO_4$ and concentrated. The resulting oil was dissolved in dichloromethane (50 mL) and 4.0N HCl in dioxane was added. The product was collected by filtration and dried in vacuo to give the HCl salt of 3-(3-aminomethylphenyl)-4-methoxyaniline as an off white powder. $^1$H NMR (300 MHz, DMSO-d$_6$) δ 8.46 (m, 2H), 7.33-7.49 (m, 4H), 6.80 (d, J=7.9 Hz, 1H), 6.58-6.61 (m, 2H), 5.82 (br s, 2H), 3.95 (m, 2H), 3.54 (s, 3H)

Example 113

Synthesis of N-{2-[4-(3-(3-(N-isopropylamino)methylphenyl)-4-methoxyphenyl)aminophenyl]ethyl}-(R)-2-hydroxy-2-(8-hydroxy-2(1H)-quinolinon-5-yl) ethylamine (113)

Compound 113: Formula (XI) where $R^{11}$ is 3-(N-isopropylamino)methylphenyl

Using procedures similar to those described in Example 61C and the deprotection step of Example 61B, except replacing the 4-methoxy-3-phenylaniline hydrochloride with 3-[3-(N-isopropylamino)methylphenyl]-4-methoxyaniline in Example 61C, part d, compound 113 was prepared. m/z: [M+H$^+$] calcd for $C_{36}H_{41}N_4O_4$ 593.31. found 593.4.

The intermediate compound 3-[3-(N-isopropylamino)methylphenyl]-4-methoxyaniline was prepared as follows:

a. Synthesis of 2-(3-(N-isopropylamino)methylphenyl)-4-nitroanisole 2-(3-Aminomethylphenyl)-4-nitroanisole (0.10 g, 0.39 mmol) was dissolved in anhydrous acetone (25 mL). The solution was distilled at atmospheric pressure until the volume was reduced to approximately 5 mL. The solution was then distilled under reduced pressure at room temperature to remove the last traces of acetone. The resultant oil was re-dissolved in $CH_2Cl_2$/MeOH (2 mL: 1 mL). Sodium borohydride (44 mg, 3 equiv) was added, and the reaction mixture stirred at room temperature for 2 h. The solution was then diluted with $CH_2Cl_2$ (10 mL), extracted with 1M NaOH (4×5 mL), dried ($Na_2SO_4$), and evaporated to afford 2-(3-(N-isopropylamino)methylphenyl)-4-nitroanisole (120 mg, 0.39 mmol, 100%).

b. Synthesis of 3-[3-(N-isopropylamino)methylphenyl]-4-methoxyaniline 2-(3-(N-Isopropylamino)methylphenyl)-4-nitroanisole (120 mg, 0.39 mmol) was dissolved in MeOH/THF (5 mL:5 mL), and 10% Pd/C (20 mg) was added. The slurry was stirred at room temperature under an atmosphere of $H_2$ for 16 h. The slurry was then filtered and evaporated to afford 3-[3-(N-isopropylamino)methylphenyl]-4-methoxyaniline as a brown oil (101 mg, 0.37 mmol, 96%).

Example 114

Synthesis of N-{2-[4-(3-(3-(N-benzylamino)methylphenyl)-4-methoxyphenyl)aminophenyl]ethyl}-(R)-2-hydroxy-2-(8-hydroxy-2(1H)-quinolinon-5-yl)ethylamine (114)

Compound 114: Formula (XI) where $R^{11}$ is 3-(N-benzylamino)methylphenyl

N-{2-[4-(3-(3-(N-benzylamino)methylphenyl)-4-methoxyphenyl)aminophenyl]ethyl}-(R)-2-tert-butyldimethylsilyloxy-2-(8-hydroxy-2(1H)-quinolinon-5-yl)ethylamine (55 mg, 0.73 mmol) was dissolved in THF/MeOH (5 mL:2 mL). Triethylamine-trihydrofluoride (0.5 mL) was added, and the reaction mixture was stirred at room temperature for 5 h. The solvent was then evaporated, and the residue purified by HPLC to afford N-{2-[4-(3-(3-(N-benzylamino)methylphenyl)-4-methoxyphenyl)aminophenyl]ethyl}-(R)-2-hydroxy-2-(8-hydroxy-2(1H)-quinolinon-5-yl)ethylamine (114). m/z: [M+H$^+$] calcd for $C_{40}H_{41}N_4O_4$ 641.31. found 641.3

The intermediate N-{2-[4-(3-(3-(N-benzylamino)methylphenyl)-4-methoxyphenyl)aminophenyl]ethyl}-(R)-2-tert-butyldimethylsilyloxy-2-(8-hydroxy-2(1H)-quinolinon-5-yl)ethylamine was prepared as follows:

a. Synthesis of 2-(3-aminomethylphenyl)-4-nitroanisole hydrochloride

To a stirring solution of 2-(3-cyanophenyl)-4-nitroanisole from Example 111 (4.0 g, 16 mmol) in tetrahydrofuran (100 mL) was added borane-tetrahydrofuran complex dropwise (48 mL of a 1.0 M solution in tetrahydrofuran, 3 equiv, 48 mmol). The solution was heated to reflux for 3 hours. The solution was allowed to cool to room temperature and hydrochloride acid (24 mL of 4.0 M solution in dioxane, 96 mmol) was added slowly. Methanol (100 mL) was added slowly and the solution was evaporated to dryness. The residue was diluted with methanol (100 mL) and evaporated to dryness. The residue was dissolved in dichloromethane (100 mL). A clear solution was achieved, from which a precipitate began to form (<1 min). The solution was stirred at room temperature for 14 hours and the solid was collected on a Büchner funnel, washed with dichloromethane (10 mL), and dried under high vacuum to afford 2-(3-aminomethylphenyl)-4-nitroanisole hydrochloride (2.26 g, 55% yield).

b. Synthesis of 3-(3-aminomethylphenyl)-4-methoxyaniline dihydrochloride

To a solution of 2-(3-aminomethylphenyl)-4-nitroanisole hydrochloride (1.26 g, 4.2 mmol) in methanol (10 mL) and tetrahydrofuran (10 mL) under nitrogen was added palladium on carbon (10% by weight, 200 mgs, 15 wt. %). The solution was purged with hydrogen and stirred under hydrogen for 24 hours. The reaction was purged with nitrogen and the catalyst was removed by filtration. Solvent was removed in vacuo and the residue was redissolved in dichloromethane (10 mL) and hydrochloride acid was added (4.0 M solution in dioxane, 1.5 equiv., 1.57 mL). The solution was stirred for 1 hour while a solid precipitated. The solid was collected on a Buchner funnel and dried under vacuum to afford 3-(3-aminomethylphenyl)-4-methoxyaniline dihydrochloride (947 mgs, 73% yield).

c. Synthesis of N-{2-[4-(3-(3-aminomethylphenyl)-4-methoxy)aminophenyl]ethyl}-(R)-2-tert-butyldimethylsilyloxy-2-(8-benzyloxy-2(1H)-quinolinon-5-yl)ethylamine Using procedures similar to those described in Example 61C, except replacing the 4-methoxy-3-phenylaniline hydrochloride with 3-(3-aminomethylphenyl)-4-methoxyaniline in Example 61C, part d, N-{2-[4-(3-(3-aminomethylphenyl)-4-methoxy)aminophenyl]ethyl}-(R)-2-tert-butyldimethylsilyloxy-2-(8-benzyloxy-2(1H)-quinolinon-5-yl)ethylamine was prepared.

d. Synthesis of N-{2-[4-(3-(3-aminomethylphenyl)-4-methoxy)aminophenyl]ethyl}-(R)-2-tert-butyldimethylsilyloxy-2-(8-hydroxy-2(1H)-quinolinon-5-yl)ethylamine N-{2-[4-(3-(3-aminomethylphenyl)-4-methoxy)aminophenyl]ethyl}-(R)-2-tert-butyldimethylsilyloxy-2-(8-benzyloxy-2(1H)-quinolinon-5-yl)ethylamine (140 mg, 0.19 mmol) was dissolved in EtOH (5 mL). Palladium hydroxide (20% w/w on carbon, 20 mg) was added, and the slurry was stirred at room temperature under an atmosphere of $H_2$ for 16 h. The reaction mixture was filtered and the filtrate evaporated to afford N-{2-[4-(3-(3-aminomethylphenyl)-4-methoxy)aminophenyl]ethyl}-(R)-2-tert-butyldimethylsilyloxy-2-(8-hydroxy-2(1H)-quinolinon-5-yl)ethylamine e. Synthesis of N-{2-[4-(3-(3-(N-benzylamino)methylphenyl)-4-methoxyphenyl)aminophenyl]ethyl}-(R)-2-tert-butyldimethylsilyloxy-2-(8-hydroxy-2(1H)-quinolinon-5-yl)ethylamine N-{2-[4-(3-(3-aminomethylphenyl)-4-methoxy)aminophenyl]ethyl}-(R)-2-tert-butyldimethylsilyloxy-2-(8-hydroxy-2(1H)-quinolinon-5-yl)ethylamine (27.5 mg, 0.41 mmol) and benzaldehyde (4.2 µL, 1 equiv) were dissolved in anhydrous MeOH (2 mL) and stirred at room temperature for 2.5 h. Sodium borohydride (9.4 mg, 6 equiv) was added, and the reaction mixture was stirred at rt for 48 h. The solution was then diluted with EtOAc (50 mL), washed with $H_2O$ (30 mL), dried ($Na_2SO_4$), and evaporated to afford N-{2-[4-(3-(3-(N-benzylamino)methylphenyl)-4-methoxyphenyl)aminophenyl]ethyl}-(R)-2-tert-butyldimethylsilyloxy-2-(8-hydroxy-2(1H)-quinolinon-5-yl)ethylamine (26 mg, 0.34 mmol, 83%)

Example 115

Synthesis of N-{2-[4-(3-(3-(N,N-dimethylamino)methylphenyl)-4-methoxyphenyl)aminophenyl]ethyl}-(R)-2-hydroxy-2-(8-hydroxy-2(1H)-quinolinon-5-yl)ethylamine (115)

Compound 115: Formula (XI) where $R^{11}$ is 3-(N,N-dimethylamino)methylphenyl.

Using procedures similar to those described in Example 61C and the deprotection step of Example 61B, except replacing the 4-methoxy-3-phenylaniline hydrochloride with 3-[3-(N,N-dimethylamino)methylphenyl]-4-methoxyaniline in Example 61C, part d, compound 115 was prepared. m/z: [M+H$^+$] calcd for $C_{35}H_{39}N_4O_4$, 579.30. found 579.3

The intermediate compound 3-[3-(N,N-dimethylamino)methylphenyl]-4-methoxyaniline was prepared as follows:

a. Synthesis of 2-(3-(N,N-dimethylamino)methylphenyl)-4-nitroanisole 2-(3-Aminomethylphenyl)-4-nitroanisole (0.21 g, 0.81 mmol) was dissolved in a mixture of formic acid (12 mL) and 37% aqueous formaldehyde (6 mL). The solution was then refluxed for 16 h. The reaction mixture was diluted with 1M NaOH (10 mL) and extracted with $CH_2Cl_2$ (2×10 mL). The combined organic phases were filtered, dried ($Na_2SO_4$) and evaporated to afford 2-(3-(N,N-dimethylamino)methylphenyl)-4-nitroanisole (200 mg, 0.70 mmol, 86%)

b. Synthesis of 3-[3-(N,N-dimethylamino)methylphenyl]-4-methoxyaniline 2-(3-(N,N-Dimethylamino)methylphenyl)-4-nitroanisole (200 mg, 0.70 mmol) was dissolved in EtOH/$H_2O$ (5 mL:2.5 mL). concentrated HCl (40 uL) was added, followed by iron powder (314 mg). The reaction mixture was refluxed for 1 h, allowed to cool to room temperature, and diluted with EtOH (10 mL). The slurry was filtered and the filtrate evaporated. The resultant oil was taken up in 1 M NaOH (10 mL) and extracted with $CH_2Cl_2$ (2×10 mL). The combined organic phases were dried ($Na_2SO_4$) and evaporated to afford 3-[3-(N,N-dimethylamino)methylphenyl]-4-methoxyaniline as a brown oil (102 mg, 0.40 mmol, 57%)

Example 116

Synthesis of N-{2-[4-(3-(3-(N-(3-pyridylmethyl)aminomethyl)phenyl)-4-methoxyphenyl)aminophenyl]ethyl}-(R)-2-hydroxy-2-(8-hydroxy-2(1H)-quinolinon-5-yl)ethylamine (116)

Compound 116: Formula (XI) where $R^{11}$ is 3-[N-(3-pyridylmethyl)aminomethyl]phenyl.

Using procedures described in Example 114, part e, except using pyridine-3-carboxaldehyde in place of benzaldehyde, N-{2-[4-(3-(3-(N-(3-pyridylmethyl)aminomethyl)phenyl)-4-methoxyphenyl)aminophenyl]ethyl}-(R)-2-hydroxy-2-(8-hydroxy-2(1H)-quinolinon-5-yl)ethylamine was synthesized. m/z: [M+H$^+$] calcd for $C_{39}H_{40}N_5O_4$ 642.31. found 642.4

Example 117

Synthesis of N-{2-[4-(3-(3-(N-(4-methoxybenzylamino))methylphenyl)-4-methoxyphenyl)aminophenyl]ethyl}-(R)-2-hydroxy-2-(8-hydroxy-2(1H)-quinolinon-5-yl)ethylamine (117)

Compound 117: Formula (XI) where $R^{11}$ is 3-(N-(4-methoxybenzylamino))methylphenyl.

Using procedures described in Example 114 part e, except using 4-methoxybenzaldehyde in place of benzaldehyde, N-{2-[4-(3-(3-(N-(4-methoxybenzylamino))methylphenyl)-4-methoxyphenyl)aminophenyl]ethyl}-(R)-2-hydroxy-2-(8-hydroxy-2(1H)-quinolinon-5-yl)ethylamine was synthesized. m/z: [M+H$^+$] calcd for $C_{41}H_{43}N_4O_5$ 671.32. found 671.5

Example 118

Synthesis of N-{2-[4-(3-(4-aminomethylphenyl)-4-methoxyphenyl)aminophenyl]ethyl}-(R)-2-hydroxy-2-(8-hydroxy-2(1H)-quinolinon-5-yl)ethylamine (96)

Using procedures similar to those described in Example 61C and the deprotection step of Example 61B, except replacing the 4-methoxy-3-phenylaniline hydrochloride with 3-(4-aminomethylphenyl)-4-methoxyaniline in Example 61C, part d, compound 96 was prepared.

The intermediate compound 3-(4-aminomethylphenyl)-4-methoxyaniline was prepared as follows:

a. Synthesis of 2-(4-aminomethylphenyl)-4-nitroanisole

A mixture of 2-bromo-4-nitroanisole (5.80 g, 25.0 mmol) and 4-(aminomethyl)phenylboronic acid hydrochloride (4.96 g, 26.6 mmol) was slurried in 1-propanol (50 mL) under nitrogen. Triphenylphosphine (315 mg, 1.20 mmol) and palladium (II) acetate (90 mg, 0.40 mmol) were added, followed by 2.0N sodium carabonate (33 mL, 66 mmol). The mixture was heated at 95° C. (oil bath) under nitrogen for 3 hours, at which time the reaction was judged to be complete by TLC. Water (25 mL) was added and the mixture was stirred open to air for 2 hours at room temperature. The mixture was extracted with ethyl acetate (100 mL, 2×50 mL) and the combined extracts were washed with sodium bicarbonate (25 mL) and brine (25 mL). The solution was dried with sodium sulfate, and concentrated to an oil which was purified by flash chromatography on silica gel (100 g) eluting with 0-4% methanol/0.5% triethylamine/dichloromethane. Pure fractions were combined and concentrated to give 2-(4-aminomethylphenyl)-4-nitroanisole (4.6 g) as a yellow solid.

b. Synthesis of 3-(4-aminomethylphenyl)-4-methoxyaniline

A solution of 2-(4-aminomethylphenyl)-4-nitroanisole (4.50 g) in methanol (200 mL) was treated with 10% palladium on carbon (200 mg). The reaction mixture was stirred under one atmosphere of hydrogen for 2.5 hours. The reaction mixture filtered through Celite, and the filter cake washed with methanol (3×25 mL). The filtrate was concentrated to dryness and the residue was purified by flash chromatography on silica gel (80 g) eluting with 0-6% methanol/0.5% triethylamine/dichloromethane. Pure fractions were combined and concentrated to give 3-(4-aminomethylphenyl)-4-methoxyaniline as an off white powder.

Example 119

Synthesis of N-{2-[4-(3-(3-chlorophenyl)-4-methoxyphenyl)aminophenyl]ethyl}-(R)-2-hydroxy-2-(8-hydroxy-2(1H)-quinolinon-5-yl)ethylamine (102)

Using procedures similar to those described in Example 61C and the deprotection step of Example 61B, except replacing the 4-methoxy-3-phenylaniline hydrochloride with 3-(3-chlorophenyl)-4-methoxyaniline in Example 61C, part d, compound 102 was prepared.

The intermediate compound 3-(3-chlorophenyl)-4-methoxyaniline was prepared as follows:

a. Synthesis of 2-(3-chlorophenyl)-4-nitroanisole

To a flask containing a bi-phasic mixture of 2-bromo-4-nitroanisole (15.0 g, 64.6 mmol) and 3-chlorophenylboronic acid (12.1 g, 77.6 mmol) in ethylene glycol dimethyl ether (187.5 mL) and 2.0 N aqueous cesium carbonate (97 mL) was added 1-1'-bis(diphenylphosphino)ferrocene)dichloro palladium (II), complex with dichloromethane (1:1) (1.5 g). The mixture was heated at reflux for 4 hours under a nitrogen atmosphere. The crude reaction mixture was partitioned between ethyl acetate (350 mL) and brine (250 mL) and then filtered through a Buchner funnel. Layers were separated and the organic layer washed with brine (250 mL). The organic phase was dried over $Na_2SO_4$, filtered, and concentrated to a dark oil. The crude residue was purified by flash chromatography on silica gel using dichloromethane as the eluent to afford 2-(3-chlorophenyl)-4-nitroanisole as a yellow solid (13.9 g, 59.4 mmol).

b. Synthesis of 3-(3-chlorophenyl)-4-methoxyaniline

To a mixture of 2-(3-chlorophenyl)-4-nitroanisole (0.5 g, 1.9 mmol) in tetrahydrofuran (5 mL) and methanol (5 mL) was added platinum (IV) oxide (1 mg). The reaction was stirred at room temperature under one atmosphere of hydrogen for 4.5 hours. The slurry was filtered through Celite and concentrated under reduced pressure to afford 3-(3-chlorophenyl)-4-methoxyaniline as a light yellow oil (405 mg, 1.7 mmol).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A method of treating a pulmonary disease in a mammal, wherein the pulmonary disease is asthma or chronic obstructive pulmonary disease, the method comprising administering to the mammal a therapeutically-effective amount of a compound of formula (IIa):

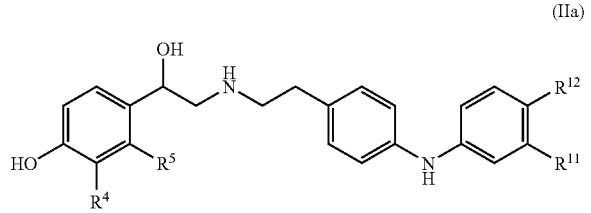

wherein:
$R^4$ is —$CH_2OH$ or —NHCHO and $R^5$ is hydrogen; or $R^4$ and $R^5$ taken together are —NHC(=O)CH=CH—;
$R^{11}$ is phenyl or heteroaryl, wherein each phenyl is optionally substituted with 1 or 2 substituents selected from halo, —$OR^d$, —CN, —$NO_2$, —$SO_2R^d$, —C(=O)$R^d$, —C(=O)$NR^dR^e$, and $C_{1-3}$alkyl, wherein $C_{1-3}$alkyl is optionally substituted with 1 or 2 substituents selected from carboxy, hydroxy, and amino, and each $R^d$ and $R^e$ is independently hydrogen or $C_{1-3}$alkyl; and wherein each heteroaryl is optionally substituted with 1 or 2 $C_{1-3}$alkyl substituents; and
$R^{12}$ is hydrogen or —$OC_{1-6}$alkyl;
or a pharmaceutically-acceptable salt or stereoisomer thereof;
and a therapeutically-effective amount of a corticosteroid selected from 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

2. The method of claim 1 wherein the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

3. The method of claim 2 wherein $R^{11}$ is phenyl, optionally substituted with 1 substituent selected from halo, —$OR^d$, —CN, —$NO_2$, —$SO_2R^d$, —C(=O)$R^d$, and $C_{1-3}$alkyl, wherein $C_{1-3}$alkyl is optionally substituted with 1 or 2 substituents selected from carboxy, hydroxy, and amino, and $R^d$ is hydrogen or $C_{1-3}$alkyl.

4. The method of claim 2 wherein $R^{11}$ is pyridyl, thiophenyl, furanyl, pyrrolyl, isoxazolyl, or indolyl, each of which is optionally substituted with 1 or 2 $C_{1-3}$alkyl substituents.

5. The method of claim 2 wherein $R^{11}$ is phenyl, pyridyl, or thiophenyl, wherein each phenyl is optionally substituted with 1 substituent selected from the group consisting of chloro, —$OCH_3$, —CN, and —$CH_2NH_2$; and $R^{12}$ is hydrogen, —$OCH_3$, or —$OC_2H_5$.

6. The method of claim 5 wherein $R^4$ and $R^5$ taken together are —NHC(=O)CH=CH—; $R^{11}$ is phenyl or pyridyl, wherein each phenyl is optionally substituted with 1 substituent selected from the group consisting of chloro, —$OCH_3$, —CN, and —$CH_2NH_2$; and $R^{12}$ is —$OCH_3$.

7. The method of claim 2 wherein the compound of formula (IIa) is a mixture of stereoisomers wherein the amount of the stereoisomer having the (R) orientation at the chiral center to which the hydroxy group is attached is greater than the amount of the stereoisomer having the (S) orientation at the chiral center to which the hydroxy group is attached.

8. The method of claim 2 wherein the compound of formula (IIa) is the stereoisomer having the (R) orientation at the chiral center to which the hydroxy group is attached.

9. The method of claim 2 wherein the compound of formula (IIa) is selected from:
N-{2-[4-(3-phenyl-4-methoxyphenyl)aminophenyl]ethyl}-(R)-2-hydroxy-2-(8-hydroxy-2(1H)-quinolinon-5-yl)ethylamine;
N-{2-[4-(3-(4-aminomethylphenyl)-4-methoxyphenyl)aminophenyl]ethyl}-(R)-2-hydroxy-2-(8-hydroxy-2(1H)-quinolinon-5-yl)ethylamine;
N-{2-[4-(3-(3-cyanophenyl)-4-methoxyphenyl)aminophenyl]ethyl}-(R)-2-hydroxy-2-(8-hydroxy-2(1H)-quinolinon-5-yl)ethylamine;
N-{2-[4-(3-(3-chlorophenyl)-4-methoxyphenyl)aminophenyl]ethyl}-(R)-2-hydroxy-2-(8-hydroxy-2(1H)-quinolinon-5-yl)ethylamine; and
N-{2-[4-(3-(3-aminomethylphenyl)-4-methoxyphenyl)aminophenyl]ethyl}-(R)-2-hydroxy-2-(8-hydroxy-2(1H)-quinolinon-5-yl)ethylamine;
or a pharmaceutically-acceptable salt thereof.

10. The method of claim 9 wherein the compound of formula (IIa) is N-{2-[4-(3-phenyl-4-methoxyphenyl)aminophenyl]ethyl}-(R)-2-hydroxy-2-(8-hydroxy-2(1H)-quinolinon-5-yl)ethylamine or a pharmaceutically-acceptable salt thereof.

11. The method of claim 1 wherein the pulmonary disease is asthma.

12. The method of claim 1 wherein the pulmonary disease is chronic obstructive pulmonary disease.

13. The method of claim 1 wherein the compound of formula (IIa) is formulated for administration by inhalation.

14. The method of claim 10 wherein the pulmonary disease is asthma.

15. The method of claim 10 wherein the pulmonary disease is chronic obstructive pulmonary disease.

16. The method of claim 10 wherein the compound of formula (IIa) is formulated for administration by inhalation.

* * * * *